(12) United States Patent
Smith et al.

(10) Patent No.: US 12,392,781 B2
(45) Date of Patent: Aug. 19, 2025

(54) DEUTERATED INDOLE HEPTAMETHINE CYANINE DYES

(71) Applicant: University of Notre Dame du Lac, South Bend, IN (US)

(72) Inventors: Bradley D. Smith, South Bend, IN (US); Dong-Hao Li, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 18/559,031

(22) PCT Filed: Apr. 7, 2022

(86) PCT No.: PCT/US2022/023799
§ 371 (c)(1),
(2) Date: Nov. 3, 2023

(87) PCT Pub. No.: WO2022/235371
PCT Pub. Date: Nov. 10, 2022

(65) Prior Publication Data
US 2024/0280577 A1     Aug. 22, 2024

Related U.S. Application Data

(60) Provisional application No. 63/246,708, filed on Sep. 21, 2021, provisional application No. 63/219,826, filed on Jul. 8, 2021, provisional application No. 63/184,059, filed on May 4, 2021.

(51) Int. Cl.
*G01N 33/58* (2006.01)
*C09B 23/08* (2006.01)
*C09B 67/44* (2006.01)

(52) U.S. Cl.
CPC ......... *G01N 33/582* (2013.01); *C09B 23/083* (2013.01); *C09B 67/0083* (2013.01); *G01N 2223/04* (2013.01)

(58) Field of Classification Search
CPC .............................. G01N 33/58; C09B 23/08
See application file for complete search history.

(56) References Cited

U.S. PATENT DOCUMENTS

| 4,569,589 | A | 2/1986 | Neufeld |
| 8,110,597 | B2 | 2/2012 | Taniguchi et al. |
| 8,628,753 | B2 * | 1/2014 | Murthy .............. A61K 49/0021 424/9.1 |
| 10,852,294 | B2 | 12/2020 | Everson |
| 2004/0156782 | A1 | 8/2004 | Alam et al. |
| 2006/0051315 | A1 | 3/2006 | Scaria et al. |
| 2014/0105826 | A1 * | 4/2014 | Murthy ................... C09B 11/24 424/9.6 |
| 2017/0130050 | A1 | 5/2017 | Kundu et al. |
| 2018/0273758 | A1 | 9/2018 | Schnermann et al. |
| 2020/0131370 | A1 | 4/2020 | Jarman et al. |
| 2020/0197410 | A1 | 6/2020 | Ostrow et al. |

FOREIGN PATENT DOCUMENTS

| EP | 2579027 B1 | 7/2019 |
| WO | 2001043781 A1 | 6/2001 |
| WO | 03057259 A2 | 7/2003 |
| WO | 2020240514 A1 | 12/2020 |

OTHER PUBLICATIONS

Ruttger et al., Isomerization and Dimerization of Indocyanine Green and a Related Heptamethine Dye, European Journal of Organic Chemistry, 2019, 30, 4791-4796. (Year: 2019).*
Ruttger et al., and Supporting Information, Isomerization and Dimerization of Indocyanine Green and a Related Heptamethine Dye, European Journal of Organic Chemistry, European Journal of Organic Chemistry, 2019, 30, 1-16. (Year: 2019).*
Lipowska et al., A Highly Selective Hydrogen-Deuterium Exchange in Indolium Heptamethine Cyanines, J. Heterocyclic Chemistry, 1993, 30, 1177-1180. (Year: 1993).*
Janekova et al., Deuteration of Heptamethine Cyanine Dyes Enhances Their Emission Efficiency, Chemical Communication, 2024, 60, 1000-1003. (Year: 2024).*
Biotechne, ICG-d7, Tocris, 2025, 1-3. Obtained online at: https://www.tocris.com/products/icg-d7_7749#product-details on Jan. 8, 2025. (Year: 2025).*
Kumar et al., Salt Selection in Drug Development, Pharmaceutical Technology, 2008, 32(3), 1-21. (Year: 2008).*
Li et al., Deuterated Indocyanine Green (ICG) with Extended Aqueous Storage Shelf-Life: Chemical and Clinical Implications, Chemistry—A European Journal, 2021, 27, 14535-14542. (Year: 2021).*
Li et al., Deuterated Indocyanine Green (ICG) with Extended Aqueous Storage Shelf-Life: Chemical and Clinical Implications, Supporting Information, Chemistry—A European Journal, 2021, 27, 1-37. (Year: 2021).*
Wang et al., Self-Assembled Hydrophobin for Producing Water-Soluble and Membrane-Permeable Fluorescent Dye, Scientific Reports, 2016, 6(23061), 1-11. (Year: 2016).*
Matikonda et al., Impact of Cyanine Conformational Restraint in the Near-Infrared Range, The Journal of Organic Chemistry, 2020, 85, 5907-5915. (Year: 2020).*
International Search Report and Written Opinion mailed in International Patent Application No. PCT/US2022/023799 (Jun. 24, 2022).
Sun et al., "Research progress of near-infrared fluorescence probes based on indole heptamethine cyanine dyes in vivo and in vitro", BMC Chemistry, vol. 14, pp. 1-28 (Mar. 30, 2020).

(Continued)

*Primary Examiner* — Amy M Bunker
(74) *Attorney, Agent, or Firm* — Michael Best & Friedrich LLP

(57) ABSTRACT

Described are deuterated indole heptamethine cyanine dyes, aqueous formulations including the deuterated dyes, and methods of using the dyes and formulations for diagnosing and treating abnormal tissue, assessing tissue perfusion, determining cardiac output, determining hepatic function, or ophthalmic angiography.

7 Claims, 47 Drawing Sheets

(56) References Cited

OTHER PUBLICATIONS

Li et al., "Deuterated Indocyanine Green (ICG) with Extended Aqueous Storage Shelf Life: Chemical and Clinical Implications", Chemistry, vol. 27, pp. 14535-14542 (Sep. 24, 2021).
Becher et al., "Derivatives and Reactions of Glutaconaldehyde-IX", Tetrahedron 1979, 35, pp. 1523-1530.
Berezin et al., "Rational Approach to Select Small Peptide Molecular Probes Labeled with Fluorescent Cyanine Dyes for in Vivo Optical Imagine", Biochemistry 2011, 50, pp. 2691-2700.
Berlepsch et al., "H-Aggregates of an Indocyanine Cy5 Dye: Transition from Strong to Weak Molecular Coupling", J. Phys. Chem. B 2015, 119, pp. 11900-11909.
De Valk et al., "First-in-Human Assessment of CRGD-ZW800-1, a Zwitterionic, Integrin-Targeted, Near-Infrared Fluorescent Peptide in Colon Carcinoma", Clin. Cancer Res., 2020, vol. 26, No. 15, pp. 3990-3998.
Desmettre et al., "Fluorescence Properties and Metabolic Features of Indocyanine Green (ICG) as Related to Angiography", Surv. Ophthalmol., 2000, vol. 45, No. 1, pp. 15-27.
Grimm et al., "A General Method to Improve Fluorophores Using Deuterated Auxochromes", JACS Au, 2021, vol. 1, No. 5, pp. 690-696.
Hernot et al., Latest Developments in Molecular Tracers for Fluorescence Image-Guided Cancer Surgery. Lancet Oncol. 2019, 20 (7), e354-e367.
Hibbert et al., "The death of the Job plot, transparency, open science and online tools, uncertainty estimation methods and other developments in supramolecular chemistry data analysis", Chem. Commun. 2016, 52, pp. 12792-12805.
International Preliminary Report on Patenability for Application No. PCT/US2022/023799 dated Oct. 24, 2023 (5 pages).
Kolmakov et al., "Red-Emitting Rhodamine Dyes for Fluorescence Microscopy and Nanoscopy", Chem. A Eur. J., 2010, vol. 16, No. 1, pp. 158-166.
Kuthan et al., "Prepartion of 1-Phenyldihydropyridines Polydeuterated in Their Heterocyclic Ring", Collect. Czechoslov. Chem. Commun. 1982, 47, pp. 3283-3287.
Kuzmin et al., "Complex formation of albumin with tricarbocyanine dyes containing phosphonate groups", Photochem. Photobiol. Sci. 2016, 15, pp. 1377-1384.
Li et al., "Sterically Shielded Heptamethine Cyanine Dyes for Bioconjugation and High Performance Near-Infrared Fluorescence Imaging", Angew. Chem. Int. Ed, 2020, vol. 59, pp. 12154-12161.
Lipowska et al., "A Highly Selective Hydrogen-Deuterium Exchange in Indolium Heptamethine Cyanines", J. Heterocyclic Chem, 1993, vol. 30, pp. 1177-1180.
Mindt et al., "Stability and Degradation of Indocyanine Green in Plasma, Aqueous Solution and Whole Blood", Photochem. Photobiol. Sci., 2018, vol. 17, No. 9, pp. 1189-1196.
Nani et al., "Reactive species involved in the regioselective photooxidation of heptamethine cyanines", Chem. Sci. 2015, 6, pp. 6556-6563.
Norcott et al., "Using 2H Labelling to improve the NMR detectability of pyridine and its derivatives by SABRE", Magn Reson Chem, 2018, vol. 56, pp. 663-671.
Okoh et al., "Promising Near-Infrared Non-Targeted Probes: Benzothiazole Heptamethine Cyanine Dyes", J. Sulfur Chem., 2014, vol. 35, No. 1, pp. 42-56.
Pirali et al., "Applications of Deuterium in Medicinal Chemistry", J. Med. Chem., 2019, vol. 62, pp. 5276-5297.
Reinhart et al., "Indocyanine Green: Historical Context, Current Applications, and Future Considerations", Surg. Innov., 2016, vol. 23, No. 2, pp. 166-175.
Rüttger et al. "Isomerization and Dimerization of Indocyanine Green and a Related Heptamethine Dye" Eur. J. Org. Chem., 2019, pp. 4791-4796.
Stackova et al., "Approach to a Substituted Heptamethine Cyanine Chain by the Ring Opening of Zincke Salts", J. Am. Chem. Soc., 2019, vol. 141, No. 17, pp. 7155-7162.
Thordarson, "Determining association constants from titration experiments in supramolecular chemistry", Chem. Soc. Rev. 2011, 40, pp. 1305-1323.
Toronto Research Chemicals, Product No. I697003 <https://www.trc-canada.com/product-detail/?I697003>, 3 pages.
Urbitsch et al., "A Modular Enantioselective Synthesis of Resolvins D3, E1, and Hybrids", Org. Lett. 2020, 22, pp. 1510-1515.
Van den Berg et al. "Concomitant radio- and fluorescence-guided sentinel lymph node biopsy in squamous cell carcinoma of the oral cavity using ICG-99mTc-nanocolloid," Eur. J. Nucl. Med. Mol. Imaging, 2012, vol. 39, pp. 1128-1136.
Van Manen et al., "A Practical Guide for the Use of Indocyanine Green and Methylene Blue in Fluorescence-Guided Abdominal Surgery", J. Surg. Oncol., 2018, vol. 118, No. 2, pp. 283-300.
Xia et al. "Gallium-68-Labelled Indocyanine Green as a Potential Liver Reserve Imaging Agent" Contrast Media Mol Imaging, 2019, pp. 1-8.
Yau et al., "Deuteration of Indole and N-Methylindole by Raney Nickel Catalysis", J. Label. Compd. Radiopharm. Off. J. Int. Isot. Soc., 1999, vol. 42, No. 7, pp. 709-714.
Zincke et al., "Ueber Dinitrophenylpyridiniumchlorid und dessen Umwandlungsproducte", Justus Liebigs Ann. Chem. 1904, 333, pp. 296-345.
European Patent Office. Extended European Search Report for Application No. 22799267.4, dated Dec. 9, 2024 (8 pages).

* cited by examiner

| Entry | Air | Light | NaN₃ | 1 formed | Weight ratio of ICG to 1 |
|---|---|---|---|---|---|
| 1 | yes | yes | no | yes | 2 : 1 |
| 2 | yes | yes | yes | no | - |
| 3 | no | yes | no | yes | 5 : 1 |
| 4 | no | yes | yes | no | - |
| 5 | yes | no | no | yes | 3 : 1 |
| 6 | yes | no | yes | no | - |
| 7 | no | no | no | yes | 6 : 1 |
| 8 | no | no | yes | no | - |

DEUTERATED INDOLE HEPTAMETHINE CYANINE DYES

CROSS-REFERENCE TO RELATED APPLICATIONS

This application is a U.S. national stage entry of International Patent Application No. PCT/US2022/023799, filed on Apr. 7, 2022, which claims priority to U.S. Provisional Patent Application No. 63/184,059, filed on May 4, 2021, U.S. Provisional Patent Application No. 63/219,826, filed on Jul. 8, 2021, and U.S. Provisional Patent Application No. 63/246,708, filed on Sep. 21, 2021, the entire contents of each of which are fully incorporated herein by reference.

STATEMENT REGARDING FEDERALLY SPONSORED RESEARCH OR DEVELOPMENT

This invention was made with government support under grant R35 GM136212 awarded by the National Institutes of Health. The government has certain rights in the invention.

TECHNICAL FIELD

The present disclosure relates to deuterated heptamethine cyanine dyes, aqueous formulations comprising the same, and methods of employing the compound formulations for diagnostic and treatment applications, such as diagnosing and treating abnormal tissue, assessing tissue perfusion, determining cardiac output, determining hepatic function, and ophthalmic angiography.

INTRODUCTION

Indole heptamethine cyanine dyes, are the most widely used class of cyanine dyes largely due to their ability to generate strong fluorescence emission at the near-infrared (NIR) region of 650-900 nm, and their greater chemical stability and photostability compared with similar cyanines derived from other heterocyclic systems. Heptamethine dyes are structurally characterized as compounds having two N-substituted heterocyclic rings linked by a heptamethine moiety. The heptamethine chain protons are typically assigned using the numbering system shown below:

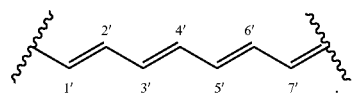

The indole heptamethine cyanine dye Indocyanine Green (ICG) is a clinically approved near-infrared (NIR) fluorescent dye with emission wavelength above 700 nm.

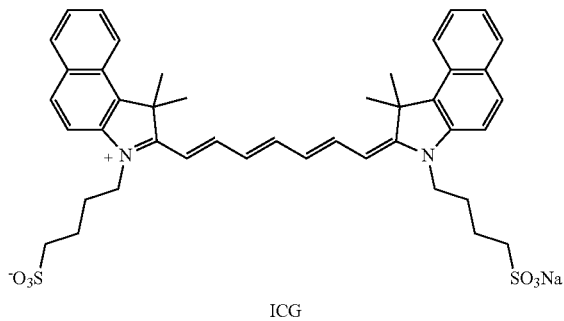

ICG

ICG is commonly employed in a wide range of medical imaging and diagnostic procedures that assess cardiac output or hepatic function, visualize tissue perfusion, lymph nodes, or cancerous tissue before, during and after surgery, or visualize blood flow during ophthalmic angiography. ICG is also commonly used in preclinical research as a NIR fluorescence contrast agent for enhanced imaging of various subject models of disease. The recent discovery that the fluorescence emission tail of ICG extends beyond 1000 nm, and that the fluorescence emission of ICG can be detected using modern commercial cameras heralds a new set of opportunities in short wave infrared (SWIR) imaging. Additionally, there is considerable ongoing development of nanoscale ICG delivery systems for next-generation imaging and treatment strategies. The clinical safety record for ICG over several decades is impressive, and substantial growth in clinical and pre-clinical usage is expected in the coming years.

However, a well-known obstacle regarding ICG is its propensity to degrade rapidly in aqueous solution and generate non-fluorescent by-products. For example, one study found that a 20 μg/mL solution in water had only 20% ICG remaining after sitting for 24 hours, and a rat imaging study reported almost complete loss of vasculature image if the aqueous solution was more than 24 hours old. Because of this rapid decrease in aqueous ICG purity, the FDA recommendation is to discard any unused aqueous sample within six hours of reconstitution. The clinical benefit of ICG would be enhanced if the shelf-life of an aqueous stock solution could be extended, and, not surprisingly, considerable effort has been made over the years to elucidate the degradation pathway(s) and identify the contributing factors.

SUMMARY

In some aspects, the present disclosure provides compounds of formula (I), or pharmaceutically acceptable salts thereof:

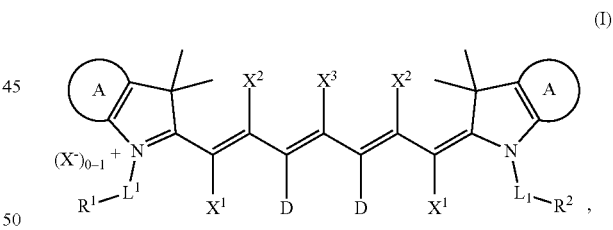

(I)

wherein:

$X^1$, $X^2$, and $X^3$ are each hydrogen;

A is a 6- to 12-membered arene, wherein A is unsubstituted or substituted with 1-5 substituents independently selected from the group consisting of $C_{1-4}$alkyl, —$OC_{1-4}$ alkyl, $C_{1-2}$haloalkyl, —$OC_{1-2}$haloalkyl, halogen, —CN, —$NH_2$, —$NH(C_{1-4}$alkyl), —$N(C_{1-4}$alkyl)$_2$, —$YO_n^-$, —$YO_nH$, and —$YO_nM$;

L' is a bivalent straight or branched $C_{1-25}$ hydrocarbon chain, wherein L' is unsubstituted or substituted with 1-5 substituents independently selected from the group consisting of halogen, —$OC_{1-4}$alkyl, $C_{1-2}$haloalkyl, —$OC_{1-2}$haloalkyl, —OH, —CN, —$NH_2$, —$NH(C_{1-4}$alkyl), and —$N(C_{1-4}$alkyl)$_2$; wherein optionally one or more methylene units are independently replaced with —$CH_2$=$CH_2$—, —O—, —$CO_2$—, —C(O)—, —S—, —S(O)—, —SO$_2$—, —N(H)—, —N(C$_{1-4}$alkyl)-, —C(O)N(H)—, or —C(O)N(C$_{1-4}$alkyl)-; and where 2 methylene groups replaced with —O—, —CO$_2$—, —C(O)—, —S—, —S(O)—, —SO$_2$—, —N(H)—, —N(C$_{1-4}$alkyl)-, —C(O)N(H)—, or —C(O)N(C$_{1-4}$alkyl)- are separated by two or more carbon atoms in the alkylene;

R$^1$ and R$^2$ are each independently —YO$_n^-$, —YO$_n$M, —YO$_n$H, or hydrogen;

Y is sulfur or carbon;

n is 2, 3, or 4;

M is an alkali metal cation;

X$^-$ is chloride, bromide, iodide, perchlorate, or hypochlorite;

with the proviso that when R$^1$ or R$^2$ is —YO$_n^-$, X$^-$ is absent, and the compound is not

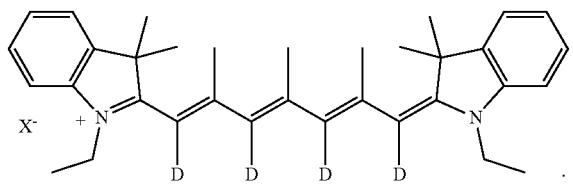

In other aspects, the present disclosure provides aqueous formulations comprising compounds of formula (I), or pharmaceutically acceptable salts thereof, water, and at least one pharmaceutically acceptable excipient.

In other aspects, the present disclosure provides methods for identifying abnormal tissue in a subject during an operative, radiologic, or endoscopic procedure comprising:
  (a) administering to the subject an aqueous formulation comprising a compound of formula (I), or a pharmaceutically acceptable salt thereof;
  (b) conducting the procedure while illuminating the area of interest with an illumination source emitting electromagnetic radiation; and
  (c) imaging the abnormal tissue with an imaging device.

In other aspects, the present disclosure provides methods for obtaining an angiographic image of tissue in a subject comprising:
  (a) parenterally administering to the subject an aqueous formulation comprising a compound of formula (I), or a pharmaceutically acceptable salt thereof;
  (b) applying energy to cause the compound in the subject to fluoresce; and
  (c) obtaining an angiographic image of the tissue while the compound fluoresces.

In other aspects, the present disclosure provides diagnostic methods comprising:
  (a) parenterally administering a known amount of an aqueous formulation comprising a compound of formula (I), or a pharmaceutically acceptable salt thereof, to a subject;
  (b) continuously measuring the concentration of the compound in the subject's bloodstream; and
  (c) analyzing the compound concentration data obtained in (b) to determine the change in compound concentration over time.

In other aspects, the present disclosure provides therapeutic methods for killing or ablating cells and tissue within an area of interest in a subject comprising:
  (a) administering to the subject an aqueous formulation comprising a compound of formula (I), or a pharmaceutically acceptable salt thereof;
  (b) illuminating the area of interest with electromagnetic radiation to cause the compound in the subject to release energy that kills cells or ablates cells and tissue within the area of interest.

DETAILED DESCRIPTION

Figure 1:
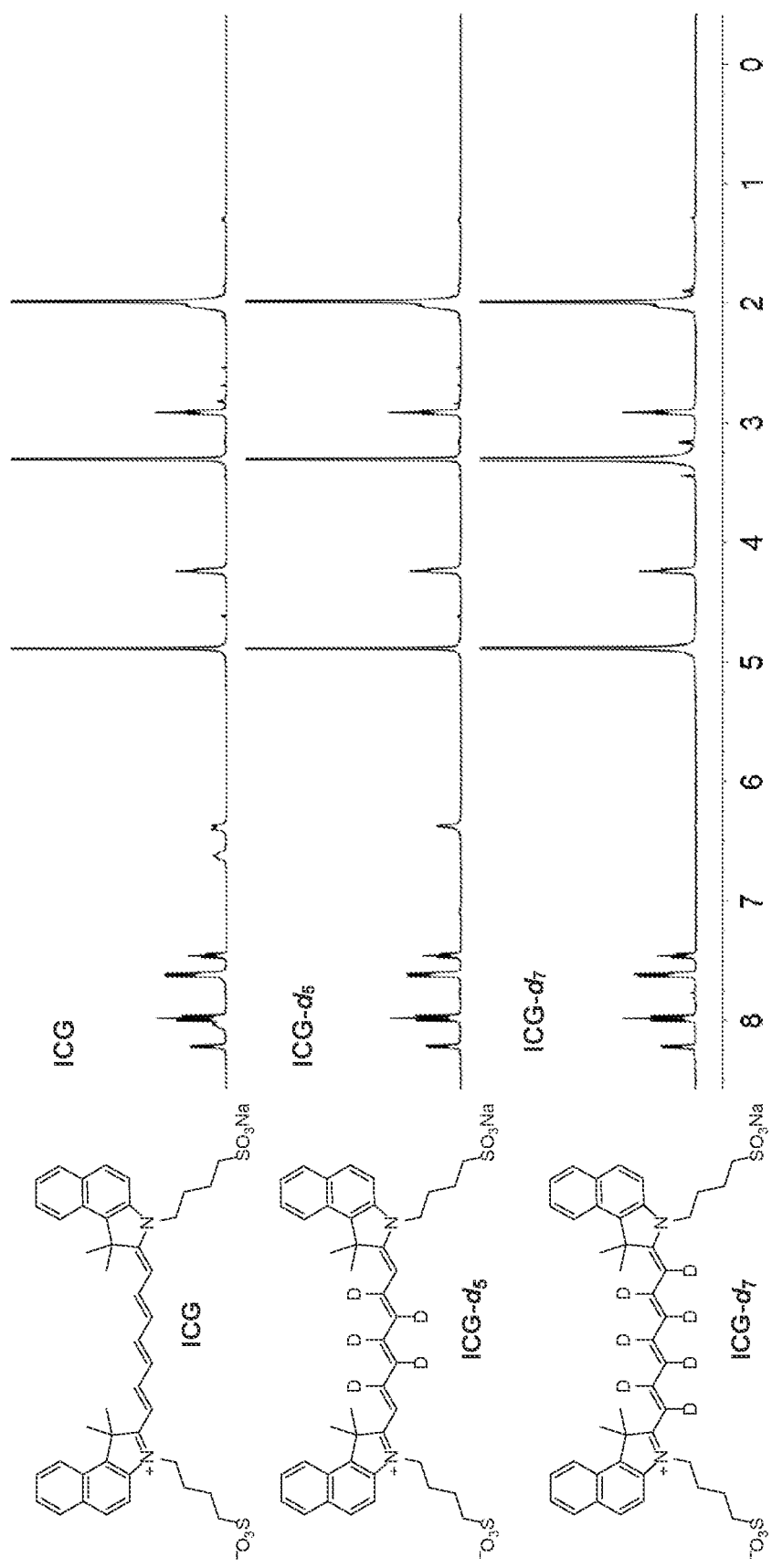
FIG. 1 shows $^1$H NMR (500 MHz, methanol-d$_4$, 25° C.) of Indocyanine Green (ICG) (top), ICG-d$_5$ (middle) and ICG-d$_7$ (bottom).

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various way.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3rd Edition, Cambridge University Press, Cambridge, 1987; the entire contents of each of which are incorporated herein by reference.

The term "alkoxy," as used herein, refers to a group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "C1-6alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cyanoalkyl," as used herein, means at least one —CN group, is appended to the parent molecular moiety through an alkylene group, as defined herein.

The term "cycloalkoxy," as used herein, refers to a cycloalkyl group, as defined herein, appended to the parent molecular moiety through an oxygen atom.

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptanyl). Exemplary monocyclic cycloalkenyl rings include cyclopentenyl, cyclohexenyl or cycloheptenyl. Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The terms cycloalkylene and heterocyclylene refer to divalent groups derived from the base ring, i.e., cycloalkane, heterocycle. For purposes of illustration, examples of cycloalkylene and heterocyclylene include, respectively,

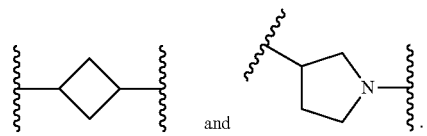 [SMILES: *C1CC(*)C1 ; *C1CCN(*)C1]

and

Cycloalkylene and heterocyclylene include a geminal divalent groups such as 1,1-$C_{3-6}$cycloalkylene (i.e.,

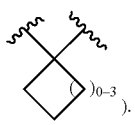

).

A further example is 1,1-cyclopropylene (i.e.,

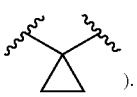

).

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaromatic ring (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g., 1, 2, 3, or 4 heteroatoms independently selected from O, S, and N). The five membered aromatic monocyclic rings have two double bonds, and the six membered aromatic monocyclic rings have three double bonds. The bicyclic heteroaryl is an 8- to 12-membered ring system and includes a fused bicyclic heteroaromatic ring system (i.e., $10\pi$ electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic $10\pi$ electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, tetrahydroisoquinolinyl, 7-oxabicyclo[2.2.1]heptanyl, hexahydro-2H-cyclopenta[b]furanyl, 2-oxaspiro[3.3]heptanyl, 3-oxaspiro[5.5]undecanyl, 6-oxaspiro[2.5]octan-1-yl, and 3-oxabicyclo[3.1.0]hexan-6-yl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, azaadamantane (1-azatricyclo[3.3.1.1$^{3,7}$]decane), and oxaadamantane (2-oxatricyclo[3.3.1.1$^{3,7}$]decane). The monocyclic, bicyclic, and tricyclic heterocyclyls are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

Terms such as "alkyl," "cycloalkyl," "alkylene," etc. may be preceded by a designation indicating the number of atoms present in the group in a particular instance (e.g., "$C_{1\text{-}4}$alkyl," "$C_{3\text{-}6}$cycloalkyl," "$C_{1\text{-}4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1\text{-}4}$," the members of the group that follows may have any number of carbon atoms falling within the recited range. A "$C_{1\text{-}4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

In the compounds of formula (I) or (Ia), and any subformulas, any "hydrogen" or "H," whether explicitly recited or implicit in the structure, encompasses hydrogen isotopes $^1$H (protium) and $^2$H (deuterium).

The present disclosure also includes an isotopically-labeled compound (e.g., deuterium labeled), where an atom in the isotopically-labeled compound is specified as a particular isotope of the atom. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Isotopically-enriched forms of compounds of formula (I) or (Ia), or any subformulas, may generally be prepared by conventional techniques known to those skilled in the art or by processes analogous to those described in the accompanying Examples using an appropriate isotopically-enriched reagent in place of a non-isotopically-enriched reagent. The extent of isotopic enrichment can be characterized as a percent incorporation of a particular isotope at an isotopically-labeled atom (e.g., % deuterium incorporation at a deuterium label).

2. COMPOUNDS

A. Compounds of Formula (I)

In some aspects, the invention provides compounds of formula (I), wherein $X^1$, $X^2$, $X^3$, $X^4$, $R^1$, $R^2$, $L^1$, Y, M, and $X^-$ are as defined herein.

Throughout the embodiments and description of the compounds of the invention, instances of haloalkyl may be fluoroalkyl (e.g., any $C_{1\text{-}4}$haloalkyl may be $C_{1\text{-}4}$fluoroalkyl).

Unsubstituted or substituted rings (i.e., optionally substituted) such as aryl and heteroaryl, are composed of both a ring system and the ring system's optional substituents. Accordingly, the ring system may be defined independently of its substituents, such that redefining only the ring system leaves any previous optional substituents present. For example, a 5- to 12-membered heteroaryl with optional substituents may be further defined by specifying the ring system of the 5- to 12-membered heteroaryl is a 5- to 6-membered heteroaryl (i.e., 5- to 6-membered heteroaryl ring system), in which case the optional substituents of the 5- to 12-membered heteroaryl are still present on the 5- to 6-membered heteroaryl, unless otherwise expressly indicated.

In the following, embodiments of the invention are disclosed. The first embodiment is denoted E1, the second embodiment is denoted E2 and so forth.

E1. A compound of formula (I), or a pharmaceutically acceptable salt thereof:

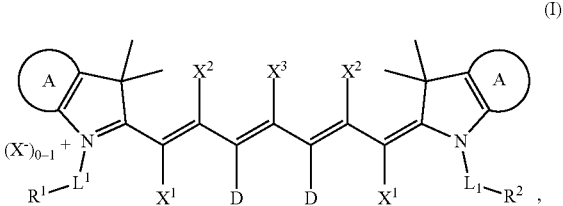

(I)

wherein:

$X^1$, $X^2$, and $X^3$ are each hydrogen;

A is a 6- to 12-membered arene, wherein A is unsubstituted or substituted with 1-5 substituents independently selected from the group consisting of $C_{1\text{-}4}$alkyl, —$OC_{1\text{-}4}$ alkyl, $C_{1\text{-}2}$haloalkyl, —$OC_{1\text{-}2}$haloalkyl, halogen, —CN, —$NH_2$, —NH($C_{1\text{-}4}$alkyl), —N($C_{1\text{-}4}$alkyl)$_2$, —$YO_n^-$, —$YO_n$H, and —$YO_n$M;

$L^-$ is a bivalent straight or branched $C_{1\text{-}25}$ hydrocarbon chain, wherein $L^1$ is unsubstituted or substituted with 1-5 substituents independently selected from the group consisting of halogen, —$OC_{1\text{-}4}$alkyl, $C_{1\text{-}2}$haloalkyl, —$OC_{1\text{-}2}$haloalkyl, —OH, —CN, —$NH_2$, —NH($C_{1\text{-}4}$alkyl), and —N($C_{1\text{-}4}$alkyl)$_2$; wherein optionally one or more methylene units are independently replaced with —$CH_2$=$CH_2$—, —O—, —$CO_2$—, —C(O)—, —S—, —S(O)—, —$SO_2$—, —N(H)—, —N($C_{1\text{-}4}$alkyl)-, —C(O)N(H)—, or —C(O)N($C_{1\text{-}4}$alkyl)-; and where 2 methylene groups replaced with —O—, —$CO_2$—, —C(O)—, —S—, —S(O)—, —$SO_2$—, —N(H)—, —N($C_{1\text{-}4}$alkyl)-, —C(O)N(H)—, or —C(O)N($C_{1\text{-}4}$ alkyl)- are separated by two or more carbon atoms in the alkylene;

$R^1$ and $R^2$ are each independently —$YO_n^-$, —$YO_n$M, —$YO_n$H, or hydrogen;

Y is sulfur or carbon;

n is 2, 3, or 4;

M is an alkali metal cation; and $X^-$ is chloride, bromide, iodide, perchlorate, or hypochlorite;

with the proviso that when $R^1$ or $R^2$ is —$YO_n^-$, $X^-$ is absent, and the compound is not

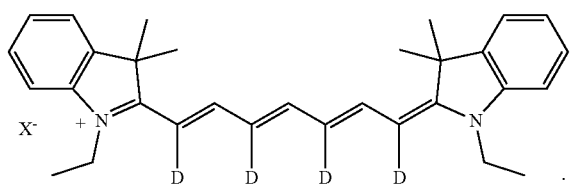

E2. The compound of embodiment 1, or a pharmaceutically acceptable salt thereof, wherein $R^1$ is $-YO_n^-$.

E3. The compound of embodiment 1 or 2, or a pharmaceutically acceptable salt thereof, wherein $R^2$ is $-YO_nM$ where M is Na.

E4. The compound of any one of embodiments 1-3, or a pharmaceutically acceptable salt thereof, wherein Y is sulfur.

E5. The compound of any one of embodiments 1-4, or a pharmaceutically acceptable salt thereof, wherein n is 3.

E6. The compound of any one of embodiments 1-5, or a pharmaceutically acceptable salt thereof, wherein the hydrogen at $X^1$, $X^2$, and $X^3$ are each deuterium.

E7. The compound of any one of embodiments 1-5, or a pharmaceutically acceptable salt thereof, wherein the hydrogen at $X^1$ and $X^2$ are each deuterium.

E8. The compound of any one of embodiments 1-5, or a pharmaceutically acceptable salt thereof, wherein the hydrogen at $X^2$ and $X^3$ are each deuterium.

E9. The compound of any one of embodiments 1-5, or a pharmaceutically acceptable salt thereof, wherein the hydrogen at $X^3$ is deuterium.

E10. The compound of any one of embodiments 1-5, or a pharmaceutically acceptable salt thereof, wherein the hydrogen at $X^2$ is deuterium.

E11. The compound of any one of embodiments 1-5, or a pharmaceutically acceptable salt thereof, wherein the hydrogen at $X^1$ is deuterium.

E12. The compound of any one of embodiments 1-11, or a pharmaceutically acceptable salt thereof, wherein the compound is selected from the group consisting of:

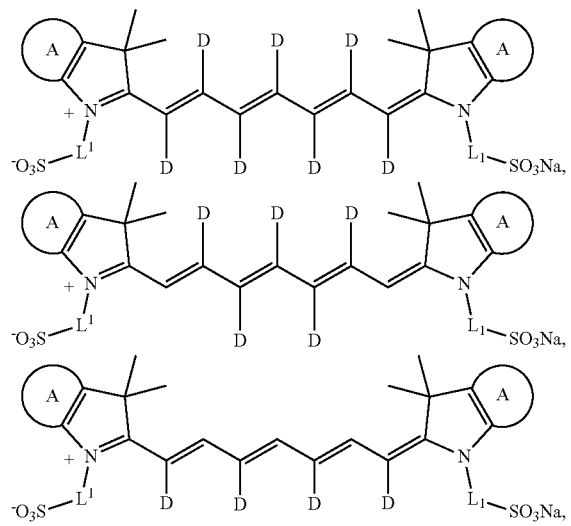

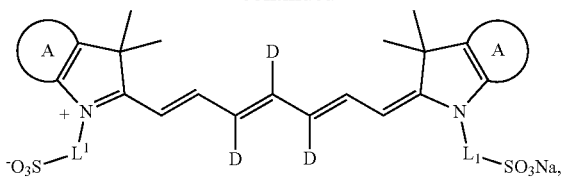

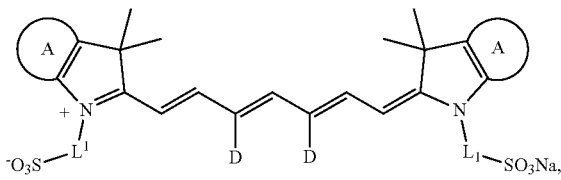

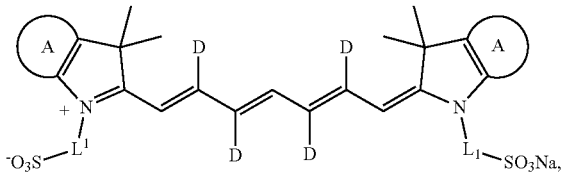

and

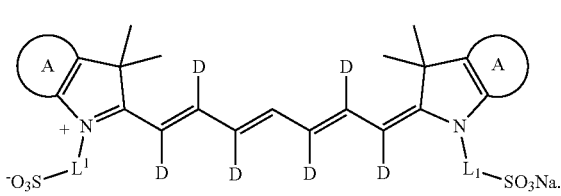

E13. The compound of any one of embodiments 1-12, or a pharmaceutically acceptable salt thereof, wherein A is

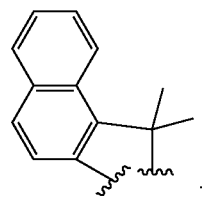 [SMILES: *c1ccc2ccccc2c1C(*)(C)C]

E14. The compound of any one of embodiments 1-13, or a pharmaceutically acceptable salt thereof, wherein A is

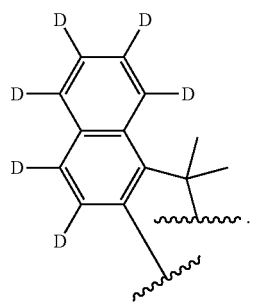 [SMILES: *Cc1c([2H])c([2H])c2c([2H])c([2H])c([2H])c([2H])c2c1C(*)(C)C]

E15. The compound of any one of embodiments 1-14, or a pharmaceutically acceptable salt thereof, wherein L' is a $C_{1-10}$ hydrocarbon chain.

E16. The compound of any one of embodiments 1-15, or a pharmaceutically acceptable salt thereof, wherein L' is

E17. The compound of any one of embodiments 1-16, or a pharmaceutically acceptable salt thereof, wherein the compound is a compound of formula (Ia):

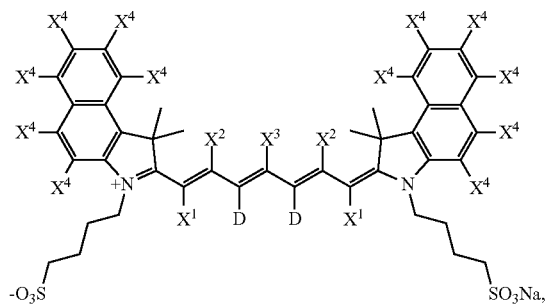

where $X^1$, $X^2$, $X^3$, and $X^4$ are each hydrogen.

E18. The compound of embodiment 17, or a pharmaceutically acceptable salt thereof, wherein the hydrogen at $X^1$, $X^2$, and $X^3$ are each deuterium.

E19. The compound of embodiment 17, or a pharmaceutically acceptable salt thereof, wherein the hydrogen at $X^1$ and $X^2$ are each deuterium.

E20. The compound of embodiment 17, or a pharmaceutically acceptable salt thereof, wherein the hydrogen at $X^2$ and $X^3$ are each deuterium.

E21. The compound of embodiment 17, or a pharmaceutically acceptable salt thereof, wherein the hydrogen at $X^3$ is deuterium.

E22. The compound of embodiment 17, or a pharmaceutically acceptable salt thereof, wherein the hydrogen at $X^2$ is deuterium.

E23. The compound of embodiment 17, or a pharmaceutically acceptable salt thereof, wherein the hydrogen at $X^1$ is deuterium.

E24. The compound of embodiment 17, or a pharmaceutically acceptable salt thereof, wherein the hydrogen at $X^1$, $X^2$, $X^3$, and $X^4$ are each deuterium.

E25. The compound of any one of embodiments 1-24, or a pharmaceutically acceptable salt thereof, wherein the compound is selected from the group consisting of

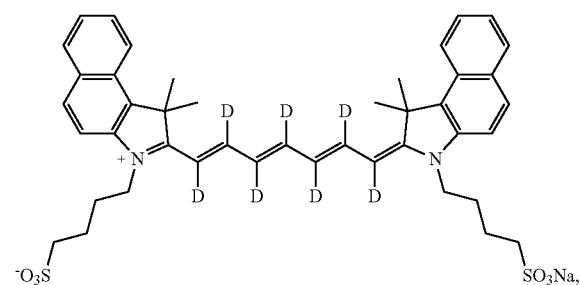

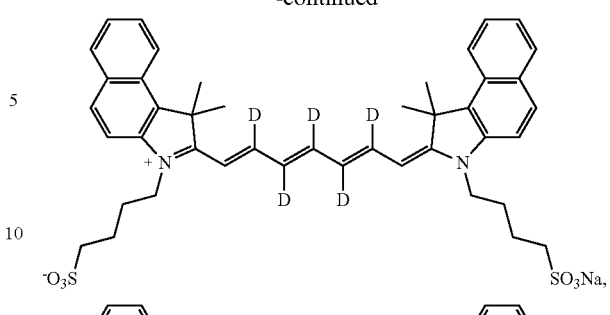

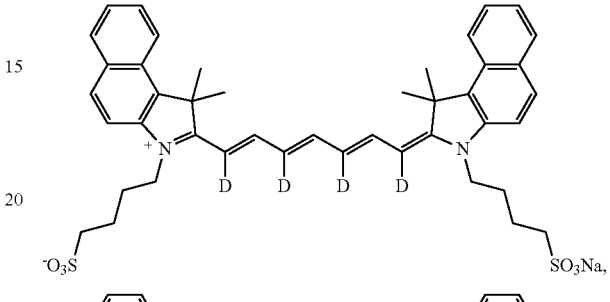

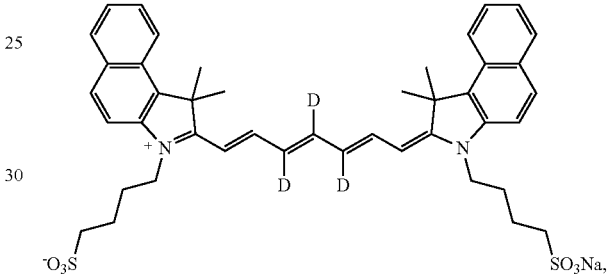

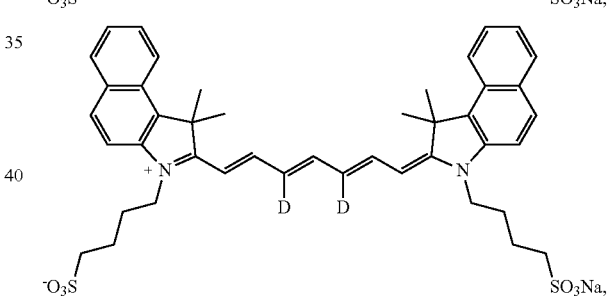

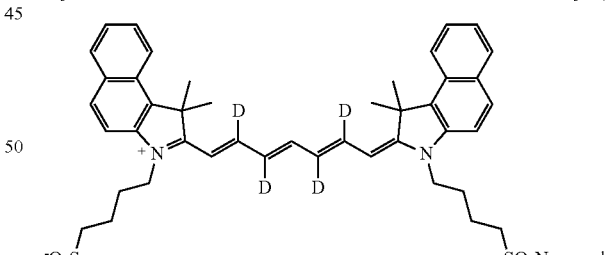

and

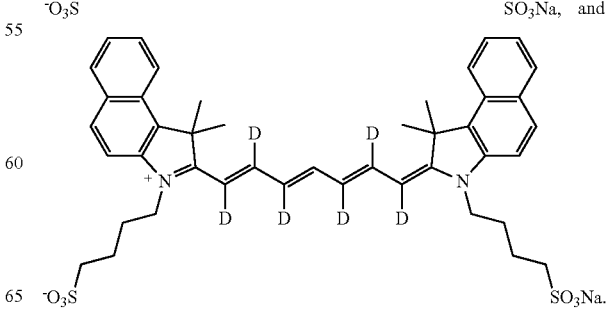

E26. A compound of any one of embodiments 1-25, or a pharmaceutically acceptable salt thereof, wherein that compound has at least 50% deuterium incorporation at each deuterium label.

E27. A compound of any one of embodiments 1-26, or a pharmaceutically acceptable salt thereof, wherein that compound has at least 75% deuterium incorporation at each deuterium label.

E28. A compound of any one of embodiments 1-27, or a pharmaceutically acceptable salt thereof, wherein that compound has at least 90% deuterium incorporation at each deuterium label.

E29. A compound of any one of embodiments 1-28, or a pharmaceutically acceptable salt thereof, wherein that compound has at least 99% deuterium incorporation at each deuterium label.

E30. A compound of any one of embodiments 1-29, or a pharmaceutically acceptable salt thereof, wherein that compound has at least 99.5% deuterium incorporation at each deuterium label.

E31. An aqueous formulation, comprising the compound of any one of embodiments 1-30, or a pharmaceutically acceptable salt thereof, water, and at least one pharmaceutically acceptable excipient.

E32. The aqueous formulation of embodiment 31, wherein at least one of the pharmaceutically acceptable excipients is sodium iodide.

E33. The aqueous formulation of embodiment 31 or 32, wherein at least one of the pharmaceutically acceptable excipients is selected from the group consisting of sodium phosphate, sodium diphosphate, sodium triphosphate, sodium bicarbonate, sodium ascorbate, and combinations thereof.

E34. A method for identifying abnormal tissue in a subject during an operative, radiologic or endoscopic procedure comprising:
(a) administering to the subject the aqueous formulation of any one of embodiments 31-33;
(b) conducting the procedure while illuminating the area of interest with an illumination source emitting electromagnetic radiation; and
(c) imaging the abnormal tissue with an imaging device.

E35. The method of embodiment 34, further comprising treating the abnormal tissue using a method selected from the group consisting of external beam radiation, laser therapy, surgical removal, and combinations thereof.

E36. A therapeutic method for killing or ablating cells and tissue within a site of abnormal tissue in a subject comprising:
(a) administering to the subject the formulation of any one of embodiments 31-33;
(b) illuminating the area of interest with electromagnetic radiation to cause the compound in the subject to release energy that kills cells or ablates cells and tissue within the site of abnormal tissue.

E37. A method for obtaining an angiographic image of tissue in a subject comprising:
(a) parenterally administering to the subject, the aqueous formulation of any one of embodiments 31-33;
(b) applying energy to cause the compound in the subject to fluoresce; and
(c) obtaining an angiographic image of the tissue while the compound fluoresces.

E38. A diagnostic method comprising:
(a) parenterally administering a known amount of the aqueous formulation of any one of embodiments 31-33 to a subject;
(b) continuously measuring the concentration of the compound in the subject's bloodstream; and
(c) analyzing the compound concentration data obtained in (b) to determine the change in compound concentration over time.

B. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

C. General Synthesis

Compounds of formula (I) or any of its subformulas may be synthesized as shown in the following schemes.

Abbreviations which have been used in the Schemes that follow are:
AcONa is sodium acetate;
Ac$_2$O is acetic anhydride;
Ts is tosyl;
Tf is trifluoromethylsulfonyl;
r.t. or rt is room temperature;
PhMe is toluene;
MeCN is acetonitrile;
MeOH is methanol; and
EtOH is ethanol.

Compounds of formula (I) or any of its subformulas may be synthesized as shown in the following schemes.

General Scheme 1

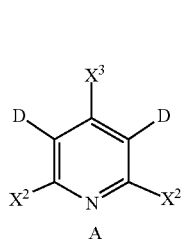

As shown above in General Scheme 1, deuterated pyridine compounds of formula A may be reacted with 2,4-dinitrophenyl 4-methylbenzenesulfonate, 2,4-dinitrophenyl trifluoromethanesulfonate, 2,4-dinitrophenyl bromide, or 2,4-dinitrophenyl chloride to form Zincke salts of formula B. Y=TsO, TfO, Br or Cl.

General Scheme 2

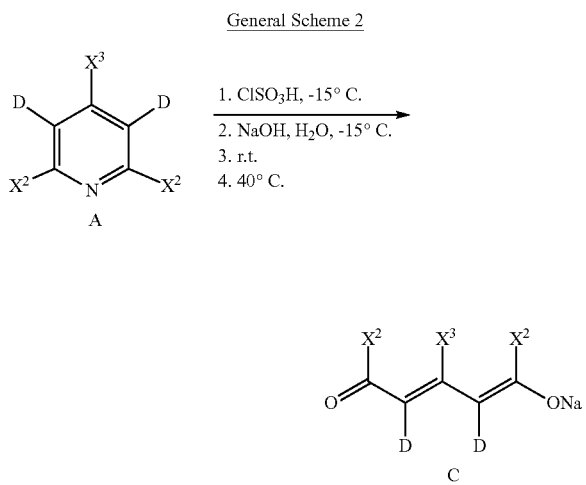

As shown above in General Scheme 2, deuterated pyridine compounds of formula A may be reacted with chlorosulfonic acid under suitable conditions to form glutaconaldehydes of formula C.

General Scheme 3

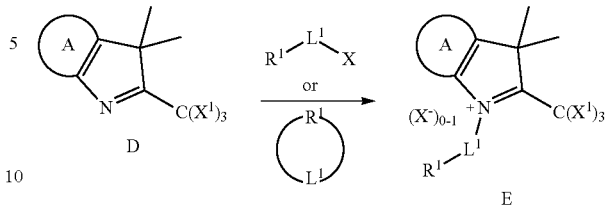

As shown above in General Scheme 3, indole compounds of formula D may be reacted with a cyclic compound of formula or a -$L^1$-$R^1$ substituted halide (X-$L^1$-$R^1$ where X is a halide) under suitable conditions to form an indolenium compounds of formula E.

General Scheme 4

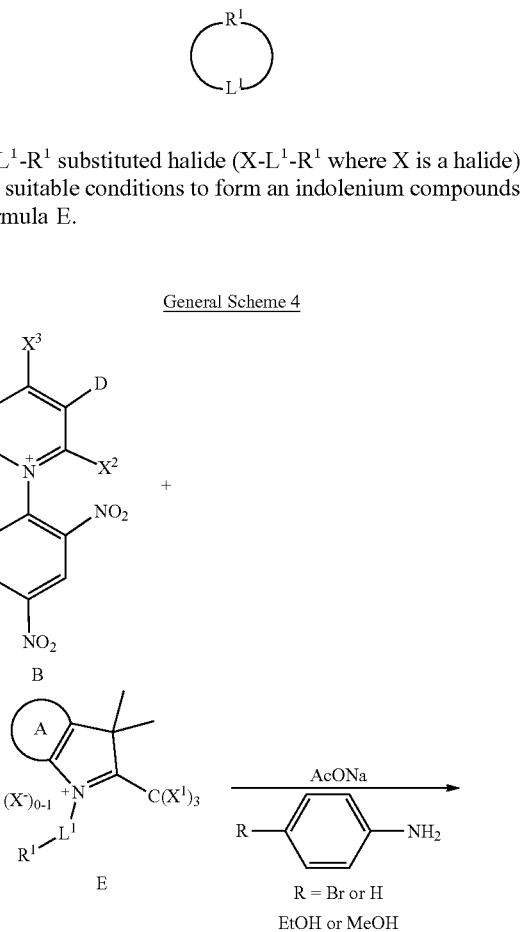

As shown in General Scheme 4, Zincke salts of formula B may be reacted with indolenium compounds of formula E under suitable conditions to form heptamethine compounds of formula F.

General Scheme 5

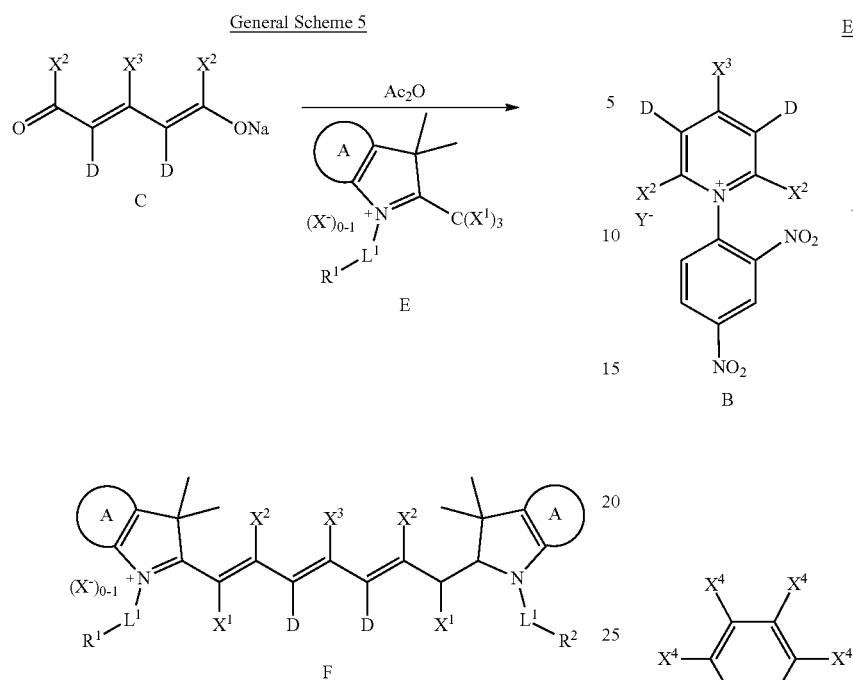

As shown in General Scheme 5, glutaconaldehydes of formula C may be reacted with indolenium compounds of formula E under suitable conditions to form heptamethine compounds of formula F.

Exemplary Scheme 1

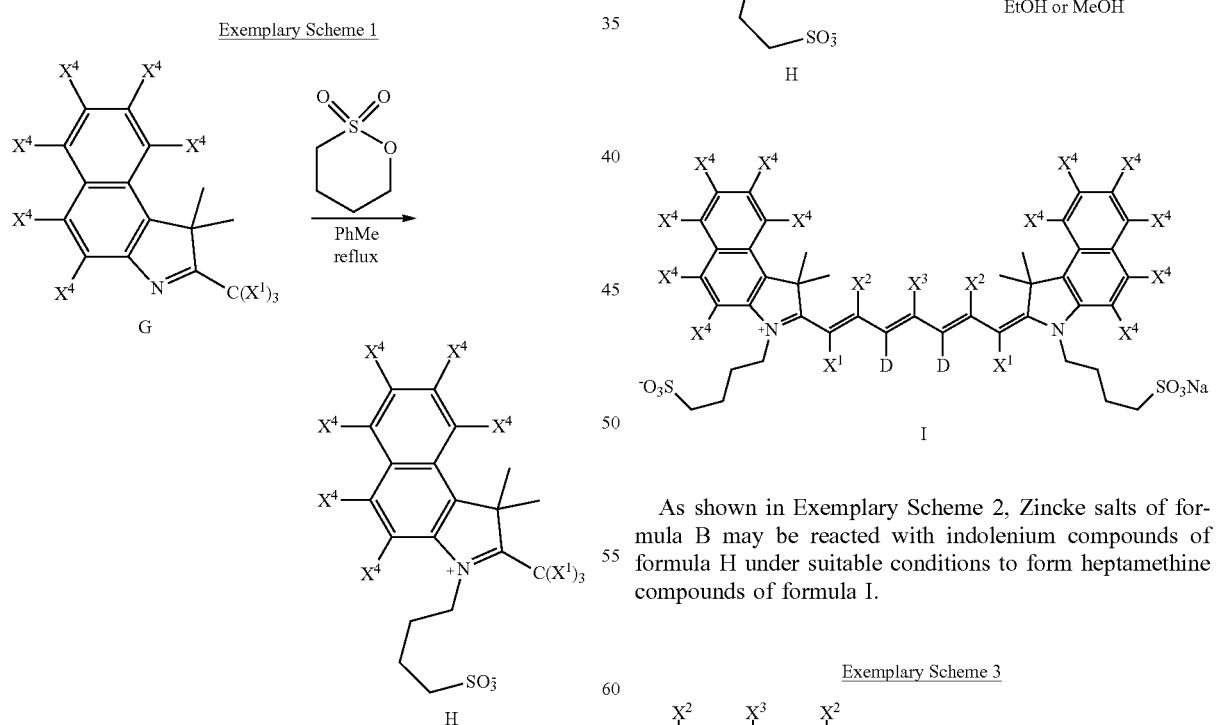

As shown in Exemplary Scheme 1, benzo[e]indoles of formula G may be reacted with 1,2-oxathiane 2,2-dioxide under suitable conditions to form butane-1-sulfonate substituted indolenium compounds of formula H.

Exemplary Scheme 2

As shown in Exemplary Scheme 2, Zincke salts of formula B may be reacted with indolenium compounds of formula H under suitable conditions to form heptamethine compounds of formula I.

Exemplary Scheme 3

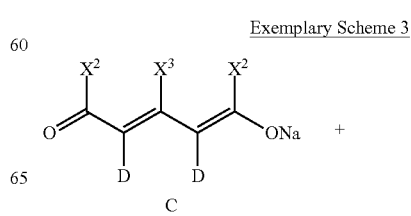

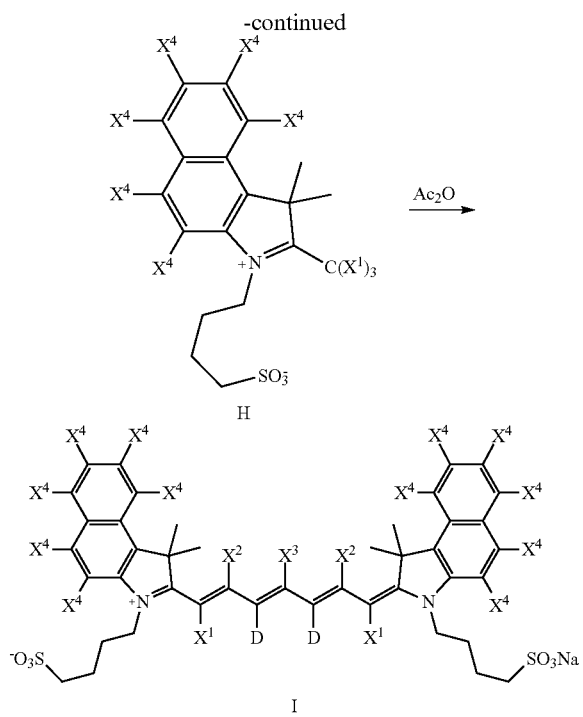

As shown in Exemplary Scheme 3, glutaconaldehydes of formula C may be reacted with indolenium compounds of formula H under suitable conditions to form heptamethine compounds of formula I.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to, tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above-described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization, or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. FORMULATIONS

The disclosed compounds may be incorporated into pharmaceutical compositions or formulations suitable for administration to a living subject (such as a patient, which may be a human or non-human). The disclosed compounds may also be provided as formulations, such as aqueous formulations for intravenous administration.

Pharmaceutical formulations may include pharmaceutically acceptable excipients. The terms "excipient" or "pharmaceutically acceptable excipient" as used herein refer to a diluent, adjuvant, or vehicle with which the compound is administered. Suitable pharmaceutical excipients, techniques, and formulations are generally described in Remington's Essentials of Pharmaceutics, Pharmaceutical Press Publishing Company, London, UK, 1st Edition, 2013, and the Handbook of Pharmaceutical Excipients, 8th Edition, Pharmaceutical Press Publishing Company London, UK, 2017, each of which is incorporated by reference herein for such teachings. Some examples of materials which can serve as pharmaceutically acceptable excipients are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. A pharmaceutically acceptable excipient may be selected from, for example, the group consisting of sodium phosphate, sodium diphosphate, sodium triphosphate, sodium bicarbonate, sodium ascorbate, and combinations thereof. Thus, the compounds and their physiologically acceptable salts and solvates may be formulated for administration by, for example, injection or parenteral administration. Therapeutic compositions must typically be sterile and stable under the conditions of manufacture and storage.

The compound of formula (I) used in the formulation may be provided in any suitable form but is preferably provided in a sterile lyophilizate. When provided as a lyophilizate, the compound of formula (I) is reconstituted prior to administration by use of the aqueous diluent described herein. To effect the reconstitution, water, in the form of sterile water for injection (WFI), may be introduced into a vial holding the compound of formula (I), with the aqueous diluent being added thereafter. Alternatively, the WFI and aqueous diluent may be added in reverse order. Preferably, however, the aqueous diluent is in a vial separate from the compound of formula (I) vial, with the aqueous diluent being introduced into the compound of formula (I)-containing vial in an amount sufficient to provide the desired final compound of formula (I) concentration, more preferably without the need for additional dilution to obtain the desired final compound of formula (I) concentration.

The compound of formula (I) and diluent may also be packaged together, e.g., as a kit, or in a dual chamber configuration, such as a pre-loaded dual chamber syringe or vial. Such syringes and vials maintain separation between the compound of formula (I) and diluent, but permit mixing upon activation, prior to administration.

The aqueous diluent may comprise a solubilizer and alcohol, with water (preferably sterile WFI) being added to reach the desired dilution. The solubilizer may be provided, per mL of diluent, at about 0.5 to about 5 mg, with the alcohol provided at about 50 to about 150 mg on the same basis.

Suitable solubilizers for use in the disclosed formulation may include surface active agents (also referred to as surfactants) and cosolvents (e.g., polyethylene glycol). Surfactants are preferred, with liquid (at 25° C.) nonionic surfactants being most preferred, e.g., Tweens, such as polysorbate 80. In either case, the solubilizer is advantageously a liquid (no more than about 5 cp viscosity, preferably no more than about 3 cp, and most preferably about 1 cp, at 25° C.), e.g., polyethylene glycol having a molecular weight of less than about 800, and more preferably less than about 500. The solubilizer may assist in promoting solvation of the compound of formula (I) in the diluent and enhance the ability of the aqueous compound of formula (I) formulation to be injected into the bloodstream.

The solubilizer may be present in the compound of formula (I) formulation in an amount sufficient to enhance the solubility of the compound of formula (I) in the formulation relative to the same formulation without the solubilizer. However, the inclusion of excessive levels of solubilizer in these relatively concentrated formulations may adversely affect the formulation stability, therefore the amount of solubilizer may be limited to that which provides the aqueous formulation with a stabilizing effect, such as no more than about 7 mg/mL of the aqueous diluent, or no more than about 5 mg/mL. The solubilizer may be present at from about 0.1 mg/mL or from about 0.25 mg/mL to about 5 mg/mL of the aqueous diluent.

The ratio of solubilizer to compound of formula (I) in the aqueous compound of formula (I) formulation, on an absolute weight basis, may range from about 0.1:100 to about 7:10, from about 0.2:100 to about 5:75, and or from about 0.2:75 to about 3:75.

A lower alkyl alcohol may also be included in the formulation. A variety of pharmaceutically acceptable alcohols may be used. Examples of pharmaceutically acceptable alcohols include lower alkanols ($C_{2-3}$ alcohols), diols, and triols, e.g., ethyl alcohol, glycerine, propylene glycol and mixtures thereof.

The alcohol may be included in the diluent to provide enhanced solubility and/or fluorescence of the compound of formula (I) relative to the same formulation without alcohol. The ratio of alcohol to compound of formula (I) on a weight basis may range from about 1:0.25 to about 1:4, about 1:0.5 to about 1:3, or about 1:1 to about 1:2.5. On a weight percentage basis, the alcohol may be present in the aqueous diluent from about 25 mg/mL to about 250 mg/ml of the diluent, from about 50 mg/mL to about 200 mg/mL, or from about 75 to about 125, to about 150 mg/mL.

The amount of alcohol in the diluent may be greater than the amount of solubilizer. The former may be present in at least 50 wt. % excess, up to and including about 200 wt. % excess, relative to the solubilizer. The alcohol may be at least 75 wt. %, up to and including 150 wt. %, or about 85 wt. % to about 125 wt. %, relative to the weight of solubilizer.

The diluent may further include polyvinyl pyrrolidone (PVP). PVP may be present in the aqueous formulation, per mL of diluent, from about 10 to about 100 mg, advantageously from about 25 to about 75 mg, or from about 40 to about 60 mg. As PVP is a polymer, and available at a variety of molecular weights, it may be desirable to utilize a relatively low molecular weight PVP (less than about 30,000, preferably less than about 15,000) to assist in maintaining the viscosity of the aqueous formulation at a relatively low level.

Optionally, the diluent may include an antimicrobial agent. This component may assist in maintaining the sterility of the diluent during storage. While any number of pharmaceutically-acceptable antimicrobials may be used, an antimicrobial that does not adversely affect the solubility and other beneficial properties of the aqueous compound of formula (I) formulation is preferred. Illustrative of such antimicrobials are those containing alcohol functionalities, such as benzoyl alcohol.

The amount of antimicrobial agent may impart antimicrobial activity to the diluent during storage and the aqueous compound of formula (I) formulation. The antimicrobial may be provided, per mL of diluent, at from about 5 mg to about 10 mg per mL of diluent.

The water included in the disclosed formulation is preferably sterilized, e.g., WFI. The amount of water used in the diluent is that required to provide the desired level of compound of formula (I) concentration in the compound of formula (I) formulations, as well as the desired weight percentages of the other diluent components.

As an alternative, one or more of the diluent components may be lyophilized with the compound of formula (I). For example, if included, a pH adjusting agent and/or antimicrobial agent may be lyophilized with the compound of formula (I) and retained within the compound of formula (I) vial until reconstitution with the remaining components of the diluent. Other such combinations of diluent components and compound of formula (I) are possible, depending on the ability of each diluent component to successfully undergo lyophilization with the compound of formula (I).

The compound of formula (I) formulation may be a liposomal compound of formula (I) formulation. In this formulation, the compound of formula (I) may be provided as a lyophilizate which, upon reconstitution with a diluent comprising water (e.g., WFI, saline, and liposome-forming components), provides for encapsulation of the compound of formula (I) in liposomes. Alternatively, the liposome-forming components may be included with the compound of formula (I) in the lyophilizate formulation. After reconstitution, the deuterated compound of formula (I) may be present at a concentration of about 0.5 to about 3 mg/mL of the formulation, or from about 1 to about 2 mg/mL. When reconstituted, the liposomal formulation may comprise from about 1 to about 100 mg compound of formula (I).

The liposome-forming components may be selected from those which are pharmaceutically acceptable. Illustrative components include DL-alpha tocopheryl acetate (about 0.1 to about 1 mg), cholesterol (about 5 to about 50 mg), egg phosphatidylcholine (about 10 to about 100 mg) and tertiary butyl alcohol (about 0.1 to about 10 mL), on a per mL basis.

The disclosed formulation may have relatively low viscosity, rendering it suitable for parenteral administration. More specifically, the viscosity of the diluent, after one month of storage at ambient (25° C.) temperature, may remain less than about 5 centipoise (cp), or less than about 3 cp. The aqueous compound of formula (I) formulation may remain less than about 5 cp, less than about 3 cp, or about 1 cp, up to one week after reconstitution.

A pH adjustment of the reconstituted formulation to between about 6 to about 8 may optionally be completed using effective amounts of any of several pharmaceutically acceptable acids, bases and/or buffer systems. An acid and/or base may be used in an effective amount, e.g., HCl, NaOH, to adjust the pH of the reconstituted formulation to between about 6.5 and 7.5, or about 7.

4. METHODS OF USE

The disclosed compounds may be used in methods for diagnosing and treating abnormal tissue and assessing tissue perfusion, determining cardiac output, determining hepatic function and blood flow, and for ophthalmic angiography.

A. Diagnosis and Treatment of Abnormal Tissue and Assessing Tissue Perfusion Methods of diagnosing and treating abnormal tissue may include a method for identifying abnormal tissue in a subject during an operative, radiologic, or endoscopic procedure. Methods of assessing tissue perfusion may include a method visualizing tissue perfusion in a subject before, during or after an operative, radiologic, or endoscopic procedure.

The said methods may comprise of some or all of the following steps: (a) administering to the subject an aqueous formulation comprising an effective amount of at least one compound of formula (I) in water in a total systemic dose wherein the administration is systemic; (b) conducting said procedure after a waiting period subsequent to said administration, wherein said waiting period is between about 1 minute and about 24 hours; (c) during the procedure, illuminating the region of interest with an illumination source emitting electromagnetic radiation (emr) having at least one wavelength which interacts with a compound of formula (I), the emr having a wavelength of from about 600 nm to about 1000 nm; (d) imaging the region of interest with an imaging device, wherein the region of interest emits fluorescence caused by the compound of formula (I) formulation; (e) optionally imaging the lymph nodes draining from the region of interest; (f) optionally, treating the region of interest by external beam radiation, laser therapy, or surgical removal. Some or all the steps (a) through (f) may be repeated one or more times as part of a single procedure and may draw each administered dose from the same larger stock solution containing a formulation of at least one compound of formula (I) in water.

The abnormal tissue to be identified may be selected from the group consisting of a neoplasia, a tumor, a metastasis, a lymph node, a sentinel lymph node, draining lymph node and combinations thereof. The abnormal tissue may be a neoplasia selected from the group consisting of breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, lymphomas, malignant melanomas, epidermoid carcinomas, lymph node, sentinel lymph node, and combinations thereof. The abnormal tissue may be a pancreatic cancer, breast cancer, or colon cancer. The abnormal tissue may also be atherosclerotic plaque, injured bile duct, endoluminal lesions within the gastrointestinal tract, or ischemic intestinal tissue. In addition to abnormal tissue, other tissues may be the region of interest for static and dynamic tissue perfusion imaging methods that evaluate skin-flap viability during or after operative procedures such as general surgery, plastic and reconstructive surgery, and organ transplants.

Said operative, radiologic, or endoscopic procedure may further comprise treating sites of abnormal tissue by external beam radiation, laser therapy, and/or surgical removal. Additionally, said operative, radiologic, or endoscopic procedure may further comprise a therapeutic method for killing or ablating cells and tissue within a site of abnormal tissue in a subject that includes administering to the subject an aqueous formulation comprising a compound of formula (I), illuminating the area of interest with electromagnetic radiation to cause the compound in the subject to release energy that kills cells or ablates cells and tissue within the site of abnormal tissue.

The illumination source may be selected from the group consisting of electron-stimulated, incandescent, halogen, electroluminescent, LED, gas discharge, xenon, laser, and laser diode. The illumination source may emit emr having at least one wavelength which interacts with the compound of formula (I), the emr having a wavelength of at least 650 nm. The illumination source may emit emr having at least one wavelength which interacts with a compound of formula (I), the emr having a wavelength of about 780 nm. The imaging device may be selected from the group consisting of spectrometer, digital, video camera, and CCD. A combination of lights and filters may be used to create the impression of a glowing abnormal tissue. The method may further comprise imaging devices capable of capturing spectroscopic data from the tissue being imaged.

The method may further comprise imaging devices to convert the near-infrared signal to a visible signal. The imaging device may be selected from the group consisting of devices which can be mounted over the patient, hand-held devices, devices which are attached to a long lens system, minimally invasive cameras, telescopes, endoscopes, esophagoscopes, colonoscopes, laparoscopes, thoracoscope long lens, capsule endoscopes, and combinations thereof. The imaging device may be ingested or implanted in the subject. The imaging device may also record scatter information from the signal that is being emitted from the excited compound of formula (I) formulation preparation in the abnormal tissue in order to improve the depth of penetration and imaging quality. The imaging device may also include an optical coherence tomography device. The imaging device may be modified to excite different compounds of formula (I) separately and simultaneously capture the emission from the different compounds of formula (I), wherein computer software then represents this data simultaneously for an observer.

It should be understood that the concentration of the compound of formula (I) in the aqueous compound of formula (I) formulation should be sufficient to permit reliable imaging of the region of interest. Those skilled in the art can readily determine the amount necessary to yield such reliable measurements using well-known methods. The total amount of the compound of formula (I) administered to the subject may vary depending upon the physical characteristics of the particular subject (e.g., size and overall blood volume), but should be sufficient to yield a compound of formula (I) concentration that permits reliable imaging of the region of interest; however, the amount should not be so high as to cause adverse effects in the subject. Typically for methods of imaging and treating abnormal tissue and assessing tissue perfusion, the amount of the compound of formula (I) administered in a single dose to an adult subject can range from about 2 mg to about 25 mg, and optionally repeated doses may be administered as part of a single procedure. In some procedures, especially a procedure called second window indocyanine green, the amount of the compound of formula (I) administered in a single dose is above the FDA-approved limit of 2 mg/kg and the waiting period between dose administration and imaging is between about 1 day and about 14 days.

B. Determination of Cardiac Output

Methods of determining cardiac output may include determining cardiac output in a subject by introducing a single bolus of a compound of formula (I) into the subject's circulatory system. The concentration of the compound may then be continuously monitored near the point of bolus introduction. This concentration data may then be used to generate a concentration/blood-level versus time curve, which may be used to determine the amount of time required for the bolus to complete one cycle through the subject's circulatory system. The concentration data and time measurements may be used to determine the subject's cardiac output. The method may further comprise continuous measurement of the concentration of the compound of formula (I) in the subject's bloodstream to determine the change in the concentration of compound of formula (I) over time, and the analysis of the compound of formula (I) concentration data to determine the subject's cardiac output.

The aqueous compound of formula (I) formulation may be parenterally administered to the subject by any means known to those of skill in the art. The aqueous compound of formula (I) formulation may be rapidly administered in a single bolus to ensure that dilution of the aqueous compound of formula (I) formulation from the injection is minimized.

To determine the concentration of the compound of formula (I) in the subject's bloodstream, any method known to yield reliable measurements of analogous compound, indocyanine green (IGG), concentration in whole blood may be used. The concentration of the compound of formula (I) in the subject's bloodstream may be measured spectrophotometrically. The concentration of the compound of formula (I) in the subject's bloodstream may be determined by measuring the amount of light absorbed by the subject's blood in the near-infrared region. The concentration of the compound of formula (I) in the subject's bloodstream may be measured by continuous withdrawal of arterial blood, wherein the absorption spectrum of the blood may then be spectrophotometrically measured and compared to standards containing known amounts of compound of formula (I) to determine the concentration of the compound of formula (I) in the subject's bloodstream. Alternatively, the concentration of the compound of formula (I) in the subject's bloodstream may be measured using an ear densitometer or pulse dye densitogram (DDG) analyzer with a finger sensor.

It should be understood that the concentration of the compound of formula (I) in the aqueous compound of formula (I) formulation should be sufficient to permit reliable measurement of the compound of formula (I) concentration in whole blood. Those skilled in the art can readily determine the amount necessary to yield such reliable measurements using well-known methods. The total amount of the compound of formula (I) administered to the subject may vary depending upon the physical characteristics of the particular subject (e.g., size and overall blood volume), but should be sufficient to yield a compound of formula (I) concentration that permits measurement of the compound of formula (I) concentration in the subject's blood; however, the amount should not be so high as to cause adverse effects in the subject. Typically for methods of determining cardiac output, the amount of the compound of formula (I) administered to an adult subject is about 5 mg and the maximum total dose should not exceed 2 mg/kg of subject body weight.

C. Determination of Hepatic Function and Blood Flow

Methods of determining hepatic function and blood flow may include a method of measuring the rate at which compound of formula (I) is eliminated from the subject's bloodstream and comparing that rate to data for persons exhibiting normal hepatic function and liver blood flow. The method may entail injecting a known amount of a compound of formula (I) into the vein of a subject's arm. At regular intervals (e.g., every 5 minutes) or after the lapse of a predetermined amount of time (e.g., 20 minutes), the concentration of a compound of formula (I) in the subject's bloodstream may be measured in a location far removed from the point at which the compound of formula (I) was administered (e.g., a vein in the opposite arm, or the subject's finger or ear). The method may comprise the steps of reconstituting a lyophilized compound of formula (I) with an aqueous diluent to provide an aqueous compound of formula (I) formulation, parenterally administering a known amount of the aqueous compound of formula (I) formulation to a subject, measuring the concentration of the compound of formula (I) in the subject's bloodstream to determine the change in the compound of formula (I) concentration over time, and analyzing the compound of formula (I) concentration data to determine the rate at which the subject's liver eliminates compound of formula (I) from the blood.

The concentration of compound of formula (I) in the subject's bloodstream may be measured using any of the methods described for determining cardiac output.

The percentage disappearance rate (PDR) may be determined by measuring the compound of formula (I) concentration in the subject's bloodstream at regular intervals (e.g., 5, 10, 15, and 20 minutes after injection of the bolus). This concentration data may then be plotted (e.g., using a semilogarithmic scale) and the PDR may be calculated. The percentage retention may be determined by measuring the compound of formula (I) concentration in the subject's bloodstream at a specified time (e.g., 20 minutes after injection of the bolus), then comparing that measurement with the known amount of the compound of formula (I) administered to the subject to determine the percentage of the compound of formula (I) retained in the subject's bloodstream.

It should be understood that the concentration of the compound of formula (I) in the aqueous compound of formula (I) formulation should be sufficient to permit reliable measurement of the compound of formula (I) concentration in whole blood. Those skilled in the art can readily determine the amount necessary to yield such reliable measurements using well-known methods. The total amount of the compound of formula (I) administered to the subject may vary depending upon the physical characteristics of the particular subject (e.g., size and overall blood volume), but should be sufficient to yield a compound of formula (I) concentration that permits measurement of the compound of formula (I) concentration in the subject's blood; however, the amount should not be so high as to cause adverse effects in the subject. Typically for methods of determining hepatic function and blood flow, the dosage of formula (I) administered to an adult subject is calculated as 0.5 mg/kg of body weight, and the maximum total dose should not exceed 2 mg/kg of subject body weight.

D. Ophthalmic Angiography

Methods of ophthalmic angiography aim to facilitate a surgical or diagnostic procedure by imaging a region of interest in the eye, which may include blood vessels or specifically stained tissues or membranes. The aqueous formulation may comprise a compound of formula (I) administered as a systemic dose. Said method may comprise: (a) administering to the subject a compound of formula (I) or an aqueous formulation comprising an effective amount of at least one compound of formula (I), (b) conducting said procedure after a waiting period subsequent to said administration, wherein said waiting period is between about 1 and about 20 minutes; (c) during the procedure, illuminating the region of interest with an illumination source emitting electromagnetic radiation (emr) having at least one wavelength which interacts with the at least one compound of formula (I), the emr having a wavelength of from about 600 nm to about 1000 nm; (d) imaging the eye tissue, optionally with an imaging device, wherein the region of interest displays more fluorescence caused by the compound of formula (I) formulation; (e) optionally, surgically removing or repairing tissue in the region of interest; (f) optionally, treating tissue in the region of interest by external beam radiation, or laser therapy.

The concentration of the compound of formula (I) in the aqueous compound of formula (I) formulation should be sufficient to permit reliable imaging of the region of interest. Those skilled in the art can readily determine the amount necessary to yield such reliable images using well-known methods; however, the amount should not be so high as to cause adverse effects in the subject. Typically for ophthalmic angiography, the total amount of the compound of formula (I) administered to an adult subject can be up to about 40 mg, and the maximum total dose should not exceed 2 mg/kg of subject body weight.

5. EXPERIMENTAL EXAMPLES

Abbreviations that may be used in the examples that follow are:

$Ac_2O$ is acetic anhydride;

NaOAc is sodium acetate;

$PhNH_2$ is aniline;

PhMe is toluene;

EtOH is ethanol;

MeOH is methanol;

MeOD is deuterated methanol;

MeCN is acetonitrile;

$D_2O$ is deuterated water;

THF is tetrahydrofuran;

DMSO is dimethylsulfoxide;

DCI is 4,5-dicyanoimidazole;

FBS is fetal bovine serum;

PBS is phosphate-buffered saline;

BSA is bovine serum albumin;

h or h. is hour(s);

min or min. is minute(s);

cp is centipoise;

rt, RT, or r.t. is room temperature;

sat. is saturated;

eq, eq., or equiv is equivalent(s);

v/v volume per volume;

wt % or wt. % is weight %;

TLC is thin layer chromatography;

UV is ultraviolet;

HRMS is high resolution mass spectrometry;

LCMS is liquid chromatography mass spectrometry; and

ESI-TOF is electrospray ionization time-of-flight.

General Methods

Reagents and solvents were purchased from Sigma-Aldrich, VWR, Oakwood, Thermo Fisher and used without further purification unless stated otherwise. Column chromatography was performed using Biotage Sfär C18 Duo columns (part #FSUD-0401). Reverse- phase thin layer chromatography (TLC) experiments were performed on C18 TLC plates with F254s indicator (MilliporeSigma, part #1.15683). $^1$H NMR spectra were recorded on a Bruker 500 NMR spectrometer. Chemical shifts are presented in ppm and referenced by residual solvent peak. High-resolution mass spectrometry (HRMS) was performed using a time-of-flight (TOF) analyzer with electrospray ionization (ESI), with sample dilution in water/acetonitrile as the standard produre. Electronic absorption spectra were recorded on an Evolution 201 UV/vis spectrometer with Thermo Insight software. Fluorescence spectra were collected on a Horiba Fluoromax-4 fluorometer with a maximum detection wavelength of 850 nm. Analyte solutions were prepared on the lab bench (exposed to air and light) using in HPLC grade water (Sigma-Aldrich), dimethylsulfoxide (Sigma-Aldrich), pH 7.4 1× phosphate buffered saline (Thermo Fisher) or fetal bovine serum (Sigma-Aldrich). Stock solutions for spectroscopy studies were prepared and used within 2 hours. All absorption and fluorescence spectra were collected using quartz cuvettes (1 mL, 1 cm path length).

Example 1: 4-(1,1,2-Trimethyl-1H-3λ$^4$-benzo[e]indol-3-yl)butane-1-sulfonate (Compound 3)

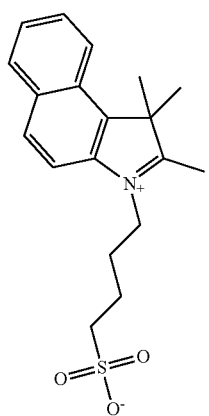 [SMILES: CC1=[N+](CCCCS(=O)(=O)[O-])c2ccc3ccccc3c2C1(C)C]

A mixture of 1,1,2-trimethylbenzo[e]indole (10 g, 47.8 mmol, 1 eq) and 1,4-butane sultone (9.76 g, 71.2 mmol, 1.5 eq) in toluene (20 mL) was stirred vigorously at 140° C. for 12 h. After cooling to room temperature, diethyl ether (200 mL) was added. The solid was collected by filtration and dried to afford 3 as a blue-gray solid (16 g, 97%). $^1$H NMR (500 MHz, DMSO-d$_6$, 25° C.) δ(ppm): 8.35 (d, J=8.5 Hz, 1H), 8.27 (d, J=8.5 Hz, 1H), 8.21-8.19 (m, 2H), 7.77 (dd, J=8.5, 8.5 Hz 1H), 7.71 (dd, J=8.5, 8.5 Hz 1H), 4.59 (t, J=7.8 Hz, 2H), 2.93 (s, 3H), 2.51 (t, J=7.8 Hz, 2H), 2.01 (tt, J=7.8, 7.8 Hz, 2H), 1.77 (m, 1H), 1.74 (s, 6H).

Example 2: Indocyanine Green (ICG)

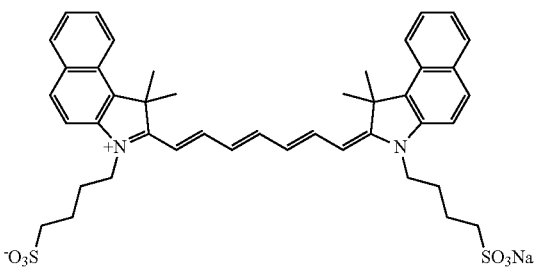

A mixture of glutaconaldehydedianil hydrochloride (300 mg, 1.05 mmol, 1 eq), indolium 3 (910 mg, 2.63 mmol, 2.5 eq) and sodium acetate (259 mg, 3.16 mmol, 3 eq) in ethanol (20 mL) and acetic anhydride (5 mL) was stirred at 75° C. for 3 h under argon atmosphere in the dark. After cooling to room temperature, the solvent was removed under reduced pressure. The residue was suspended in diethyl ether (100 mL) and filtered. The solid was purified by reverse phase column chromatography (55-65% MeOH in H$_2$O). The fractions containing product were combined and the solvent was removed under reduced pressure at 45° C. The residue was dissolved in methanol (5 mL), then diethyl ether (200 mL) was added to precipitate the product. The solid was collected by filtration and dried to afford ICG as a dark green powder (650 mg, 80%). 1H NMR (500 MHz, methanol-d$_4$, 25° C.) δ(ppm): 8.22 (d, J=8.6 Hz, 2H), 8.03 (dd, J=13.6, 12.4 Hz, 2H), 7.98 (m, 4H), 7.61 (m, 5H), 7.46 (dd, J=8.5, 8.5 Hz, 2H), 6.62 (dd, J=12.4, 12.4 Hz, 2H), 6.38 (d, J=13.6 Hz, 2H), 4.24 (t, J=7.3 Hz, 4H), 2.91 (t, J=7.0 Hz, 4H), 2.07-1.94 (m, 20H).

Example 3: 1-(2,4-Dinitrophenyl)pyridin-1-ium-2,3,4,5,6-d$_5$ 4 methyl benzene sulfonate (Compound 2)

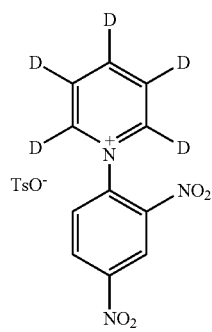 [SMILES: "TsO-" ; [2H]c1c([2H])c([2H])[n+](-c2ccc([N+](=O)[O-])cc2[N+](=O)[O-])c([2H])c1[2H]]

A mixture of pyridine-d$_5$ (750 mg, 8.91 mmol, 1 eq) and 2,4-dinitrophenyl p-toluenesulfonate (3.32 g, 9.81 mmol, 1.1 eq) in acetonitrile (20 mL) was refluxed for 16 h. The reaction was cooled to room temperature and diethyl ether (100 mL) was added. The resulting precipitate was collected by filtration and washed with diethyl ether then dried to afford pyridine-d$_5$ Zincke salt 2 (3.6 g, 95%) as a white solid. $^1$H NMR (500 MHz, DMSO-d$_6$, 25° C.) δ(ppm): 9.11 (d, J=2.4 Hz, 1H), 8.97 (dd, J=8.7, 2.4 Hz, 1H), 8.40 (d, J=8.7 Hz, 1H), 7.45 (d, J=7.8 Hz, 2H), 7.09 (d, J=7.8 Hz, 2H), 2.27 (s, 3H). HRMS (ESI-TOF) m/z: [M]$^+$ calcd for C$_{11}$H$_3$D$_5$N$_3$O$_4$+251.0823, found 251.0825. Pyridine-d$_5$ (product #532975) and CH₃OD (product #550574) were purchased from Sigma-Aldrich.

Example 4: Sodium (1E,3E)-5-oxopenta-1,3-dien-1-olate-1,2,3,4,5-d₅ (Compound 6)

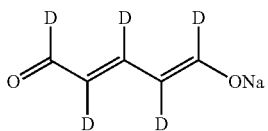

Chlorosulfonic acid (0.415 mL, 6.24 mmol, 1 eq) was added to pyridine-d₅ (1.00 mL, 12.5 mmol, 2 eq) dropwise at −15° C. with vigorous stirring to afford an equimolar mixture of C₅D₅N·SO₃ and C₅D₅N·HCl as a white solid. NaOH (1.25 g, 31.2 mmol, 5 eq) in water (5 mL) was added and the mixture was stirred at −15° C. for 1.5 h, room temperature for 1.5 h, then 40° C. for 0.5 h to afford an orange slurry. The mixture was kept at 0° C. for 5 h, and the precipitate was collected by filtration and washed with acetone. The solid was refluxed with activated charcoal (0.2 g) in methanol (20 mL) for 20 min, then activated charcoal was removed by hot filtration. The filtrate was concentrated to ~1 mL under reduced pressure, acetone (10 mL) was added to precipitate the product. The solid was collected by filtration and washed with acetone to afford 6 as a yellow solid (300 mg, 38%). HRMS (ESI-TOF) m/z: [M]⁻ calcd. for C₅D₅O₂³¹ 102.0609, found 102.0600.

Example 5: Indocyanine Green-d₅ (ICG-d₅)

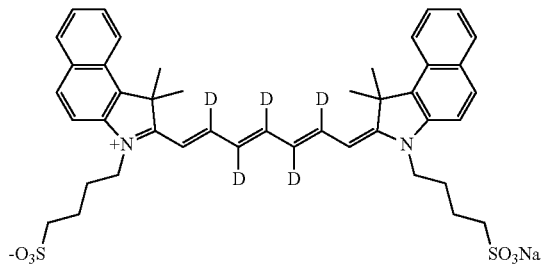

3 possible synthetic methods (Methods A-C):
i. Method A (Stacko and Klan's Method)

A mixture of pyridine-d₅ Zincke salt 2 (100 mg, 237 µmol, 1 eq) and 4-bromoaniline (48.9 mg, 284 µmol, 1.2 eq) in methanol (10 mL) was stirred at room temperature for 15 min, then indolium 3 (245 mg, 710 µmol, 3 eq) and sodium acetate (117 mg, 1.42 mmol, 6 eq) were added. The mixture was stirred at room temperature under argon atmosphere in the dark for 36 h. The reaction was directly purified by reverse phase column chromatography (55-65% MeOH in H₂O) to afford ICG-d₅ as a green solid (100 mg, 54%).

ii. Method B (Through In-Situ Generated Zincke's Glutaconaldehyde Dianil-d₅)

A mixture of pyridine-d₅ Zincke salt 2 (500 mg, 1.18 mmol, 1 eq) and aniline (0.270 mL, 2.96 mmol, 2.5 eq) in ethanol (20 mL) was stirred at room temperature for 12 h, then indolium 3 (900 mg, 2.60 mmol, 2.2 eq), sodium acetate (291 mg, 3.55 mmol, 3 eq) and acetic anhydride (10 mL) were added. The mixture was stirred at 80° C. under argon atmosphere in the dark for 5 h. The solvent was removed under reduced pressure, the residue was suspended in acetone (20 mL) and filtered. The solid was purified by reverse phase column chromatography (55-65% MeOH in H₂O) to afford ICG-d₅ as a green solid (550 mg, 60%).

iii. Method C (Through Becher's Glutaconaldehyde-d₅)

A mixture of 6 (50 mg, 400 µmol, 1 eq), indolium 3 (304 mg, 897 µmol, 2.2 eq) and sodium acetate (65.6 mg, 799 µmol, 2 eq) in acetic anhydride (10 mL) was stirred at 100° C. under argon atmosphere in the dark for 2 h. The solvent was removed under reduced pressure, the residue was suspended in acetone (10 mL) and filtered. The solid was purified by reverse phase column chromatography (55-65% MeOH in H₂O) to afford ICG-d₅ as a green solid (220 mg, 71%). To increase the dissolving speed of ICG-d₅ in water, solid ICG-d₅ (100 mg) was dissolved in methanol (5 mL) then water (10 mL) was added. Methanol was removed under reduced pressure at 45° C. to give a slurry and it was lyophilized to afford ICG-d₅ powder.

¹H NMR (500 MHz, methanol-d₄, 25° C.) δ(ppm): 8.22 (d, J=8.5 Hz, 2H), 8.02-7.94 (m, 4H), 7.65-7.58 (m, 4H), 7.46 (dd, J=8.5, 8.5 Hz, 2H), 6.37 (br s, 2H), 4.24 (t, J=7.3 Hz, 4H), 2.91 (t, J=7.0 Hz, 4H), 2.07-1.94 (m, 20H). HRMS (ESI-TOF) m/z: [M]⁻ calcd for C₄₃H₄₂D5N₂O₆S₂⁻ 756.3195, found 756.3193.

Example 6: Indocyanine Green-d₇ (ICG-d₇)

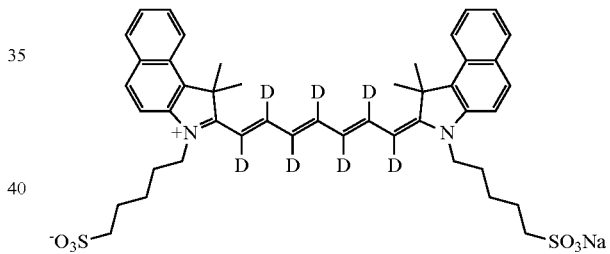

The indolium 3 (245 mg, 710 µmol, 3 eq) was stirred in CH₃OD (5 mL) for 8 h at room temperature. A mixture of pyridine-d₅ Zincke salt 2 (100 mg, 237 µmol, 1 eq) and 4-bromoaniline (48.9 mg, 284 µmol, 1.2 eq) in CH₃OD (10 mL) was stirred at room temperature for 15 min, then the indolium solution in CH₃OD and sodium acetate (117 mg, 1.42 mmol, 6 eq) were added. The mixture was stirred at room temperature under argon atmosphere in the dark for 36 h. The reaction was directly purified by reverse phase column chromatography (55-65% MeOH in H₂O) to afford ICG-d₇ as a green solid (110 mg, 59%). To increase the dissolving speed of ICG-d₇ in water, solid ICG-d₇ (110 mg) was dissolved in methanol (5 mL) then water (10 mL) was added. Methanol was removed under reduced pressure at 45° C. to give a slurry. The slurry was lyophilized to afford ICG-d₇ as a powder. ¹H NMR (500 MHz, methanol-d₄, 25° C.) δ(ppm): 8.22 (d, J=8.6 Hz, 2H), 8.02-7.95 (m, 4H), 7.65-7.59 (m, 4H), 7.46 (dd, J=7.5, 7.5 Hz, 2H), 4.24 (t, J=7.9 Hz, 4H), 2.91 (t, J=7.1 Hz, 4H), 2.07-1.94 (m, 20H). HRMS (ESI-TOF) m/z: [M]⁻ calcd for C₄₃H₄₀D₇N₂O S₂⁻ 758.3320, found 758.3344.

Example 7: Indocyanine Green-d$_4$ (ICG-d$_4$)

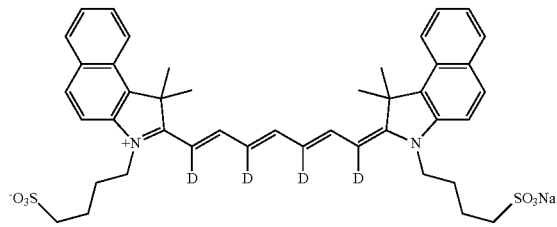

Prepared according to the procedure reported by M. Lipowska, S. E. Patterson, G. Patonay, L. Strekowski, *J. Heterocycl. Chem.* 1993, 30, 1177-1180. Indocyanine green (50 mg, 64.5 μmol, 1 eq) was dissolved in CH$_3$OD (6.45 mL, 10 mM), then deuterium chloride (35 wt % in D$_2$O, 7.97 μL, 1.5 eq) was added. The mixture was stirred vigorously at room temperature for 24 h and then diethyl ether (10 mL) was added. The solid was collected by filtration and dried to afford ICG-d$_4$ as a green powder (50 mg, 100%). $^1$H NMR (500 MHz, methanol-d$_4$, 25° C.) δ(ppm): 8.22 (d, J=8.6 Hz, 2H), 8.02 (br s, 2H), 8.02-7.95 (m, 4H), 7.63-7.50 (m, 5H), 7.46 (dd, J=7.5, 7.5 Hz, 2H), 4.24 (t, J=7.9 Hz, 4H), 2.91 (t, J=7.0 Hz, 4H), 2.07-1.94 (m, 20H).

Example 8 2,3,5,6-d$_4$-Pyridine (Pyridine-d$_4$)

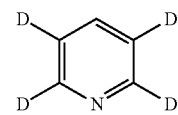

To a suspension of 2,3,5,6-tetrachloropyridine (1.0 g, 4.6 mmol) and K$_2$CO$_3$ (2.6 g, 19 mmol, 4 eq.) in THF (5 mL) and D$_2$O (5 mL) in a 30 mL Parr reactor is added 5% Pd/C (100 mg, 10 wt %). The reactor is sealed, purged with N$_2$, then pressurized with D$_2$ (8 bar). The reaction mixture is then stirred at room temperature for 4 hours. The pressure is released, and the suspension is filtered through Celite and washed with diethyl ether (20 mL). The filtrate is dried over MgSO$_4$ then acidified with HCl (2 M in diethyl ether, 4 mL). The resulting suspension is decanted to leave an oily residue which solidifies under a stream of nitrogen. This solid is dissolved in methanol-d$_4$ (4 mL) and passed through a plug of basic alumina to give a solution of 2,3,5,6-d$_4$-pyridine (0.16 M in methanol-d$_4$); $^1$H NMR (400 MHz, CDCl$_3$) δ (ppm): 7.85 (s, 1H); $^{13}$C NMR (101 MHz, CDCl$_3$) δ (ppm) 149.4 (t, J=27.2 Hz), 138.2 (s), 125.1 (t, J=25.3 Hz); MS (ESI) m/z 84 [(M+H)$^+$, 100]. The concentration is determined by quantitative NMR with potassium phthalate monobasic as an internal standard. (Philip Norcott, Michael J. Burns, Peter J. Rayner, Ryan E. Mewis and Simon B. Duckett, *Magnetic Resonance in Chemistry*, 2018, 56, 663.)

Example 9: Oxidative Dimer of Indocyanine Green (ICG) (Oxidative Dimer 1)

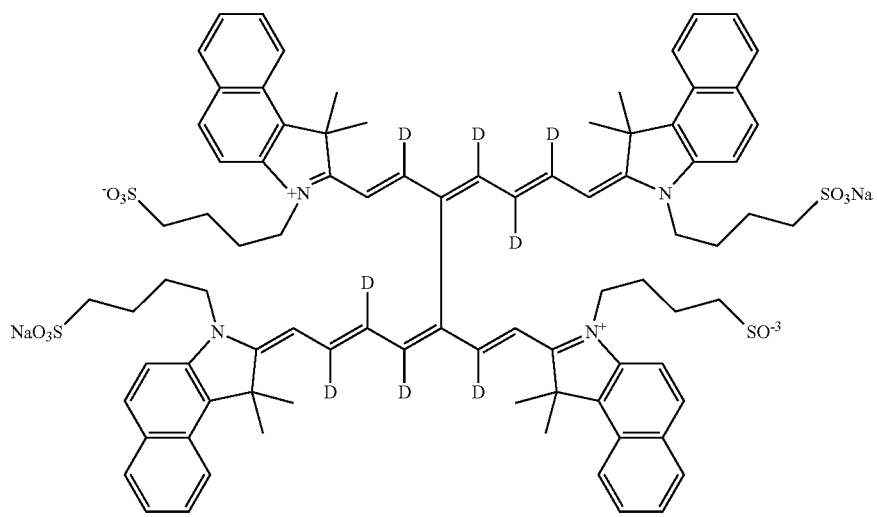

ICG oxidative dimer 1. $^1$H NMR peaks for ICG and its oxidative dimer 1 have previously been assigned based on extensive data acquired by multiple 2D NMR methods. A solution of ICG (300 mg, 387 μmol) in water (300 mL) was stirred at room temperature under low photon intensity conditions (exposed to laboratory lights during preparation then stored as capped vials in dark) for 1 week. Oxidative dimer 1 was isolated by reverse phase column chromatography (60% MeOH in $H_2O$) as a green solid (230 mg, 77%). $^1$H NMR (500 MHz, methanol-$d_4$, 25° C.) δ(ppm): 8.35-8.24 (m, 8H), 8.04 (d, J=13.3 Hz, 2H), 8.01-7.90 (m, 8H), 7.68-7.59 (m, 6H), 7.53-7.41 (m, 6H), 6.54-6.42 (m, 4H), 5.88 (d, J=13.7 Hz, 2H), 4.23 (t, J=7.5 Hz, 4H), 4.12-4.02 (m, 2H), 4.00-3.91 (m, 2H), 2.86-2.75 (m, 8H), 2.12 (s, 12H), 2.06 (s, 6H), 2.04 (s, 6H), 1.99-1.77 (m, 16H). HRMS (ESI-TOF) m/z: [M]$^{2-}$ calcd for $C_{86}H_{82}N_4OS^{2-}$ 750.7842, found 750.7802.

Example 10: Oxidative Dimer of ICG-$d_5$ (Oxidative Dimer 1-$d_8$)

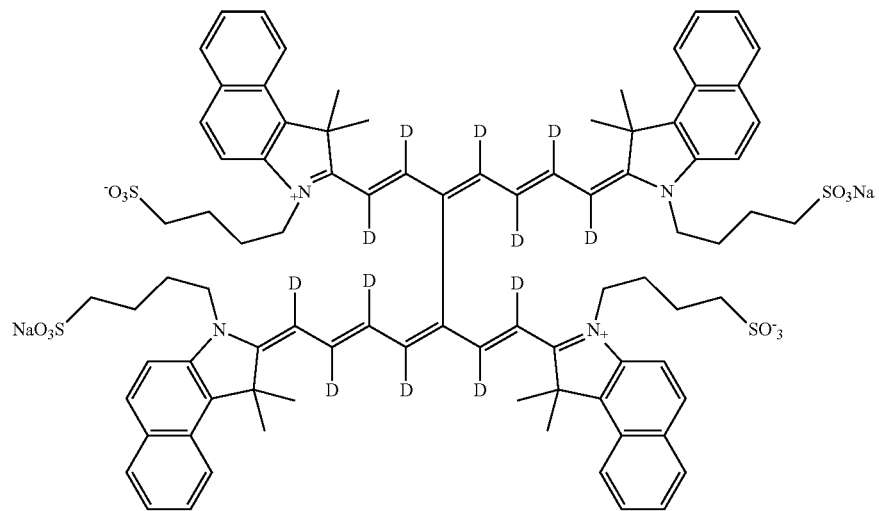

ICG-d₅ oxidative dimer 1-d₈. A solution of ICG-d₅ (50 mg, 61.4 µmol) in water (200 mL) was stirred at room temperature under low photon intensity conditions (exposed to laboratory lights during preparation then stored as capped vials in dark) for 1 week. Oxidative dimer 1-d₈ was isolated by reverse phase column chromatography (60% MeOH in H₂O) as a green solid (35 mg, 70%). ¹H NMR (500 MHz, methanol-d₄, 25° C.) δ(ppm): 8.31-8.24 (m, 4H), 8.01-7.96 (m, 4H), 7.94-7.91 (m, 3H), 7.68-7.59 (m, 6H), 7.53-7.47 (m, 4H), 7.43 (dd, J=7.6, 7.6 Hz, 2H), 6.48 (br s, 2H), 5.87 (br s, 2H), 4.22 (t, J=7.4 Hz, 4H), 4.12-4.02 (m, 2H), 4.00-3.91 (m, 2H), 2.81 (t, J=7.4 Hz, 4H), 2.78 (t, J=7.4 Hz, 4H), 2.12 (s, 12H), 2.06 (s, 6H), 2.04 (s, 6H), 2.00-1.77 (m, 16H). HRMS (ESI-TOF) m/z: [M]²⁻ calcd for $C_{86}H_{84}D_8N_4O_{12}S_4{}^{2-}$ 754.3054, found 754.3065.

Example 11: Oxidative Dimer of ICG-d₇ (Oxidative Dimer 1-d₁₂)

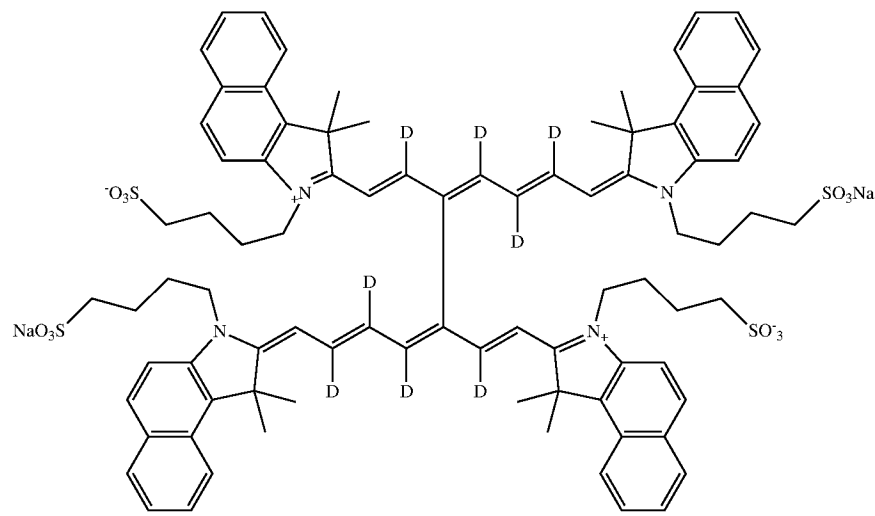

ICG-d₇ oxidative dimer 1-d₁₂. A solution of ICG-d₇ (20 mg, 25.6 µmol) in water (100 mL) was stirred at room temperature under low photon intensity conditions (exposed to laboratory lights during preparation then stored as capped vials in dark) for 1 week. Oxidative dimer 1-d₁₂ was isolated by reverse phase column chromatography (60% MeOH in H₂O) as a green solid (12 mg, 60%). ¹H NMR (500 MHz, methanol-d₄, 25° C.) δ(ppm): 8.31-8.24 (m, 4H), 8.01-7.95 (m, 4H), 7.95-7.90 (m, 2H), 7.68-7.58 (m, 6H), 7.53-7.46 (m, 4H), 7.43 (dd, J=7.6, 7.6 Hz, 2H), 4.22 (t, J=7.2 Hz, 4H), 4.12-4.03 (m, 1H), 4.00-3.91 (m, 2H), 2.81 (t, J=7.4 Hz, 4H), 2.79 (t, J=7.4 Hz, 4H), 2.11 (s, 12H), 2.05 (s, 6H), 2.03 (s, 6H), 1.98-1.79 (m, 16H). HRMS (ESI-TOF) m/z: [M]²⁻ calcd for $C_{86}H_{80}D_{12}N_4O_{12}S_4{}^{2-}$ 756.3179, found 756.3171.

Example 12: Fluorescence Quantum Yield Measurements

Absolute quantum yields of ICG, ICG-d₅, and ICG-d₇ were measured on a Horiba Fluoromax Plus spectrometer with an integrating sphere. Samples were excited at 730 nm with optical density≤0.05. First, photons were recorded with an integrating sphere after the excitation of a blank solvent reference, then the reference was replaced by a sample solution, and the spectrum (720-875 nm) was acquired again. The quantum yield was calculated by the equation below:

$$\Phi_F = \frac{P_{em}}{P_{abs}} = \frac{\int_{750}^{875}(F_{sample}-F_{blank})d\lambda}{\int_{720}^{740}(E_{blank}-E_{sample})d\lambda}$$

where P is the number of photons, F is the fluorescence intensity and E is the intensity at the excitation wavelength. Experiments were conducted in triplicate, with the reported absolute quantum yields corresponding to the mean value±standard deviation.

For 1, the fluorescence quantum yield was measured relative to ICG in DMSO or FBS. The concentrations of ICG and 1 were adjusted to an absorption value of 0.08 at 720 nm. The fluorescence spectrum of each solution was obtained with excitation at 720 nm, and the integrated area was used to calculate the quantum yield according to the following equation:

$$\Phi_{sample} = \Phi_{ref} \times \frac{\eta_{sample}^2 I_{sample} A_{sample}}{\eta_{ref}^2 I_{ref} A_{ref}}$$

where η is the refractive index of the solvent, I is the integrated fluorescence intensity, and A is the absorbance at a chosen wavelength. The estimated error for this method is ±15%.

Example 13: Aqueous Stability Studies

The relative stabilities of aqueous ICG, ICG-$d_5$, and ICG-$d_7$ were assessed under two different sets of conditions. The first set of studies were high photon intensity photobleaching experiments. These high photon intensity photobleaching experiments mimicked clinical/diagnostic imaging conditions that fragment the ICG, producing non-fluorescent carbonyl-containing compounds (Scheme 1, pathway A).

Scheme 1. Three distinct degradation pathways for aqueous ICG, ICG-$d_5$, or ICG-$d_7$ in the presence of air and light. Pathway (A): double bond cleavage to produce carbonyl-containing fragments. Pathway (B): truncation to produce pentamethine homologue. Pathway (C): oxidative dimerization to produce oxidative dimers 1, 1-$d_8$, or 1-$d_{12}$.

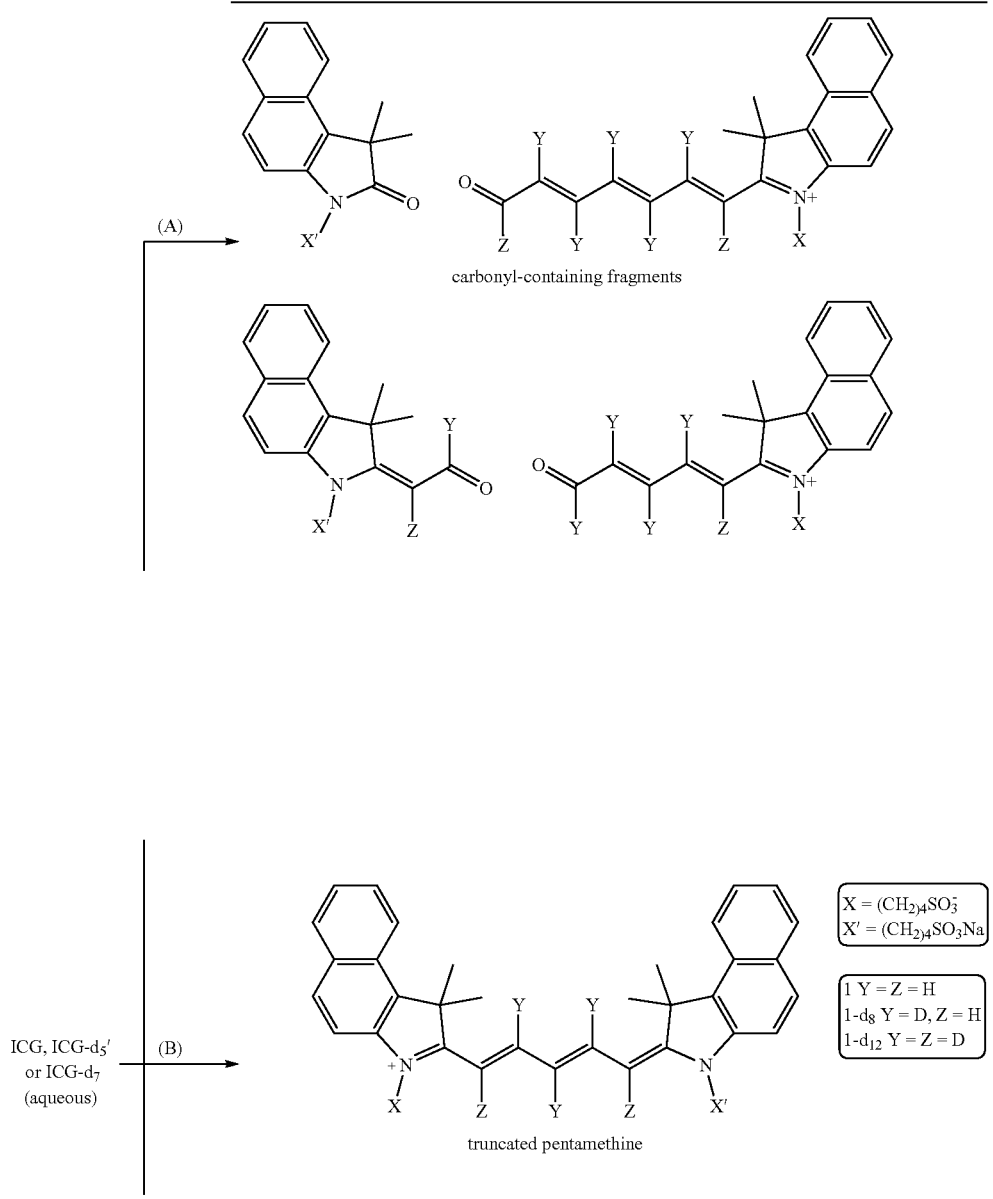

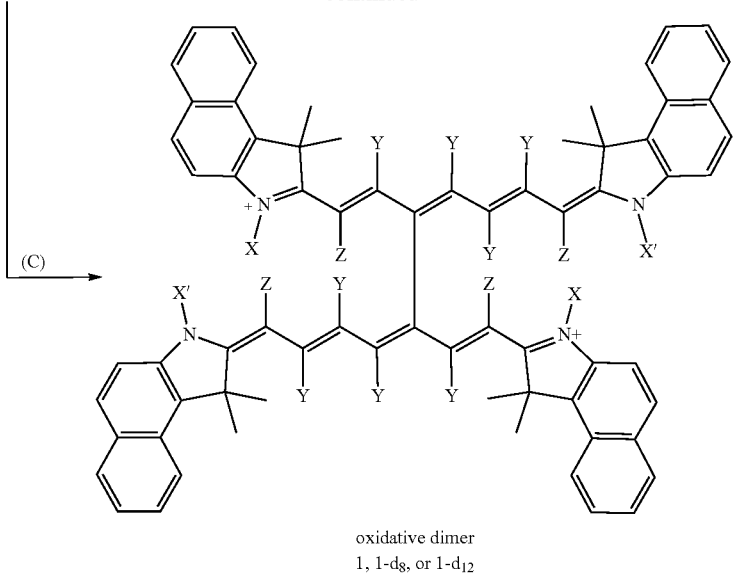

oxidative dimer
1, 1-d₈, or 1-d₁₂

Figure 2:
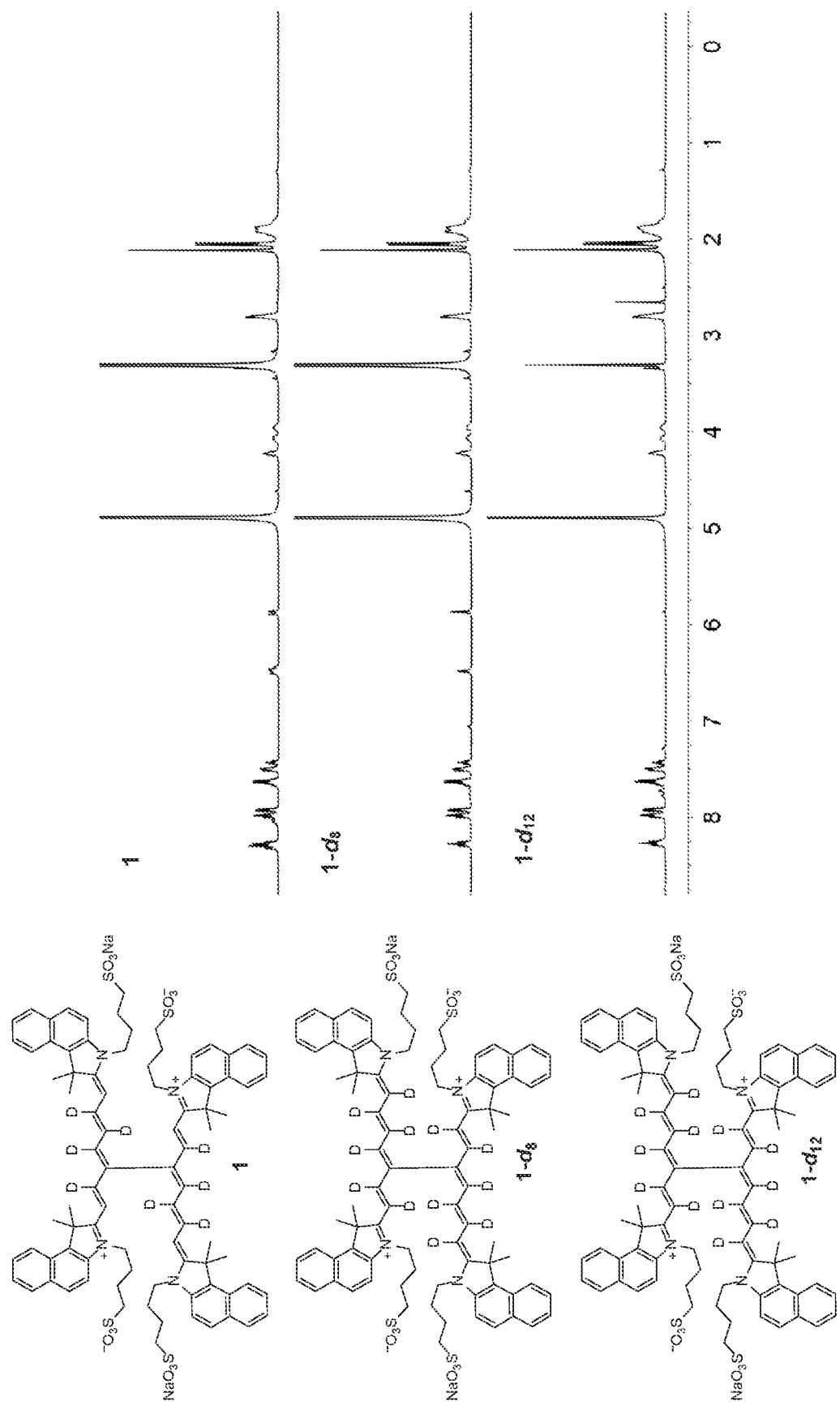
FIG. 2 shows $^1$H NMR (500 MHz, methanol-d$_4$, 25° C.) of 1 (top), 1-d$_8$ (middle) and 1-d$_{12}$ (bottom).
Figure 3A:
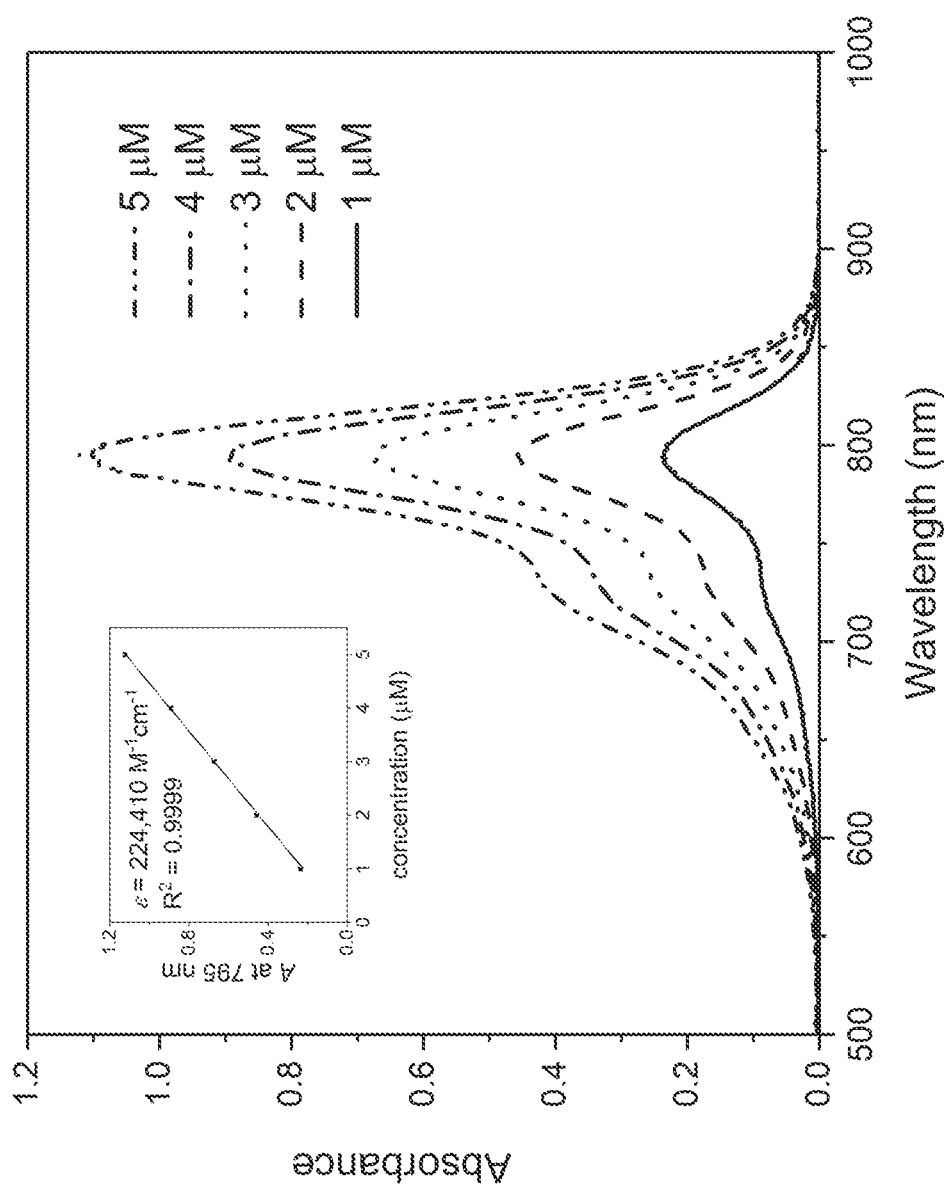
FIG. 3A shows absorption spectra of ICG in dimethyl sulfoxide (DMSO) at room temperature. Insert: Beer-Lambert fit of the absorption at 1-5 µM.
Figure 3B:
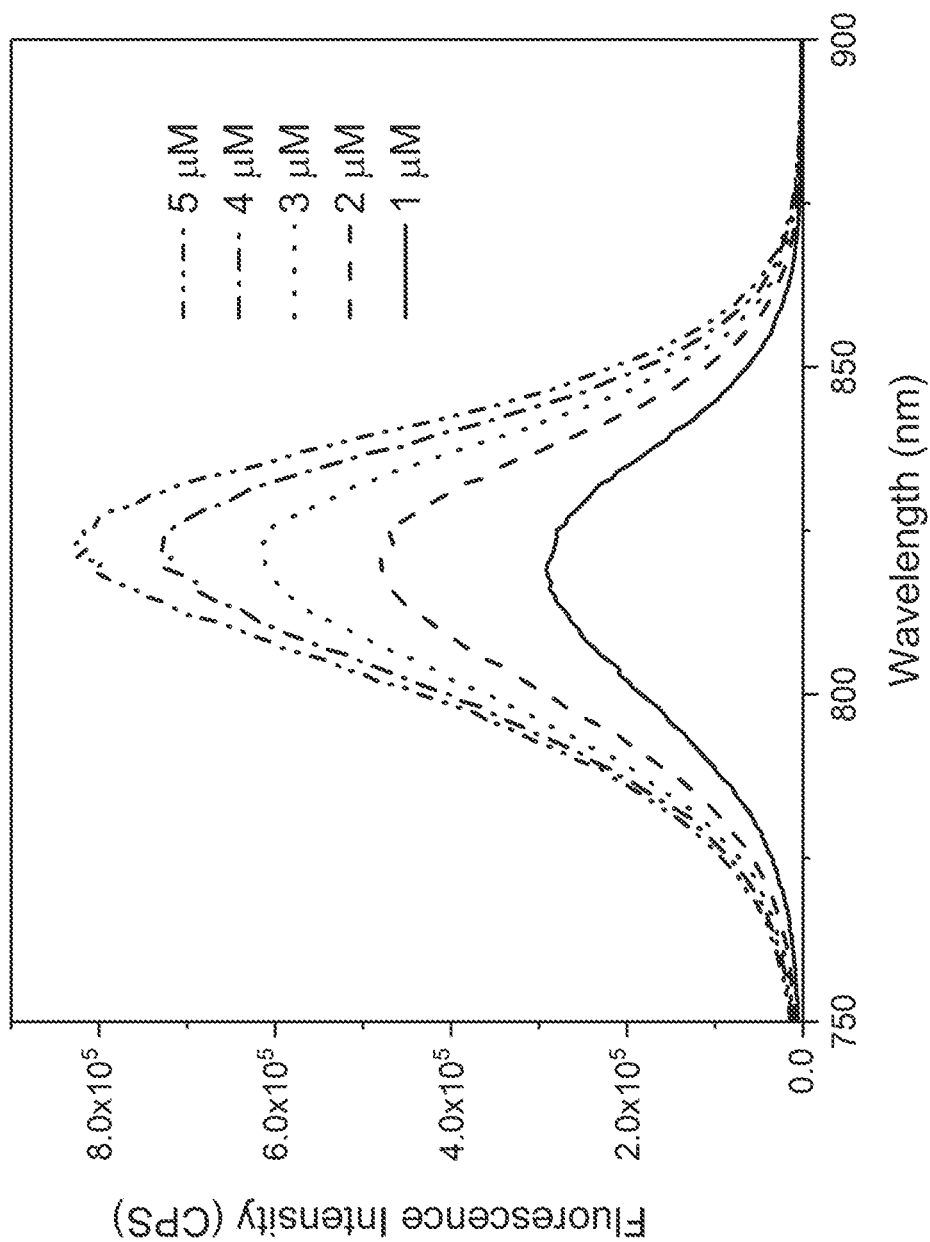
FIG. 3B shows fluorescence spectra of ICG in DMSO at room temperature. $\lambda_{ex}$=740 nm, slit width=3 nm.
Figure 4A:
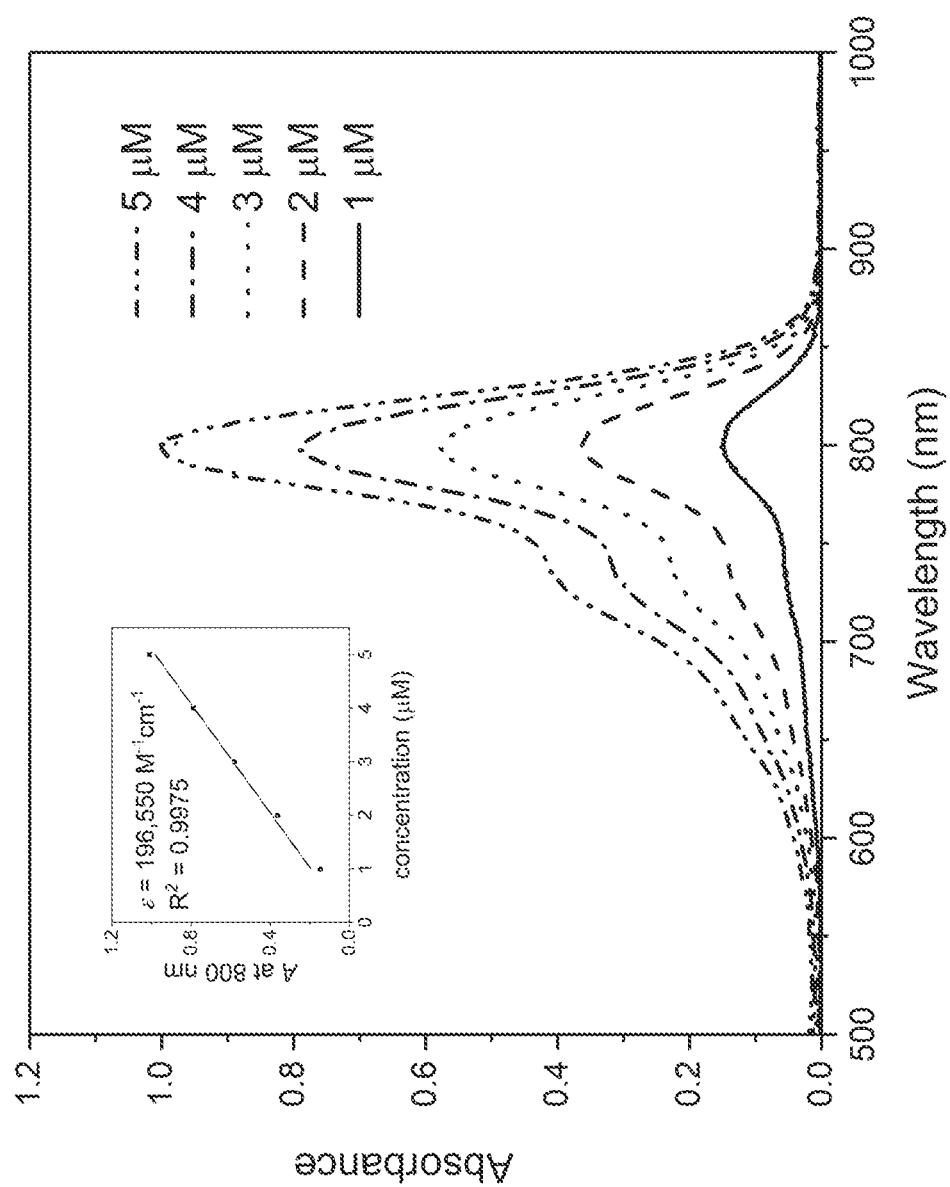
FIG. 4A shows absorption spectra of ICG in fetal bovine serum (FBS) at room temperature. Insert: Beer-Lambert fit of the absorption at 1-5 µM.
Figure 4B:
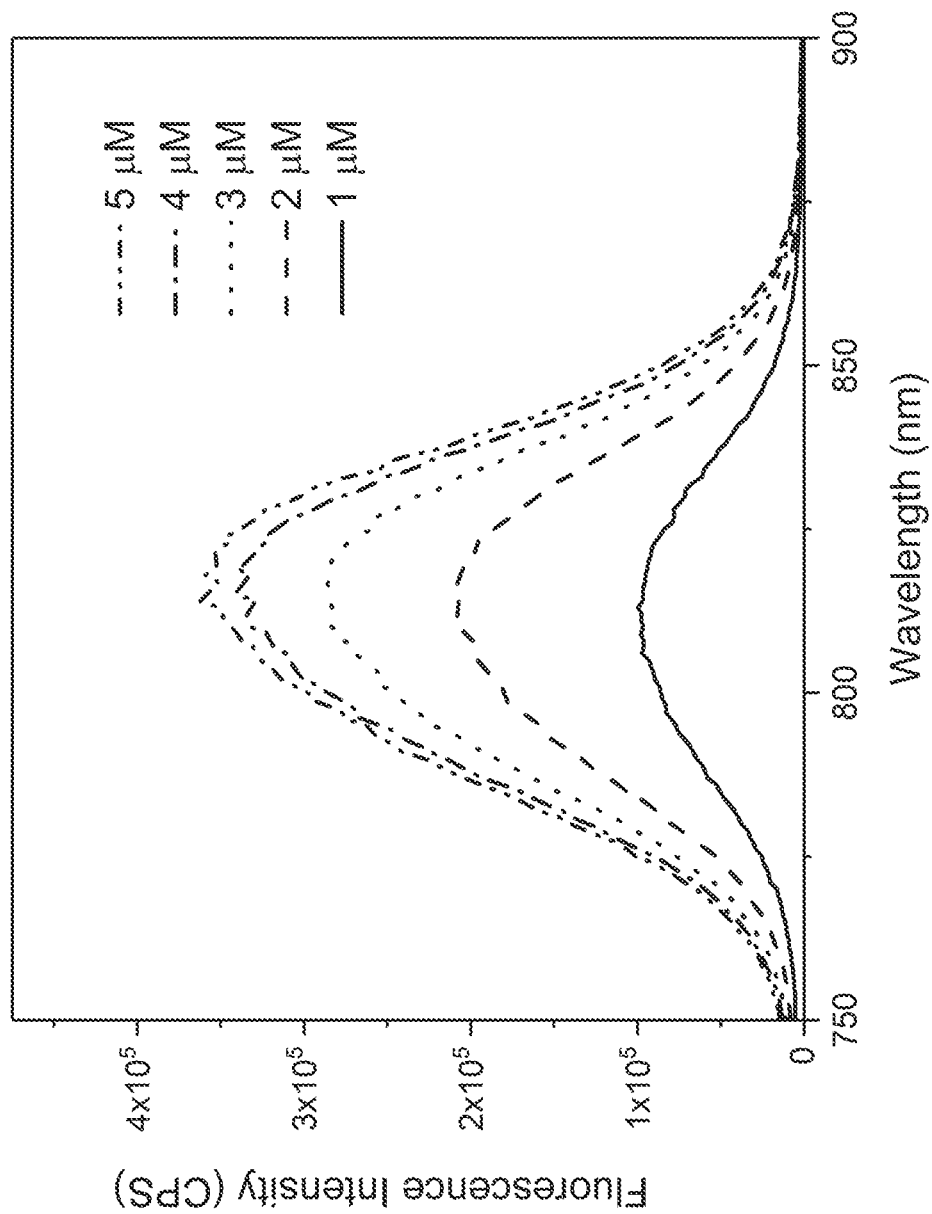
FIG. 4B shows fluorescence spectra of ICG in FBS at room temperature. $\lambda_{ex}$=740 nm, slit width=3 nm.
Figure 5A:
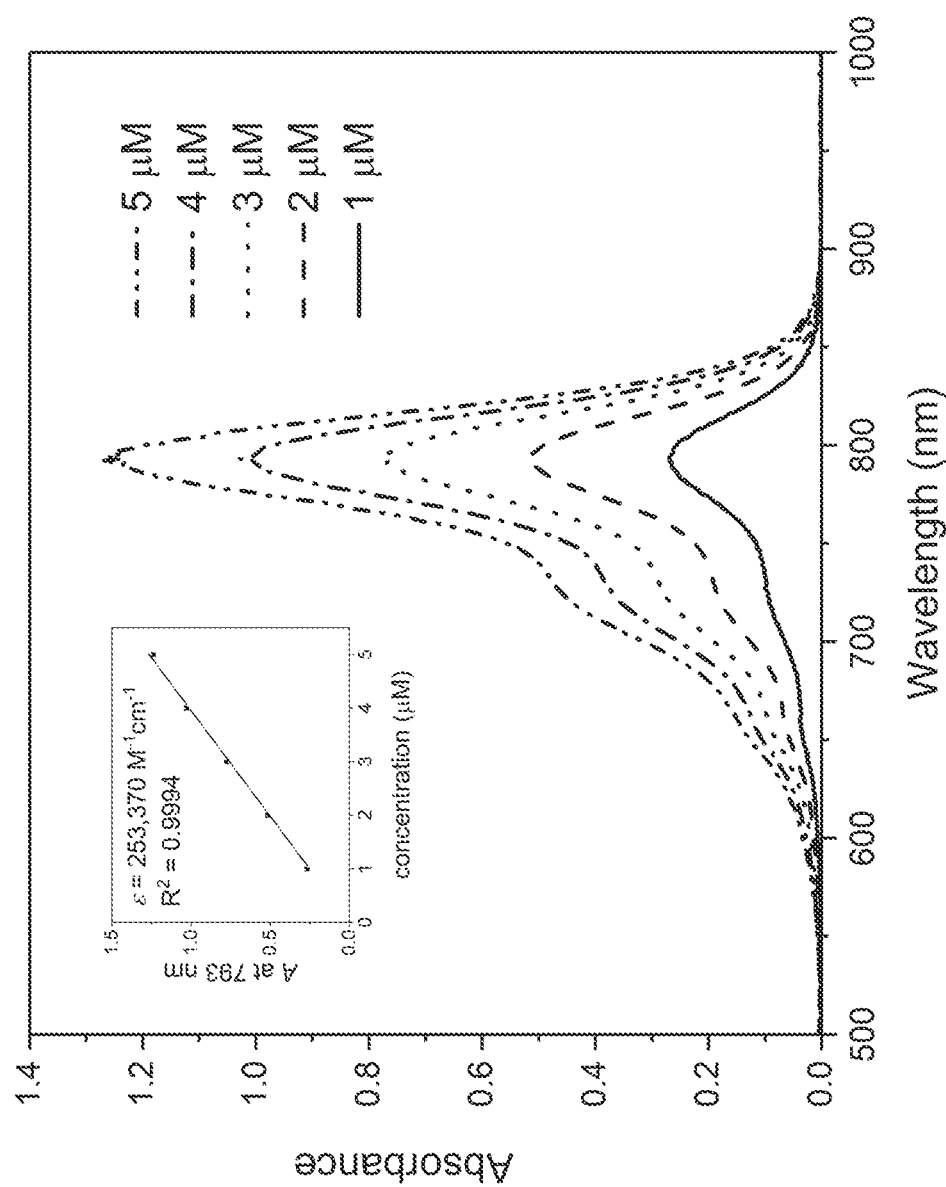
FIG. 5A shows absorption spectra of ICG-d$_5$ in DMSO at room temperature. Insert: Beer-Lambert fit of the absorption at 1-5 µM.
Figure 5B:
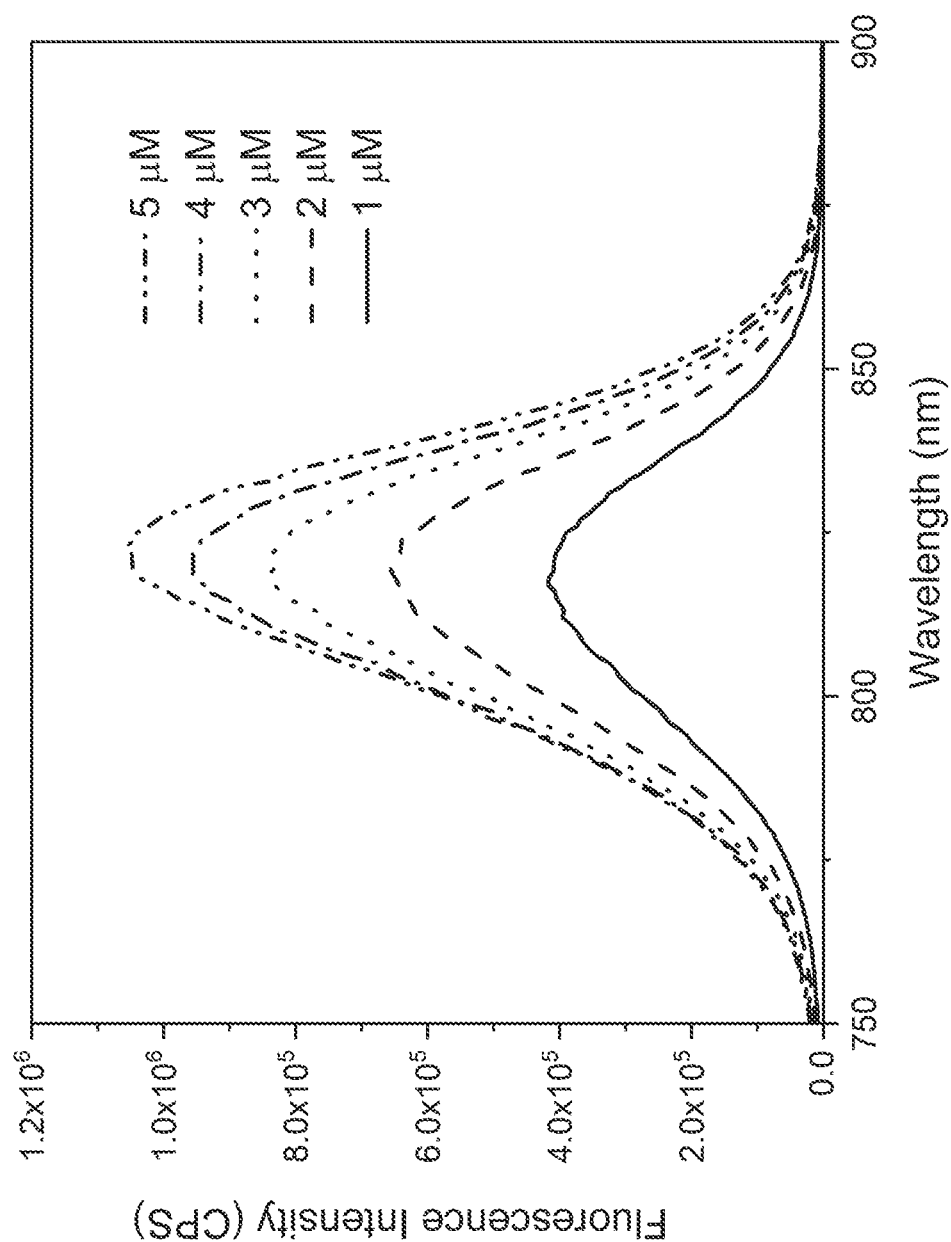
FIG. 5B shows fluorescence spectra of ICG-d$_5$ in DMSO at room temperature. $\lambda_{ex}$=740 nm, slit width=3 nm.
Figure 6A:
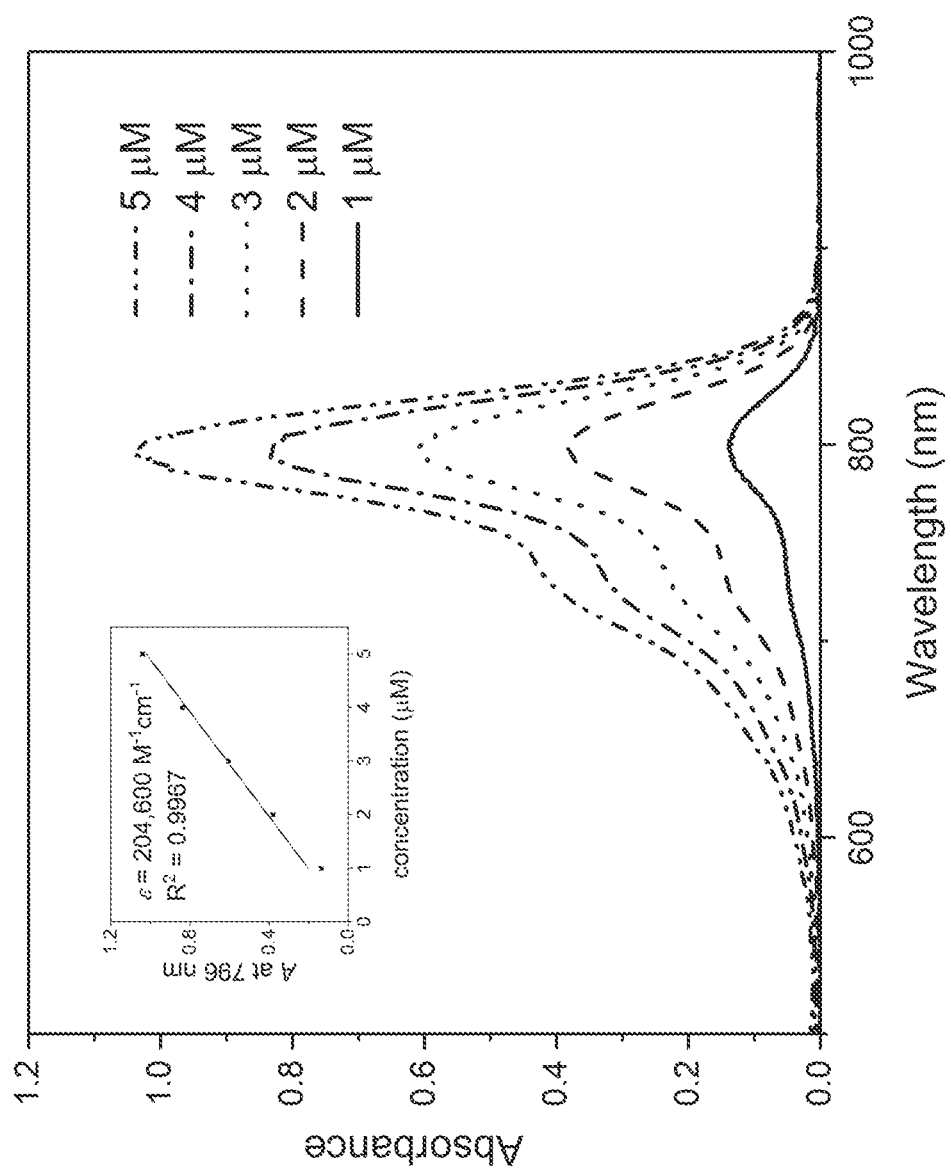
FIG. 6A shows absorption spectra of ICG-d$_5$ in FBS at room temperature. Insert: Beer-Lambert fit of the absorption at 1-5 µM.
Figure 6B:
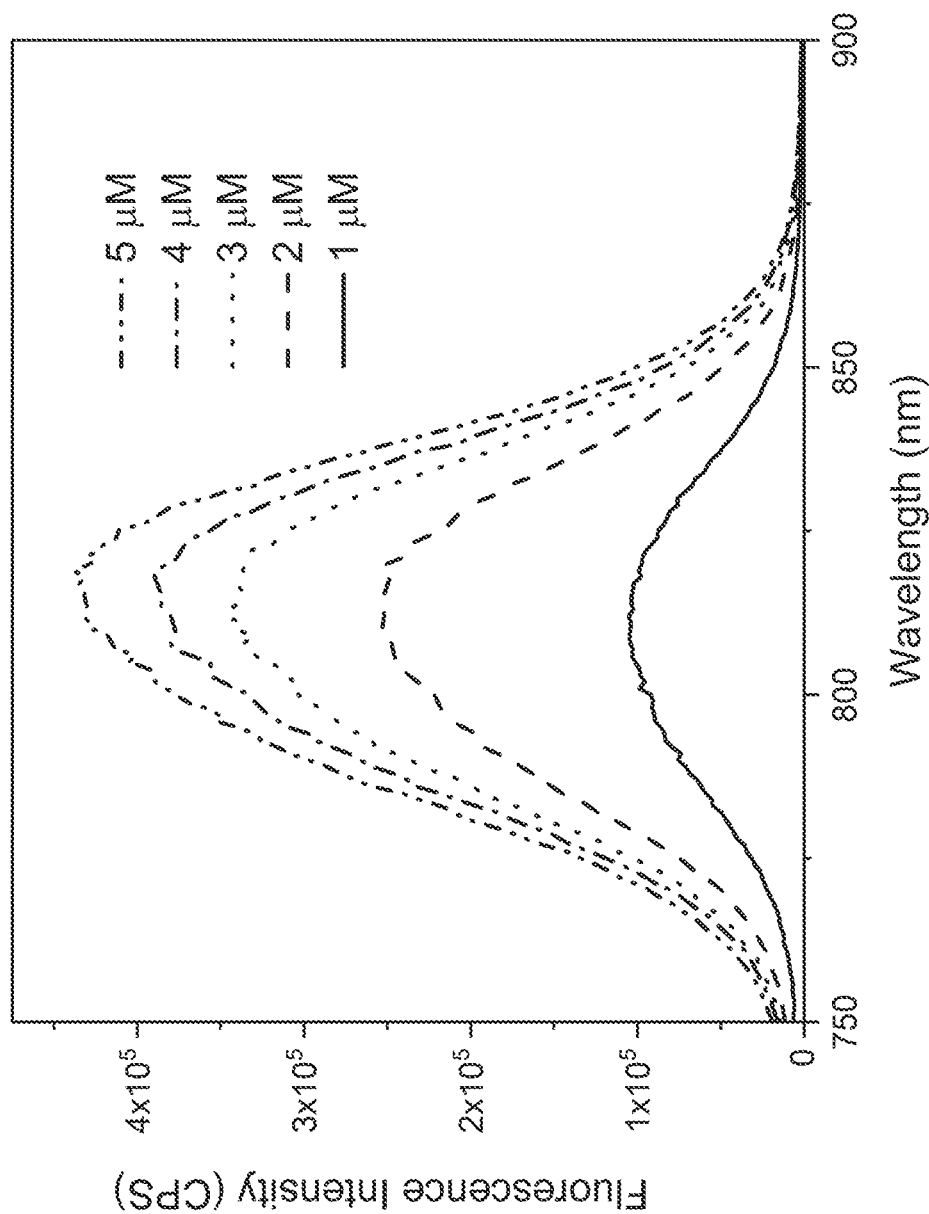
FIG. 6B shows fluorescence spectra of ICG-d$_5$ in FBS at room temperature. $\lambda_{ex}$=740 nm, slit width=3 nm.
Figure 7A:
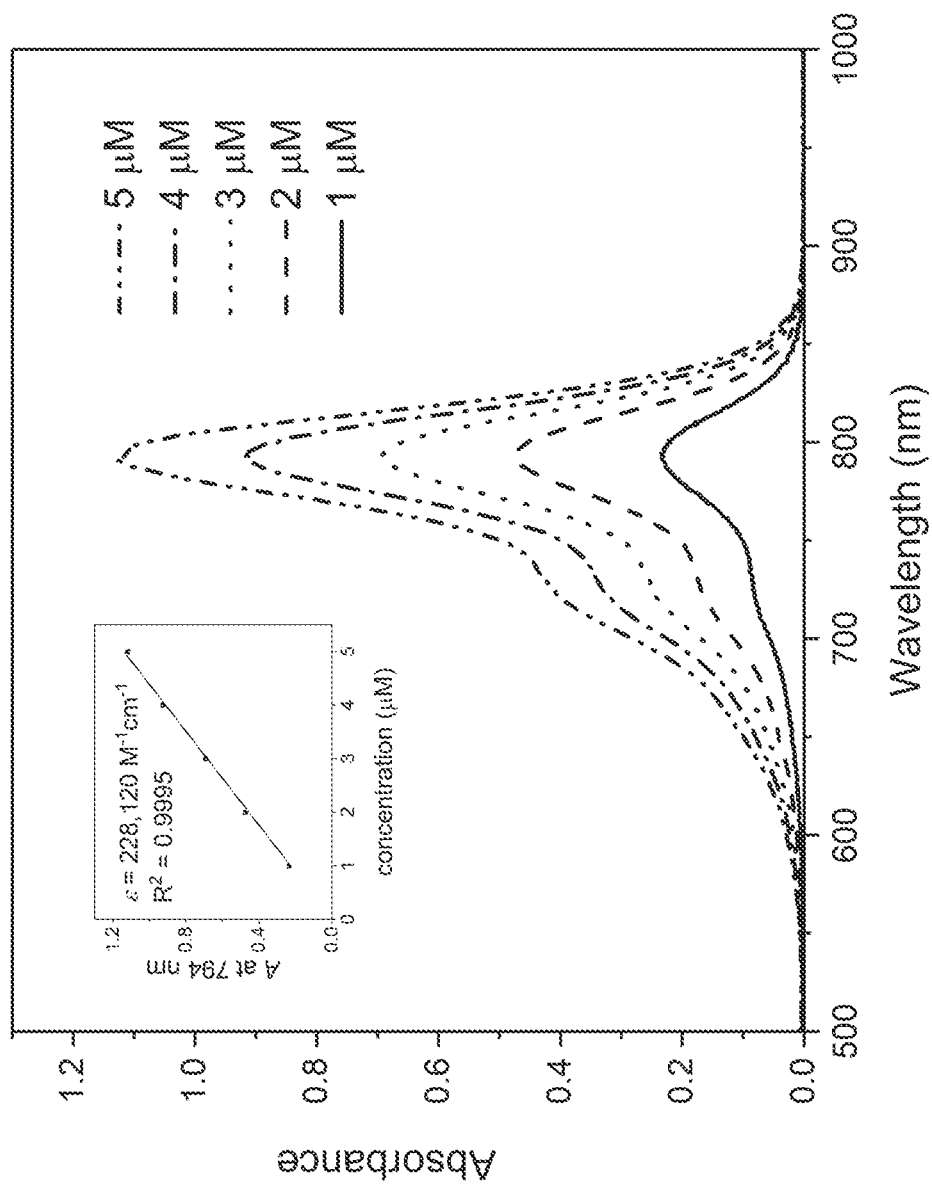
FIG. 7A shows absorption spectra of ICG-d$_7$ in DMSO at room temperature. Insert: Beer-Lambert fit of the absorption at 1-5 µM.
Figure 7B:
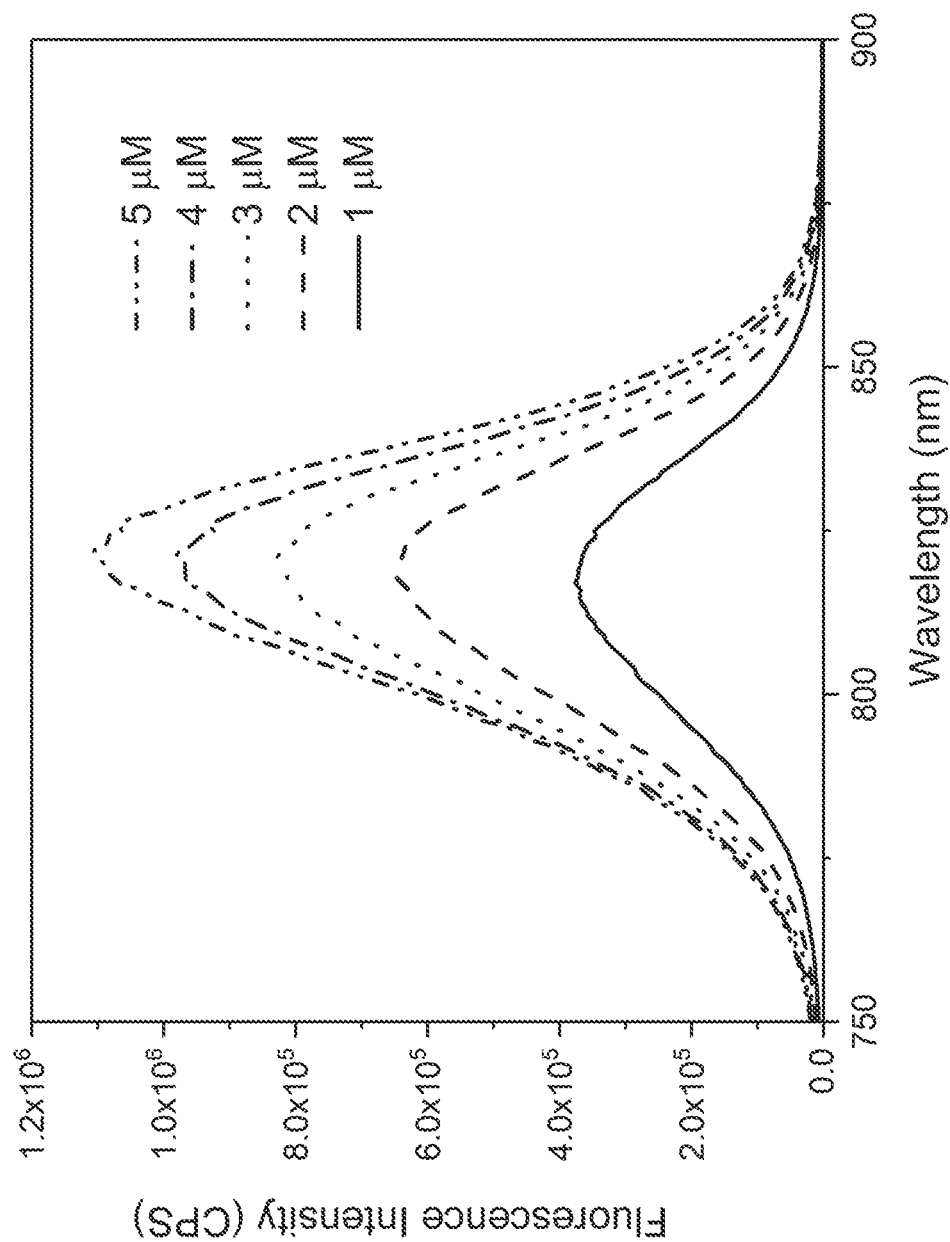
FIG. 7B shows fluorescence spectra of ICG-d$_7$ in DMSO at room temperature. $\lambda_{ex}$=740 nm, slit width=3 nm.
Figure 8A:
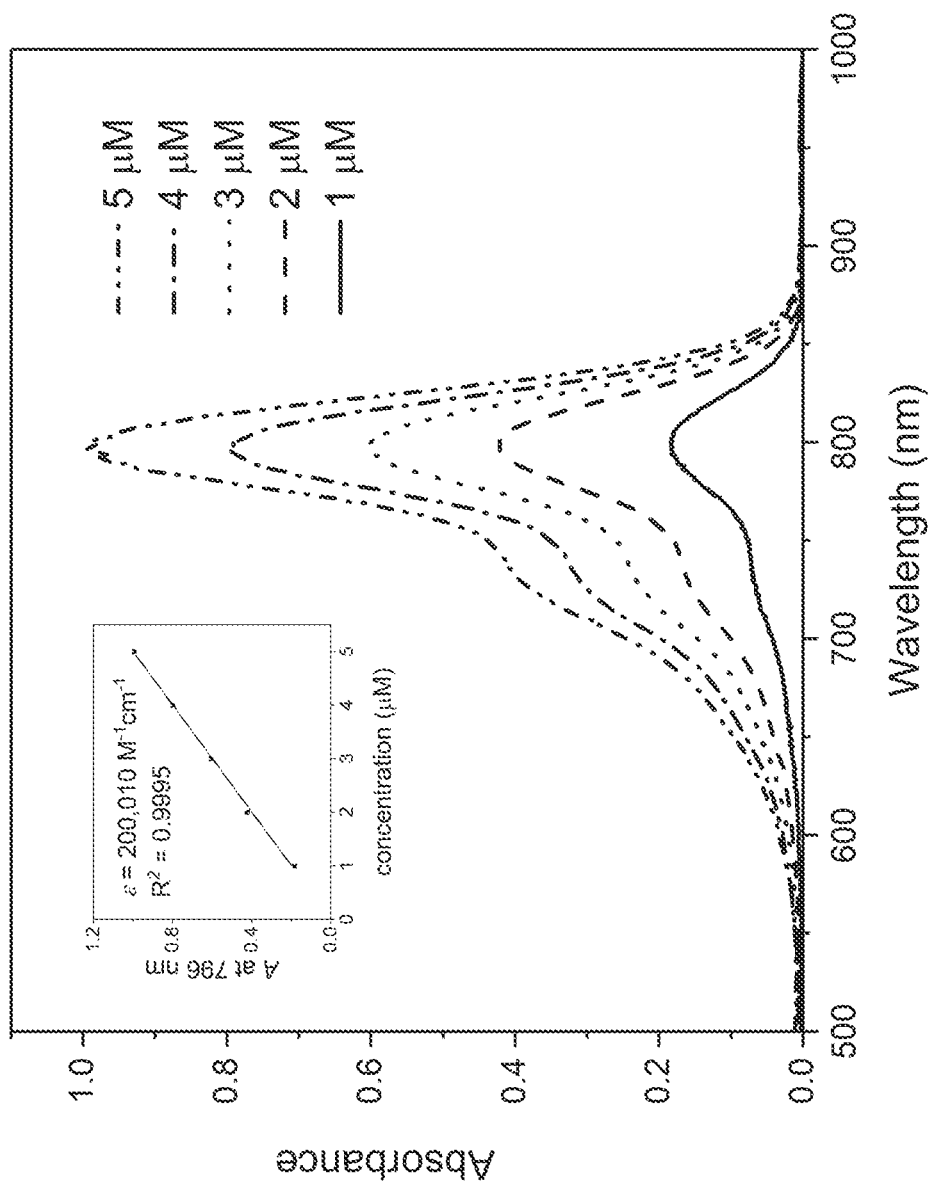
FIG. 8A shows absorption spectra of ICG-d$_7$ in FBS at room temperature. Insert: Beer-Lambert fit of the absorption at 1-5 µM.
Figure 8B:
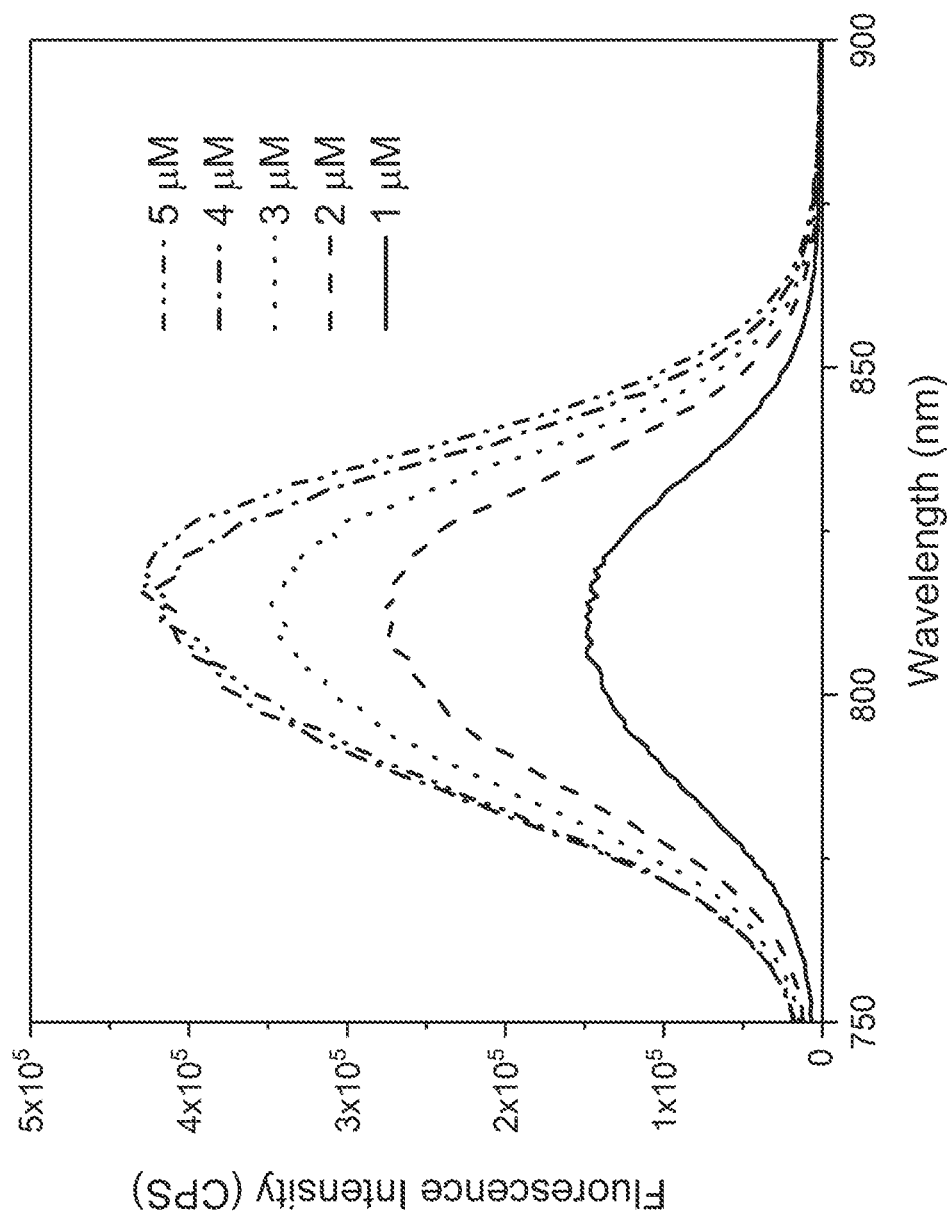
FIG. 8B shows fluorescence spectra of ICG-d$_7$ in FBS at room temperature. $\lambda_{ex}$=740 nm, slit width=3 nm.
Figure 9A:
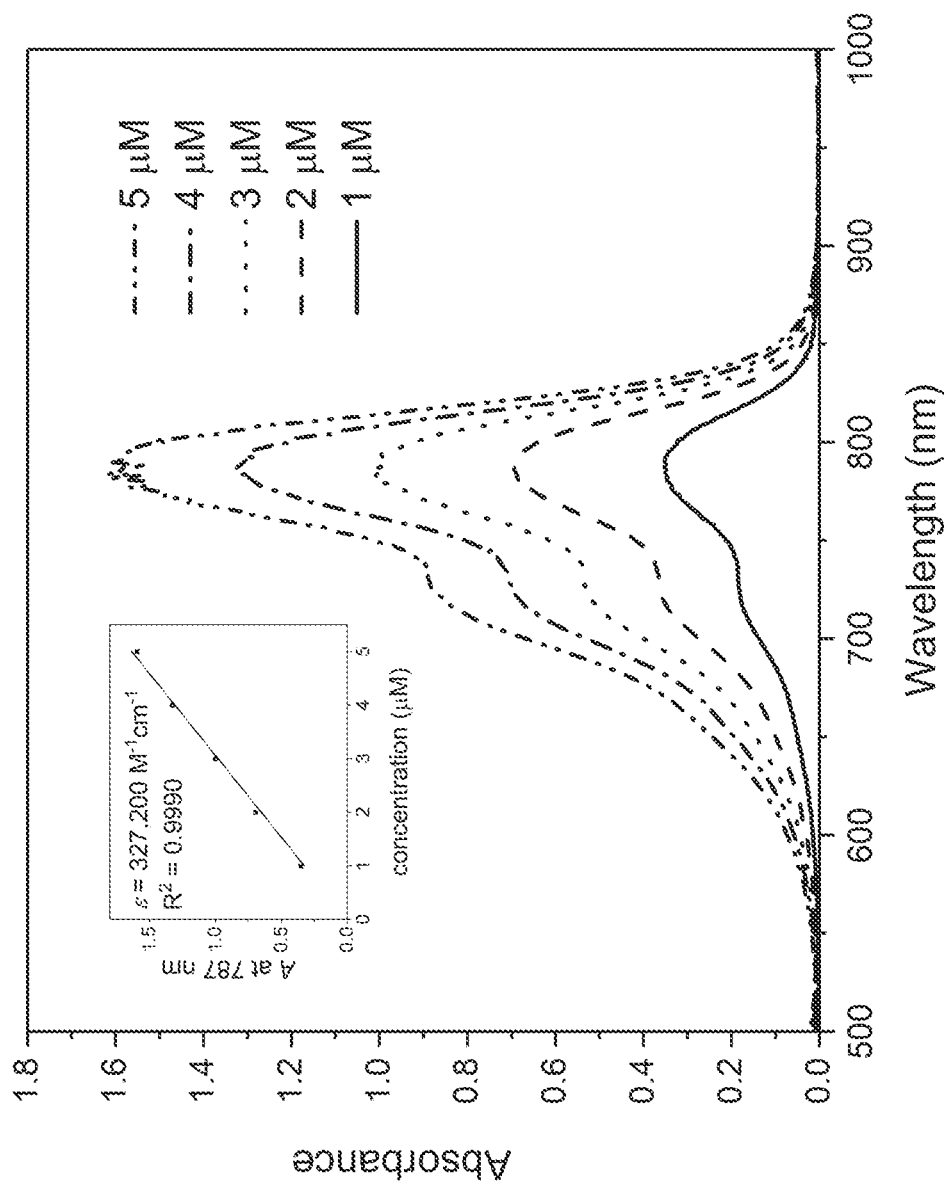
FIG. 9A shows absorption spectra of ICG's oxidative dimer ("oxidative dimer 1") in DMSO at room temperature. Insert: Beer-Lambert fit of the absorption at 1-5 µM.
Figure 9B:
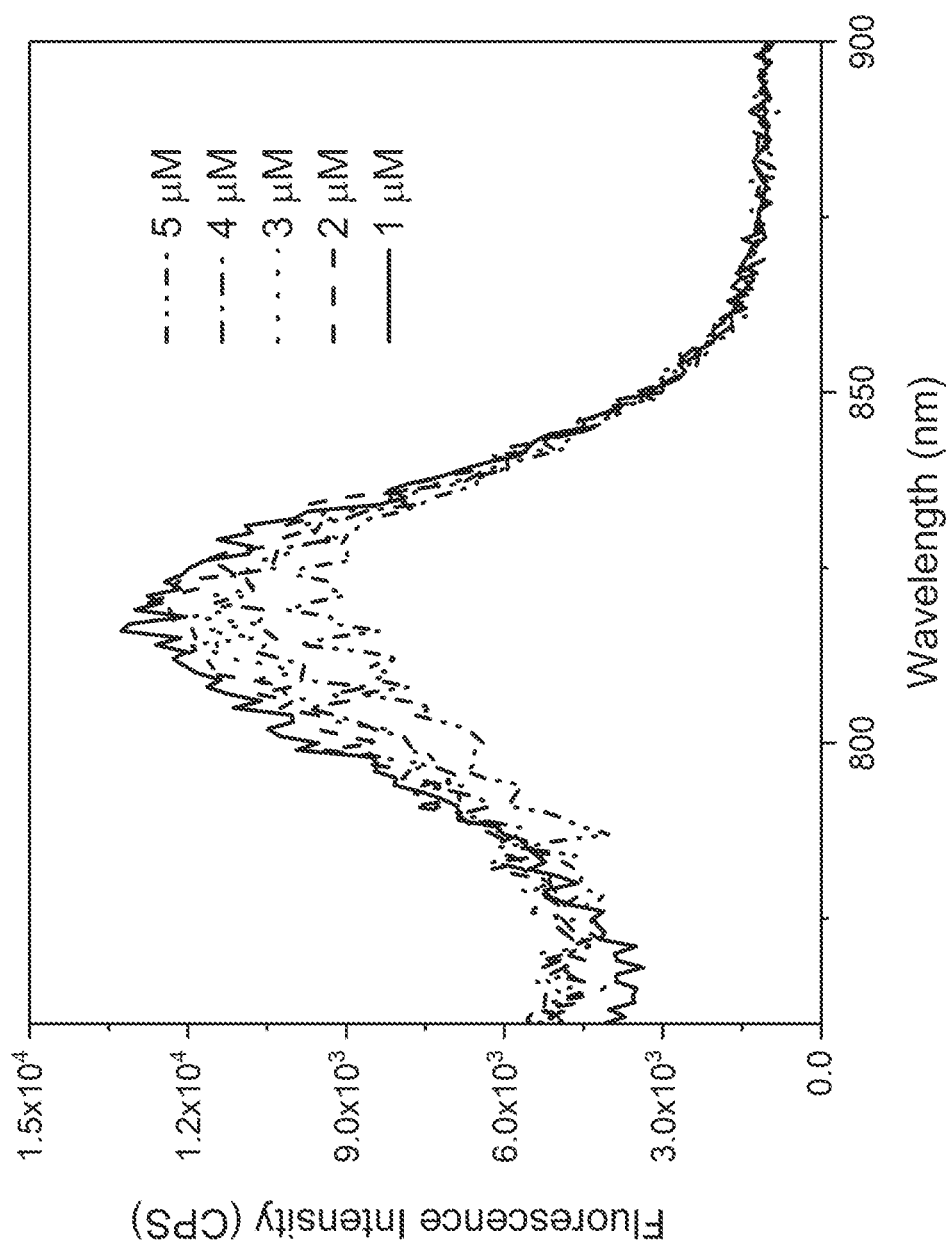
FIG. 9B shows fluorescence spectra of oxidative dimer 1 in DMSO at room temperature. $\lambda_{ex}$=740 nm, slit width=5 nm.
Figure 10A:
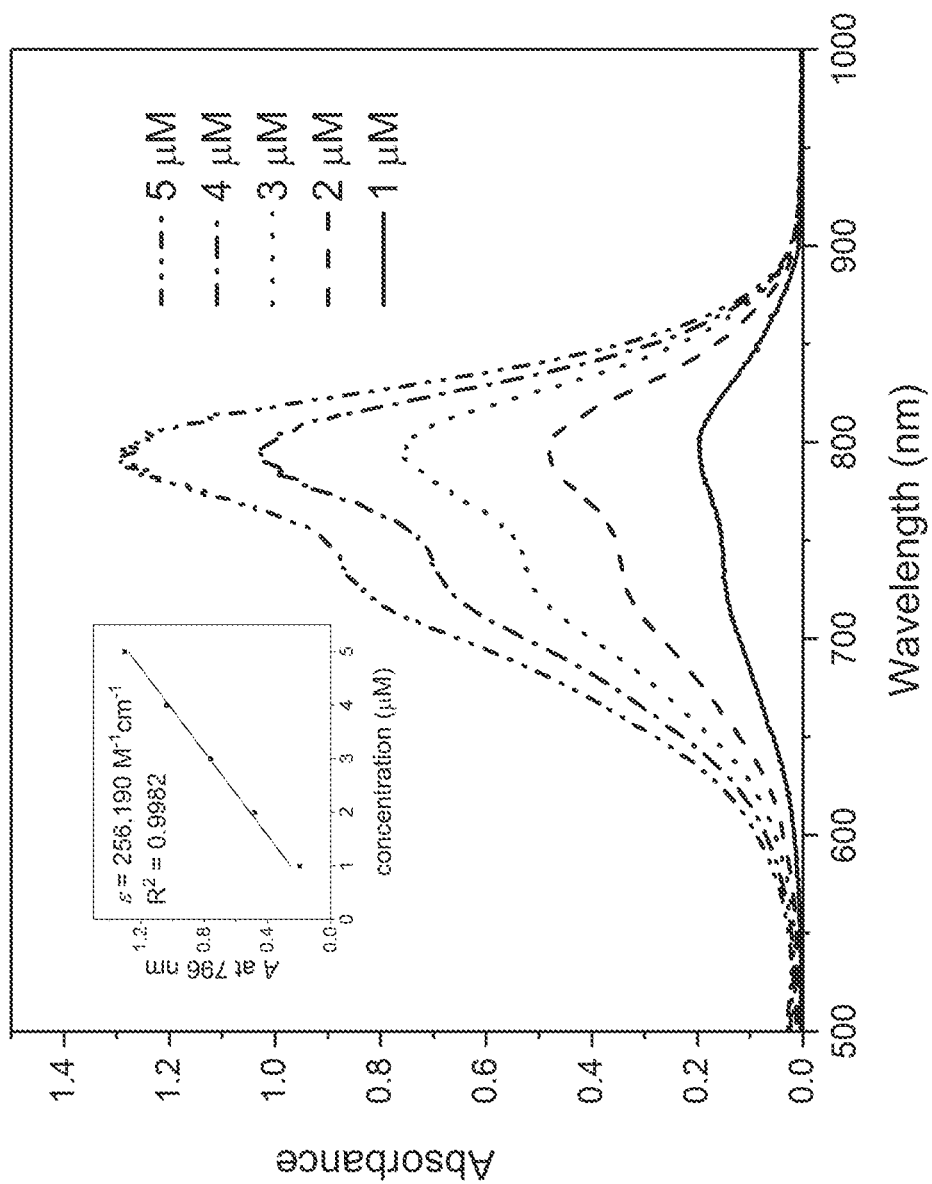
FIG. 10A shows absorption spectra of oxidative dimer 1 in FBS at room temperature. Insert: Beer-Lambert fit of the absorption at 1-5 µM.
Figure 10B:
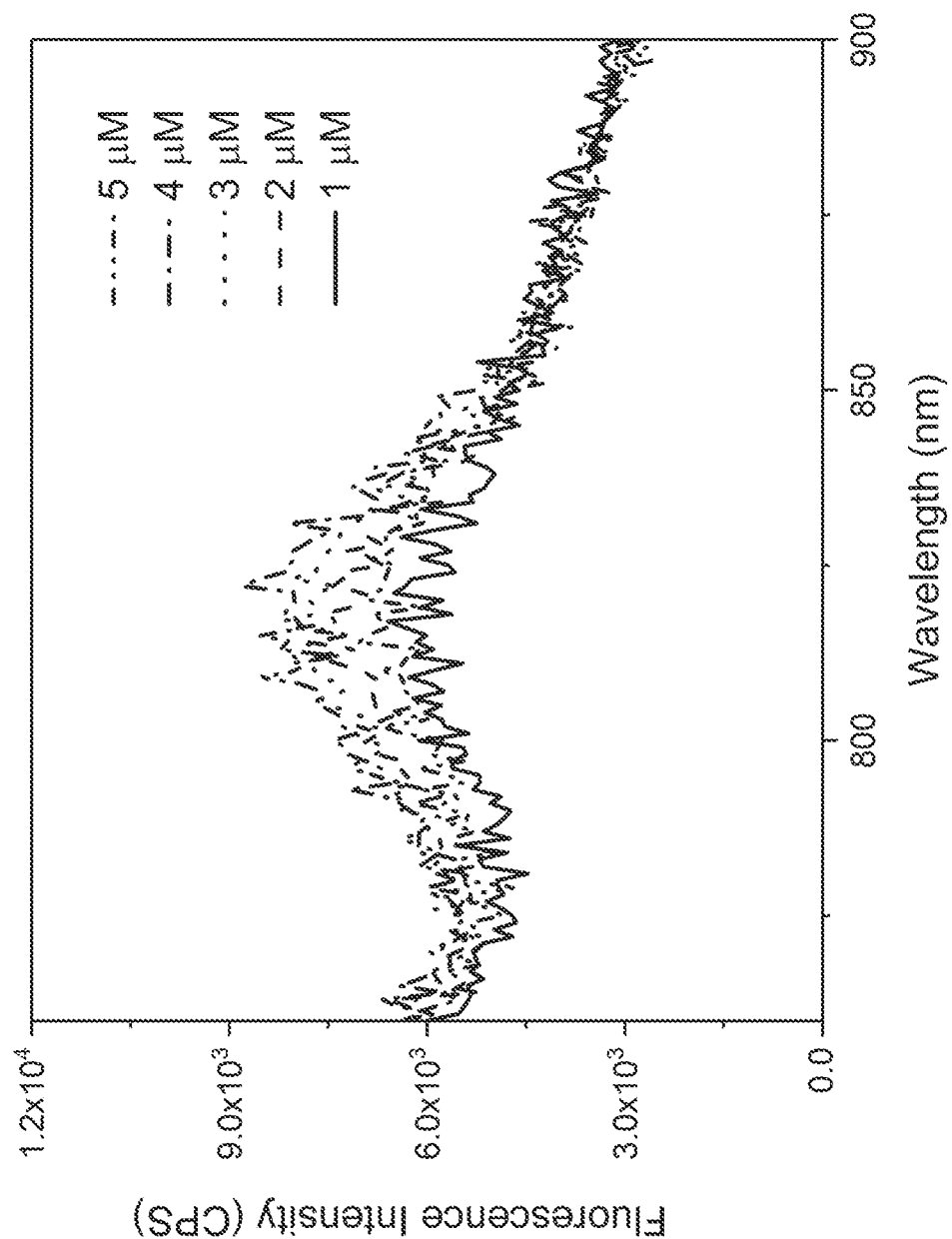
FIG. 10B shows fluorescence spectra of oxidative dimer 1 in FBS at room temperature. $\lambda_{ex}$=740 nm, slit width=5 nm.
Figure 11A:
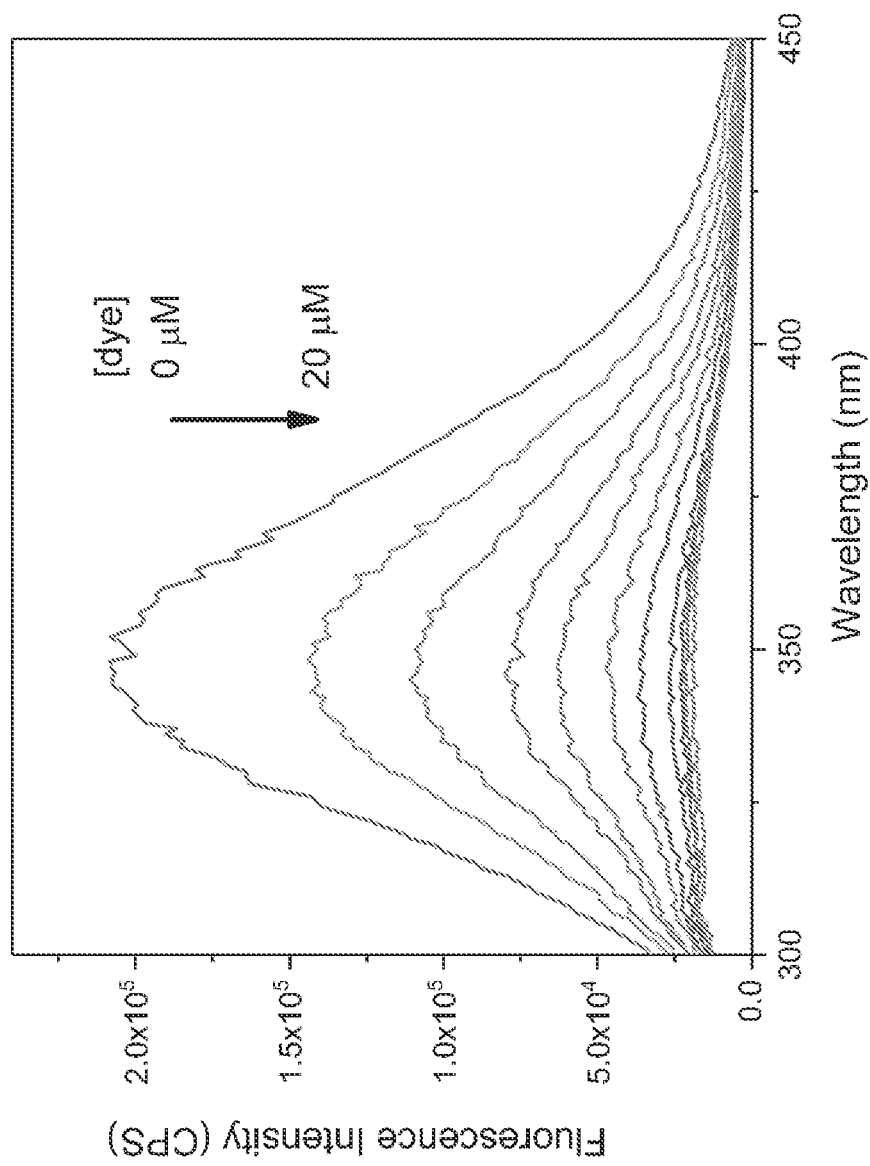
FIG. 11A shows fluorescence emission of bovine serum albumin (BSA) tryptophan (2 µM) upon addition of ICG (0-20 µM).
Figure 11B:
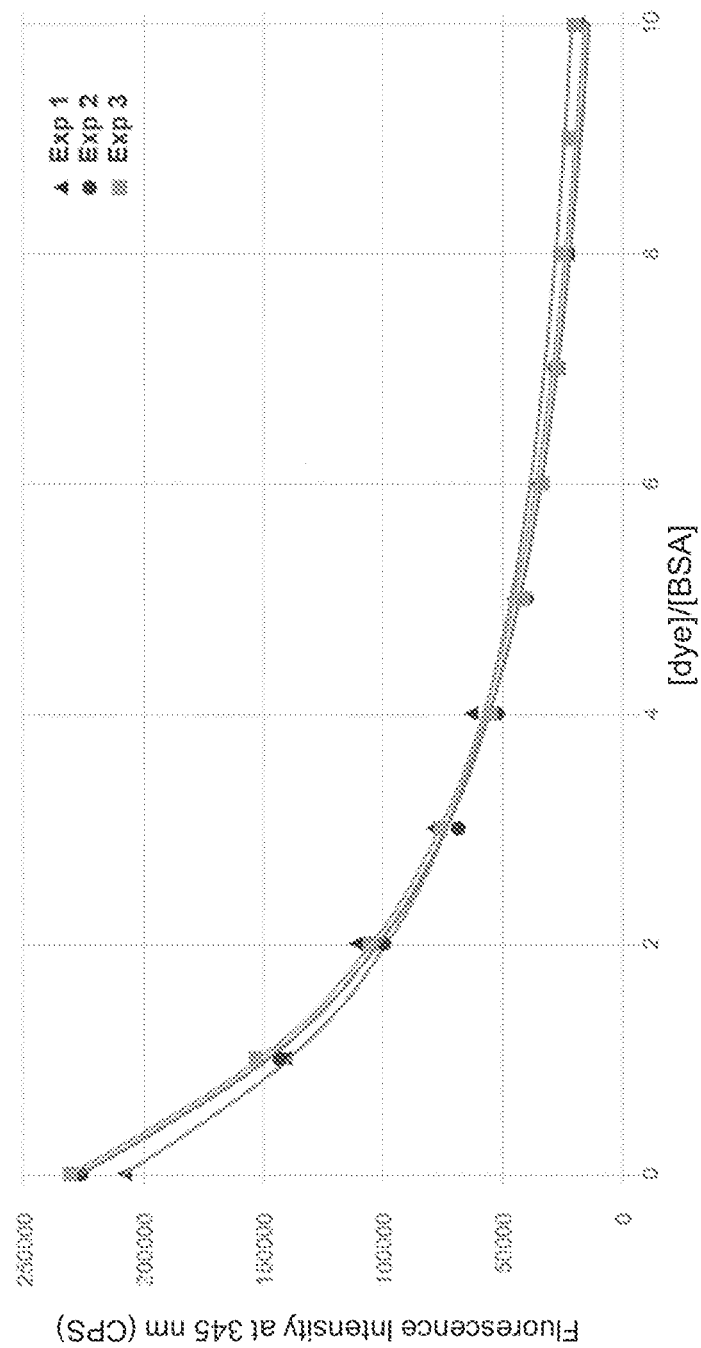
FIG. 11B shows curve fitting of titration isotherm to 1:1 model for binding of BSA with ICG in pH 7.4 PBS buffer at 37° C. $K_a$=(3.4±0.5)×10$^5$ M$^{-1}$. N=3.
Figure 12A:
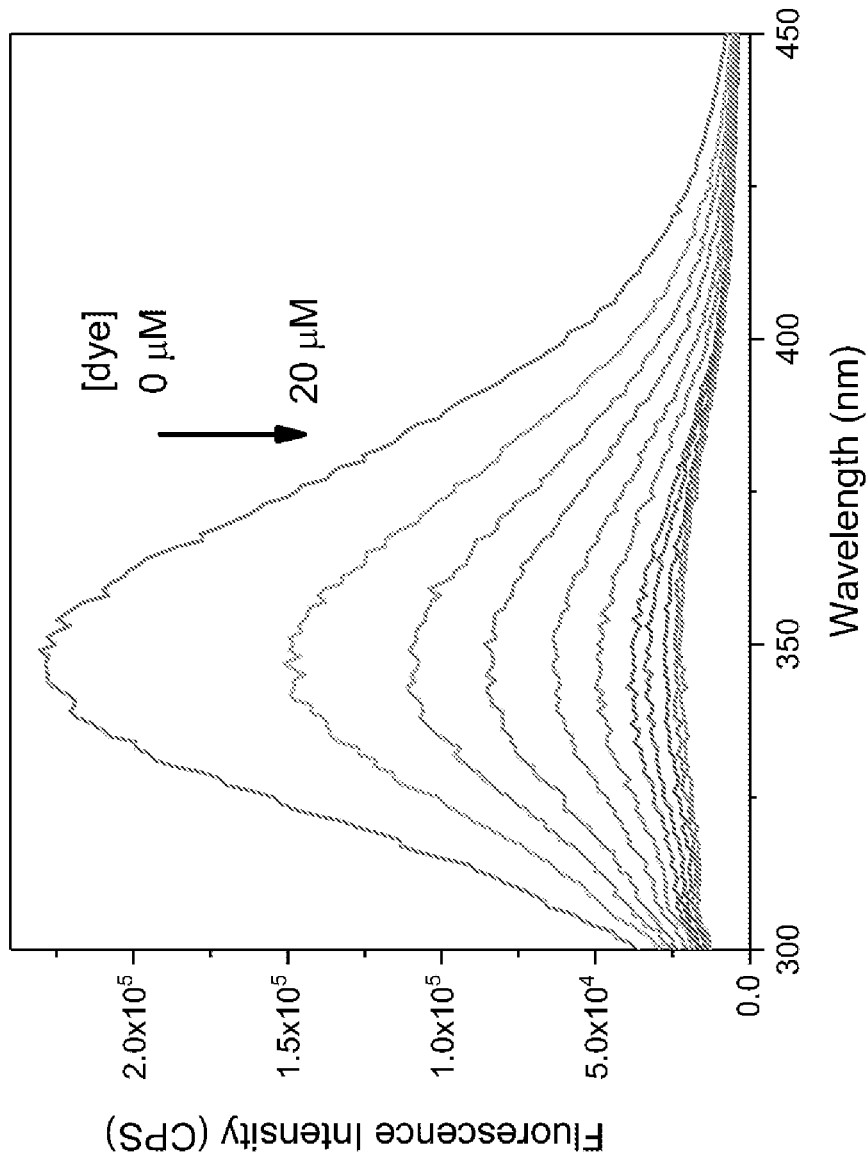
FIG. 12A shows fluorescence emission of BSA tryptophan (2 µM) upon addition of ICG-d$_5$ (0-20 µM).
Figure 12B:
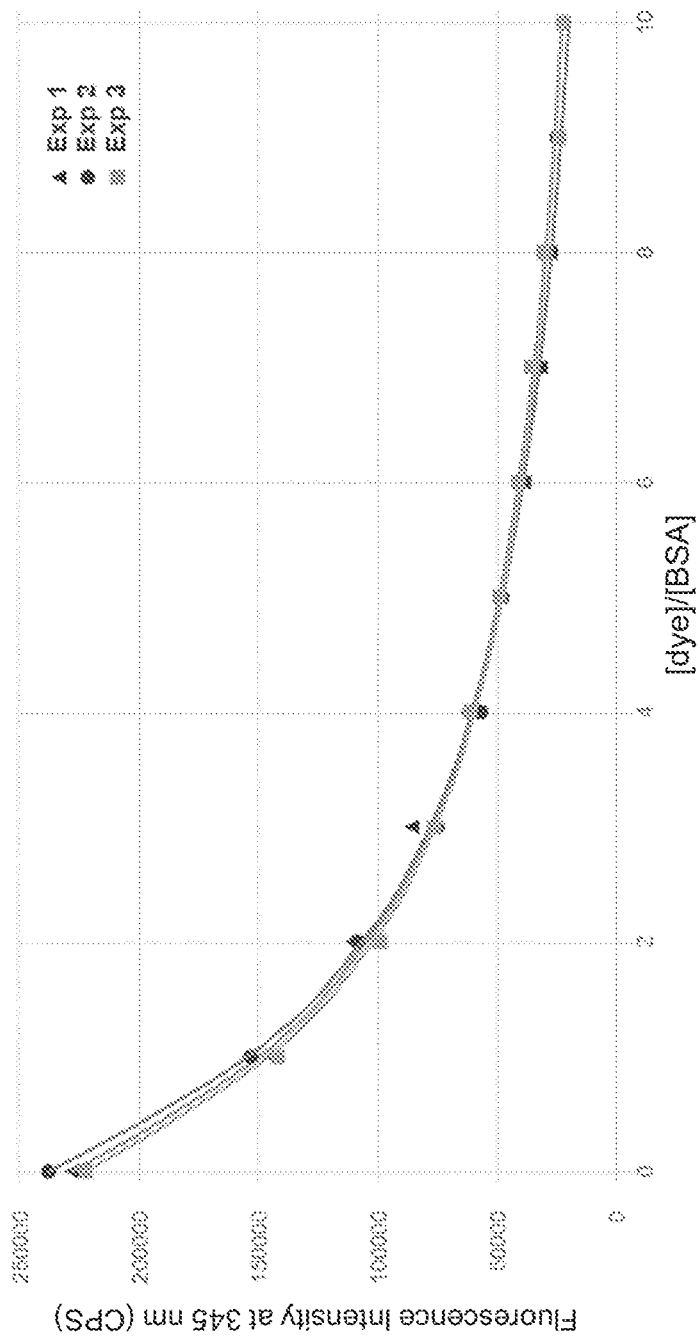
FIG. 12B shows curve fitting of titration isotherm to 1:1 model for binding of BSA with ICG-$d_5$ in pH 7.4 PBS buffer at 37° C. $K_a$=(3.8±0.6)×10$^5$ M$^{-1}$. N=3.
Figure 13A:
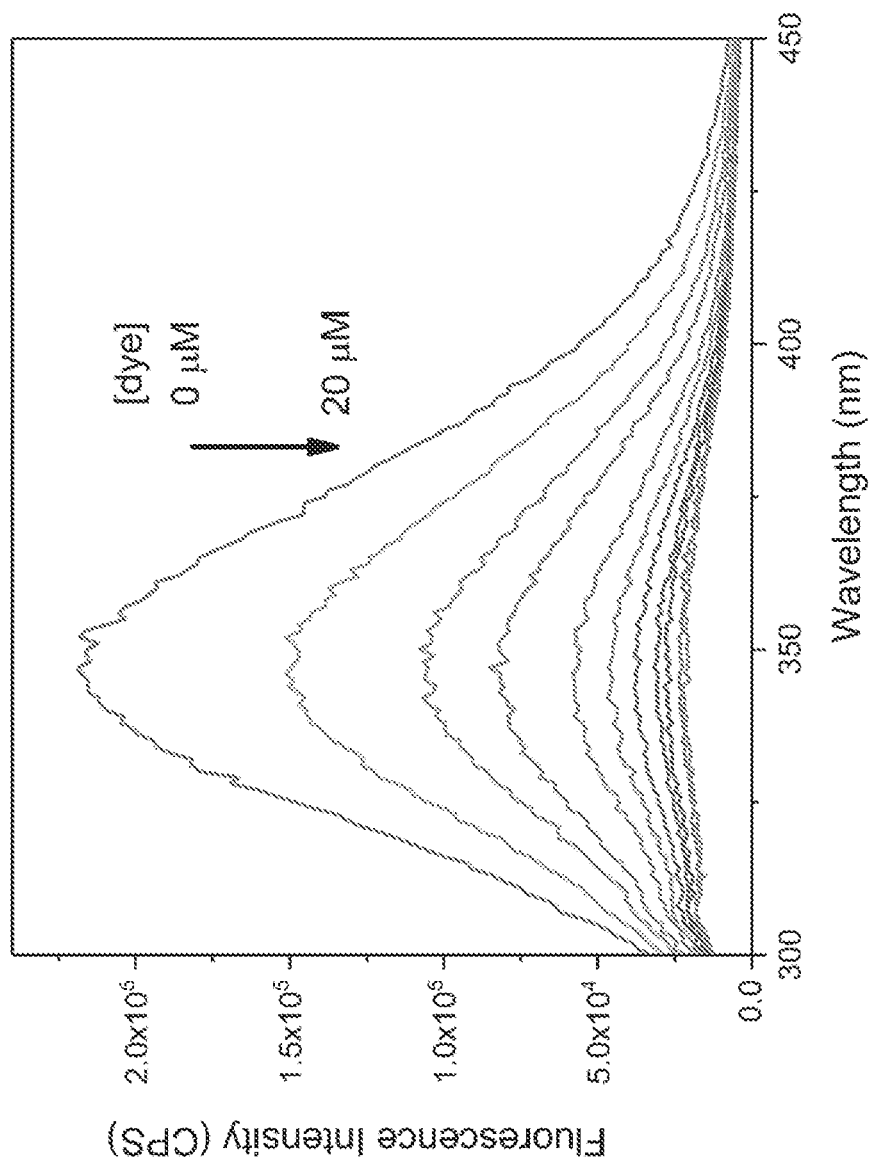
FIG. 13A shows fluorescence emission of BSA tryptophan (2 μM) upon addition of ICG-$d_7$ (0-20 μM).
Figure 13B:
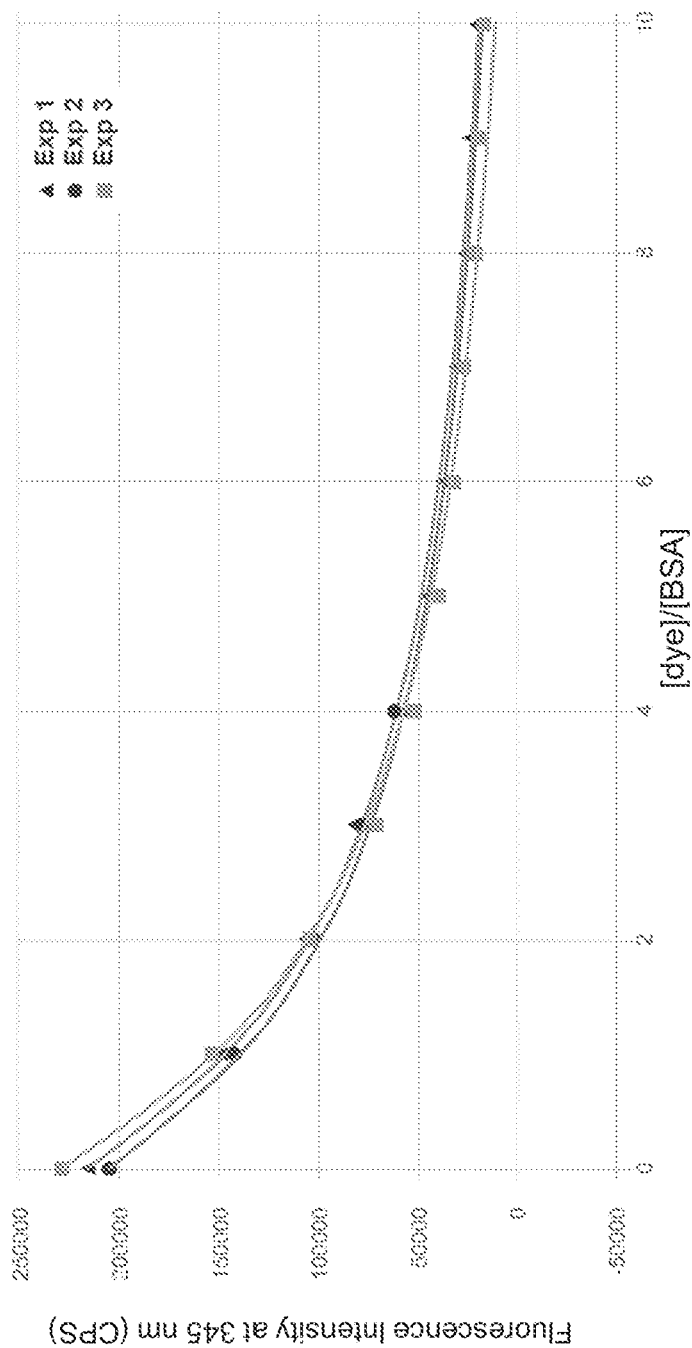
FIG. 13B shows curve fitting of titration isotherm to 1:1 model for binding of BSA with ICG-$d_7$ in pH 7.4 PBS buffer at 37° C. $K_a$=(3.0±0.5)×10$^5$ M$^{-1}$. N=3.
Figure 14A:
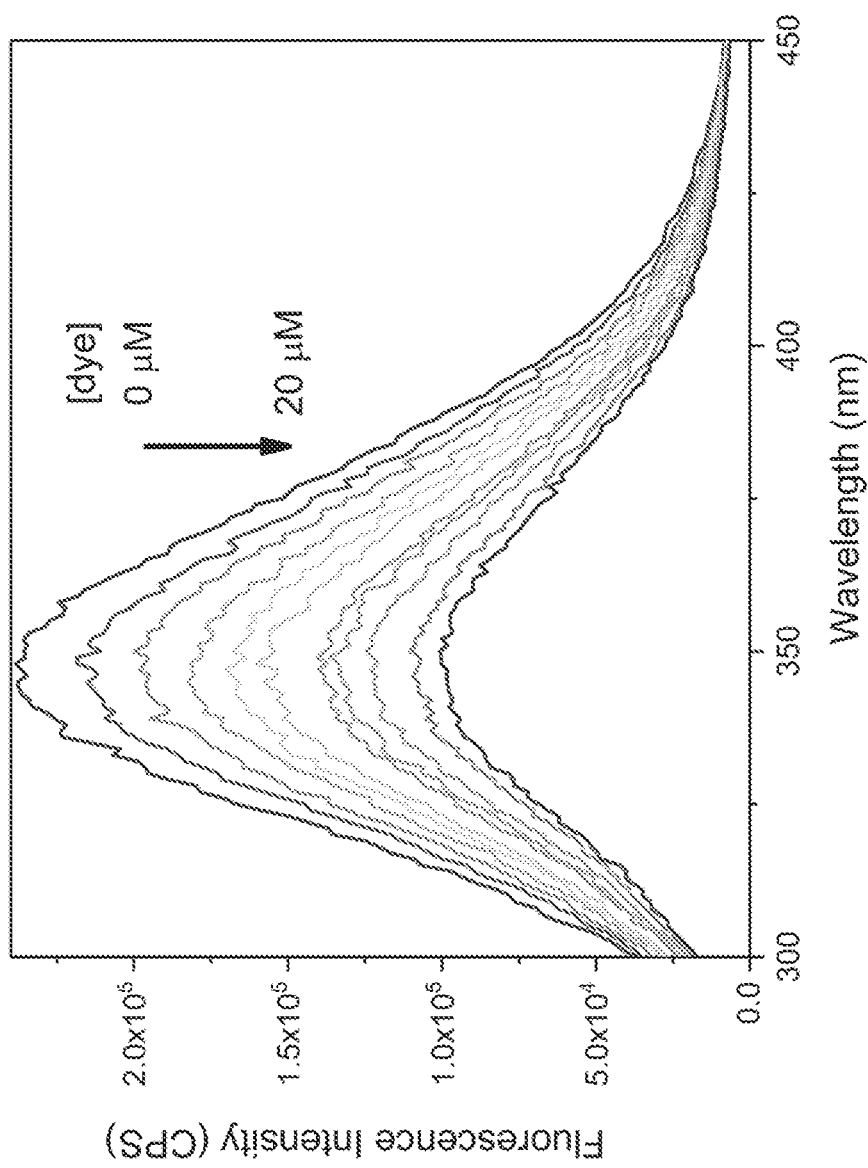
FIG. 14A shows fluorescence emission of BSA tryptophan (2 μM) upon addition of oxidative dimr 1 (0-20 μM).
Figure 14B:
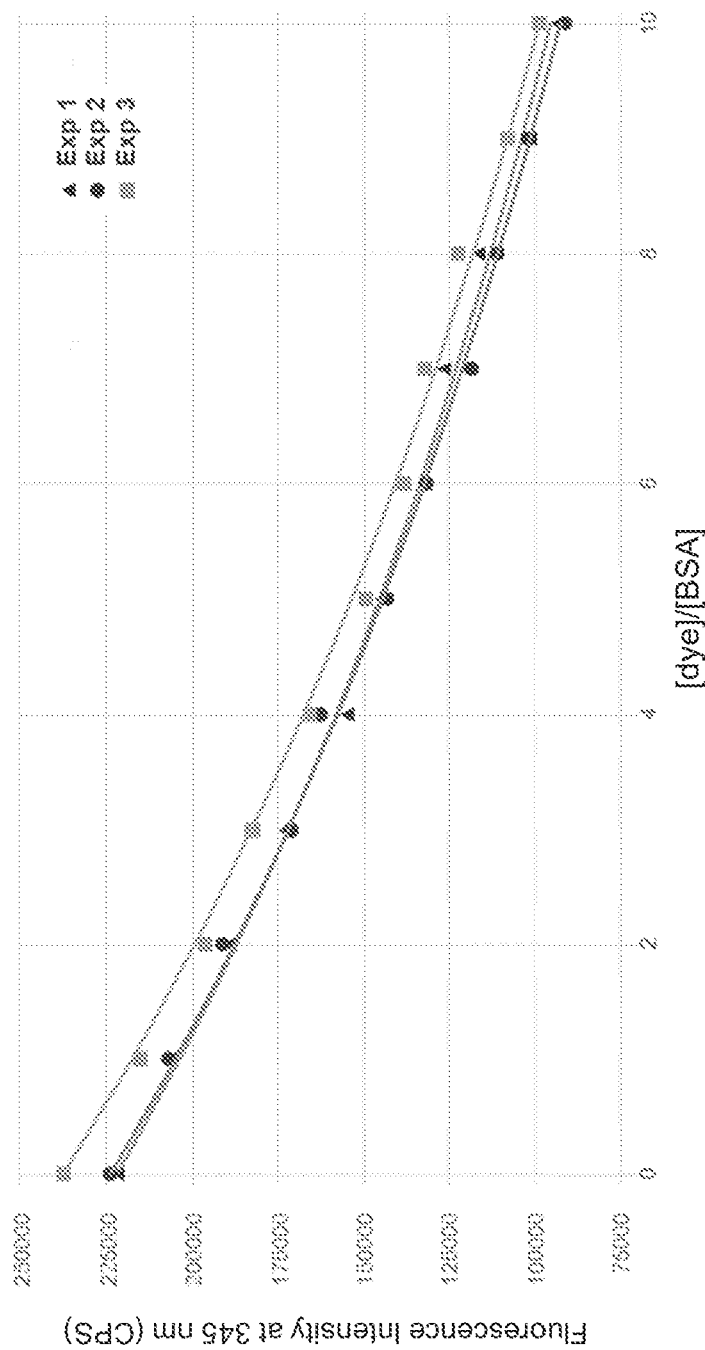
FIG. 14B shows curve fitting of titration isotherm to 1:1 model for binding of BSA with 1 in pH 7.4 PBS buffer at 37° C. $K_a$=(2.9±0.4)×10$^4$ M$^{-1}$. N=3.
Figure 15:
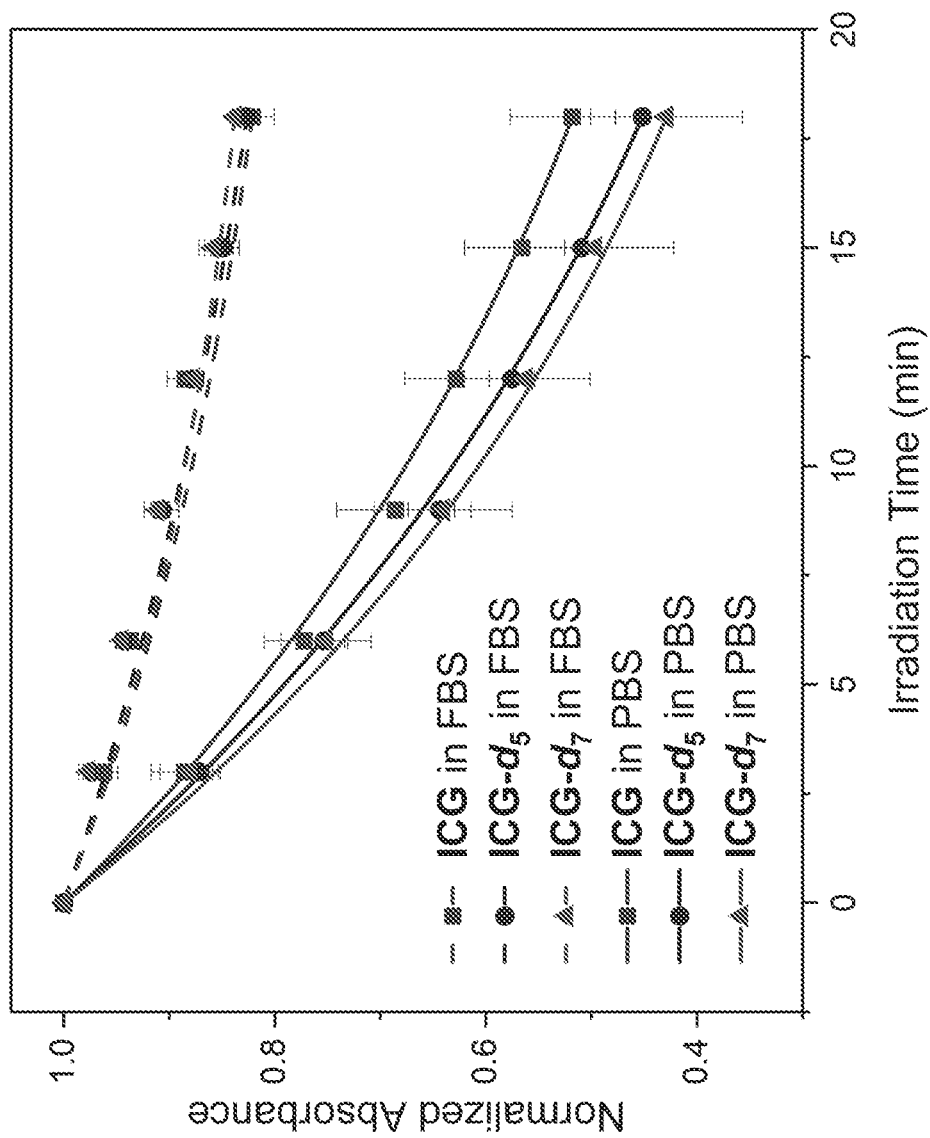
FIG. 15 shows photobleaching study 1a using lamp for high intensity irradiation: each cuvette containing 2 μM dye in PBS buffer, pH 7.4, or 100% FBS, was continuously irradiated by a 150 W Xenon lamp with a 620 nm long-pass filter. Each point is the average of experimental triplicate, and the error bars are standard deviation from the mean. The plot of normalized dye absorbance versus time was fit to a one-phase exponential decay.
Figure 18:
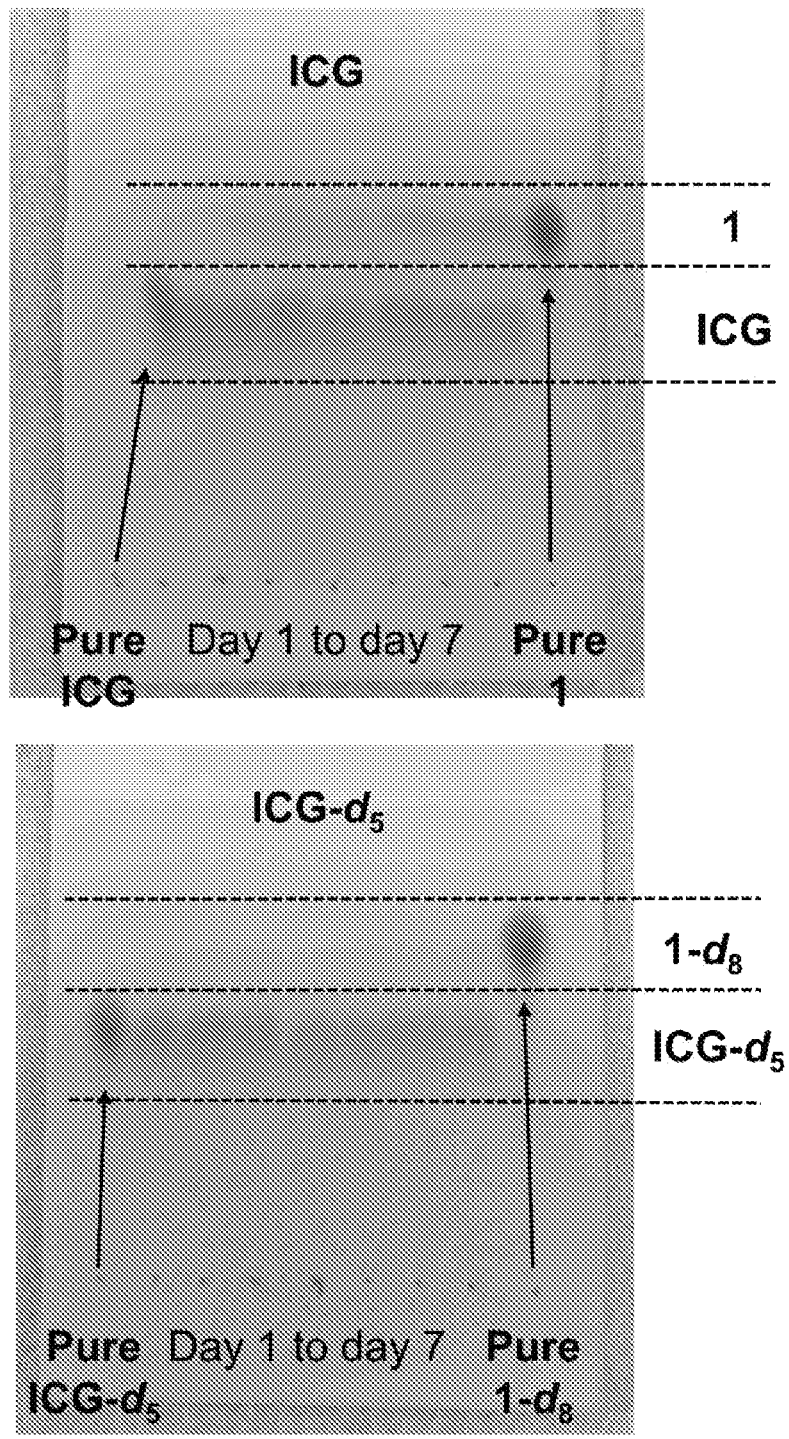
FIG. 18 shows separate aqueous stock solutions of ICG or ICG-$d_5$ (1.0 mM) were stored at room temperature and low photon intensity conditions (only exposed to lab lights during sample preparation and when aliquots were removed from samples). Every day, a 50 μL aliquot was removed from each stock solution, lyophilized, and stored as a solid at −20° C. After 7 days, all the aliquots from, (a) ICG stock solution, and (b) ICG-$d_5$ stock solution were analyzed on one reverse phase TLC plate (C18 silica, eluent: water/methanol=1:3, v/v). The TLC results show more degradation of ICG to form oxidative dimer 1, than degradation of ICG-$d_5$ to form its oxidative dimer, 1-$d_8$.
Figure 19:
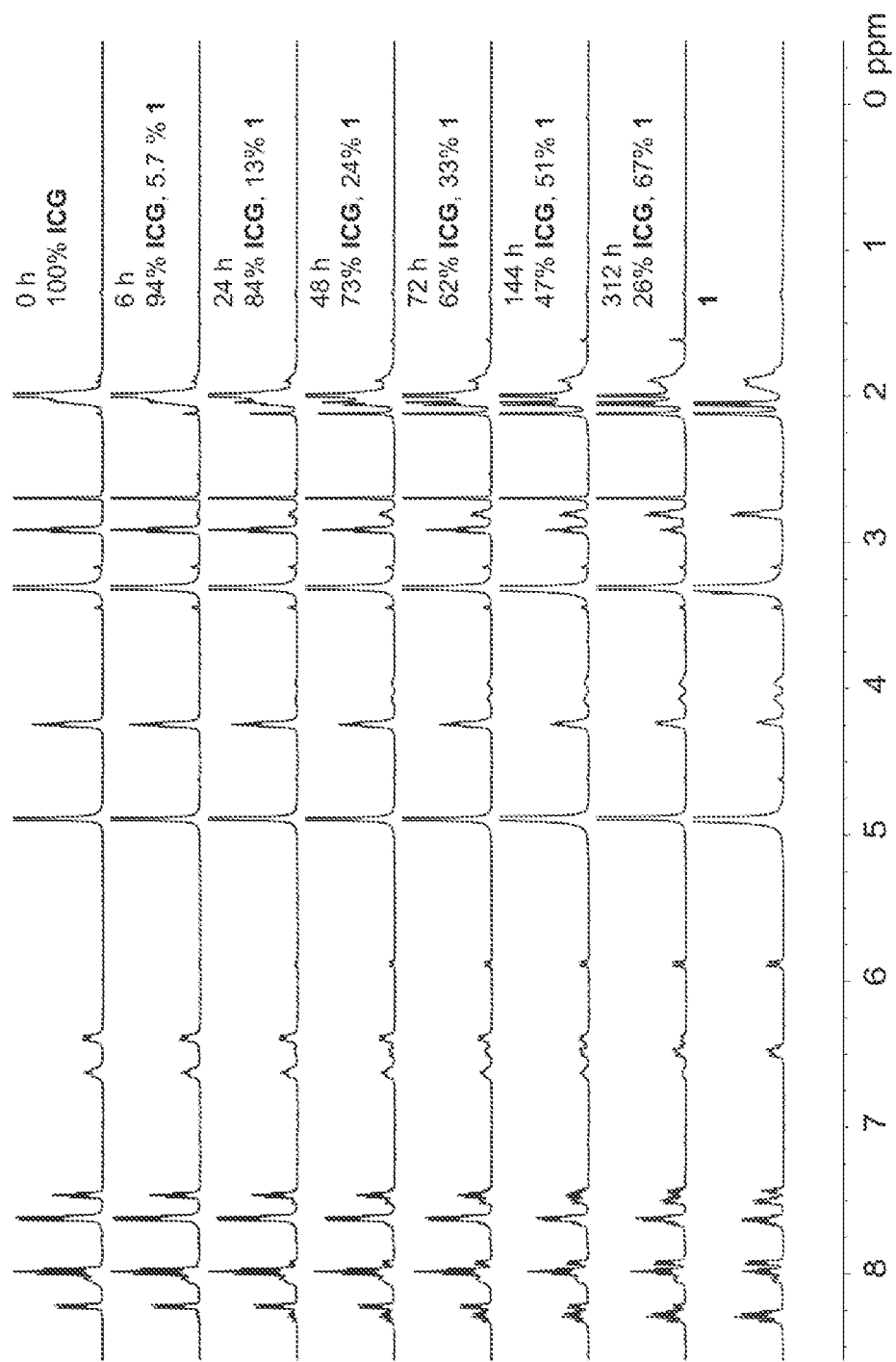
FIG. 19 shows $^1$H NMR spectra (500 MHz, methanol-$d_4$, 25° C.) of aliquots (1.0 mL) taken from a stock solution of ICG in water (1.0 mM, 10 mL, also containing 1.0 mM methyl sulfate sodium salt (MeSO$_3$Na) as internal NMR standard) that was stored at room temperature and low photon intensity conditions (only exposed to lab lights during sample preparation and when aliquots were removed from samples). At each time point, a 1.0 mL aliquot was taken from the stock solution, the aliquot was lyophilized, the solid residue was dissolved in 0.60 mL of methanol-$d_4$, and a $^1$H NMR spectrum was acquired. The weight percentages of ICG and oxidative dimer 1 were calculated by integration of the —CH$_2$SO$_3^-$ peak (δ=2.91 ppm for ICG, δ=2.80 ppm for oxidative dimer 1) and comparison with the internal standard (MeSO$_3$Na) peak at 2.69 ppm.
Figure 20:
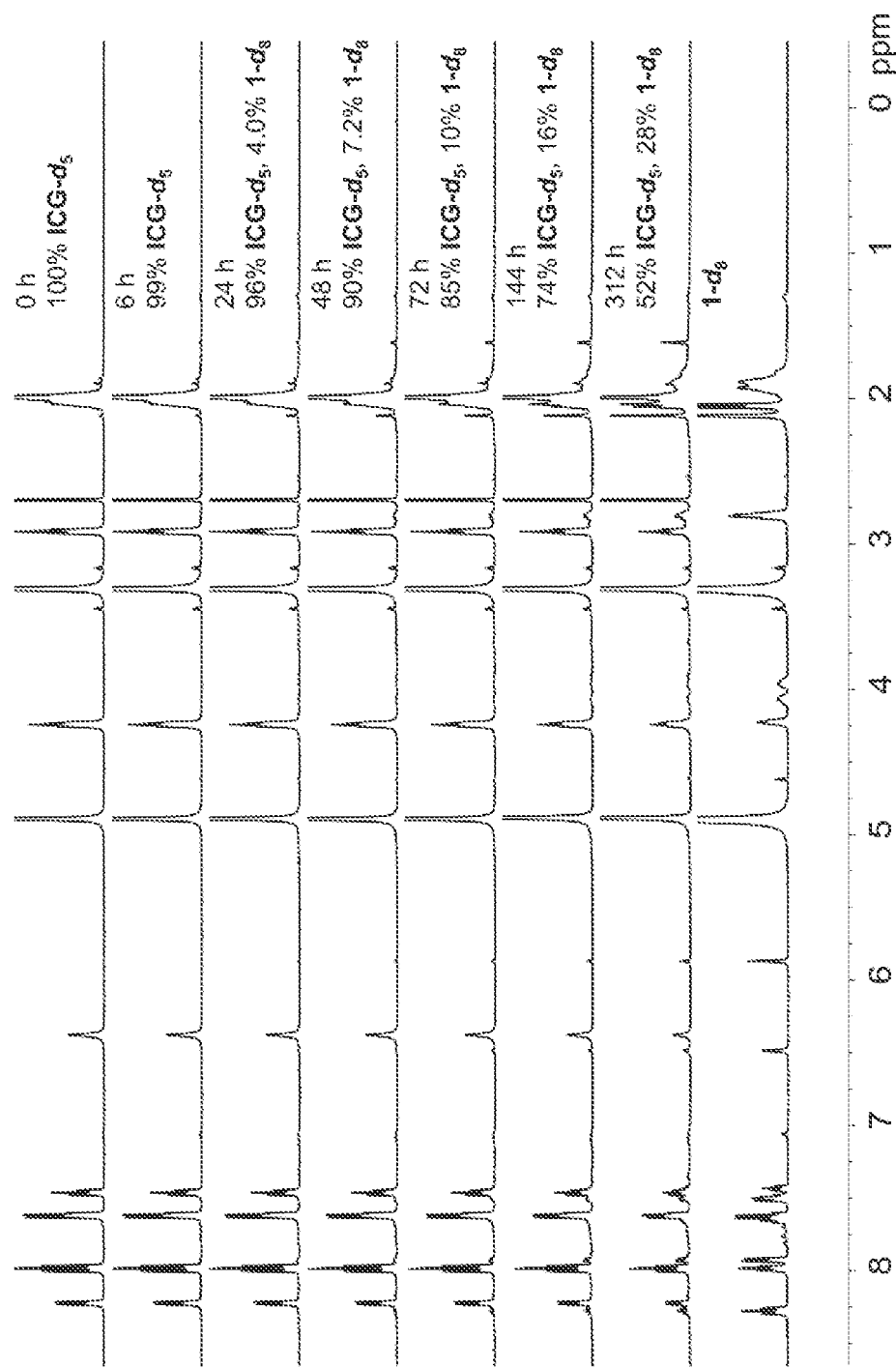
FIG. 20 shows $^1$H NMR spectra (500 MHz, methanol-$d_4$, 25° C.) of aliquots (1.0 mL) taken from a stock solution of ICG-$d_5$ in water (1.0 mM, 10 mL, also containing 1.0 mM MeSO$_3$Na as internal NMR standard) that was stored at room temperature and low photon intensity conditions (only exposed to lab lights during sample preparation and when aliquots were removed from samples). At each time point, a 1.0 mL aliquot was taken from the stock solution, the aliquot was lyophilized, the solid residue was dissolved in 0.60 mL of methanol-$d_4$, and a $^1$H NMR spectrum was acquired. The weight percentages of ICG-$d_5$ and oxidative dimer 1-$d_8$ were calculated by integration of the —CH$_2$SO$_3^-$ peak (δ=2.91 ppm for ICG-$d_5$, δ=2.80 ppm for 1-$d_8$) and comparison with the internal standard (MeSO$_3$Na) peak at 2.69 ppm.
Figure 21A:
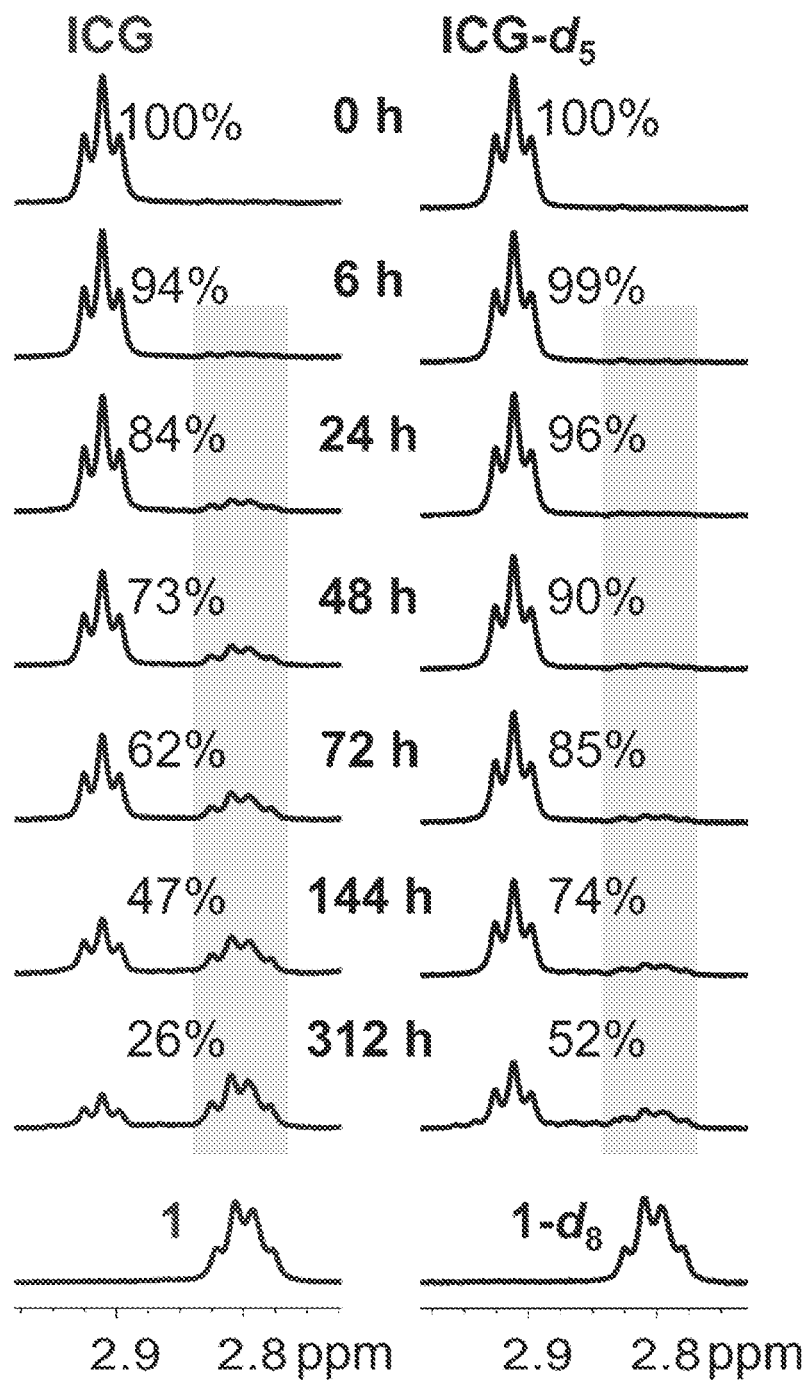
FIG. 21A shows partial $^1$H NMR spectra (500 MHz, methanol-$d_4$, 25° C.) illustrating differences in stability for separate stock solutions of ICG or ICG-$d_5$ in water (1.0 mM) at room temperature. The spectra show decrease of the peak for —CH$_2$SO$_3^-$ protons at δ=2.91 ppm for ICG or ICG-$d_5$ and increase of the corresponding peak at δ=2.80 ppm for oxidative dimer 1 or oxidative dimer 1-$d_8$.
Figure 21B:
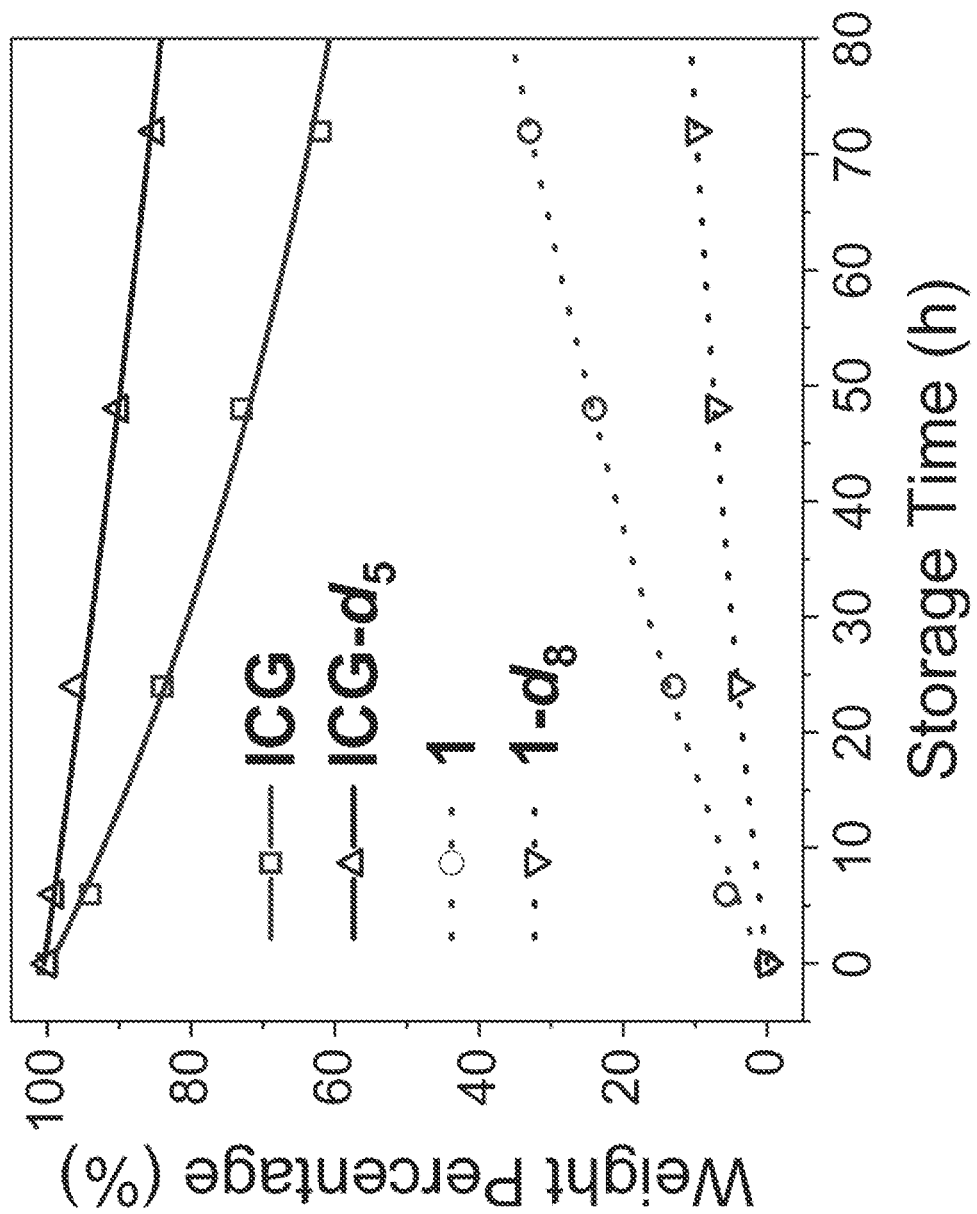
FIG. 21B shows speciation plots illustrating the change in weight percentage with storage time. Each plot was fit to a pseudo-second order dimerization reaction model.
Figure 21C:
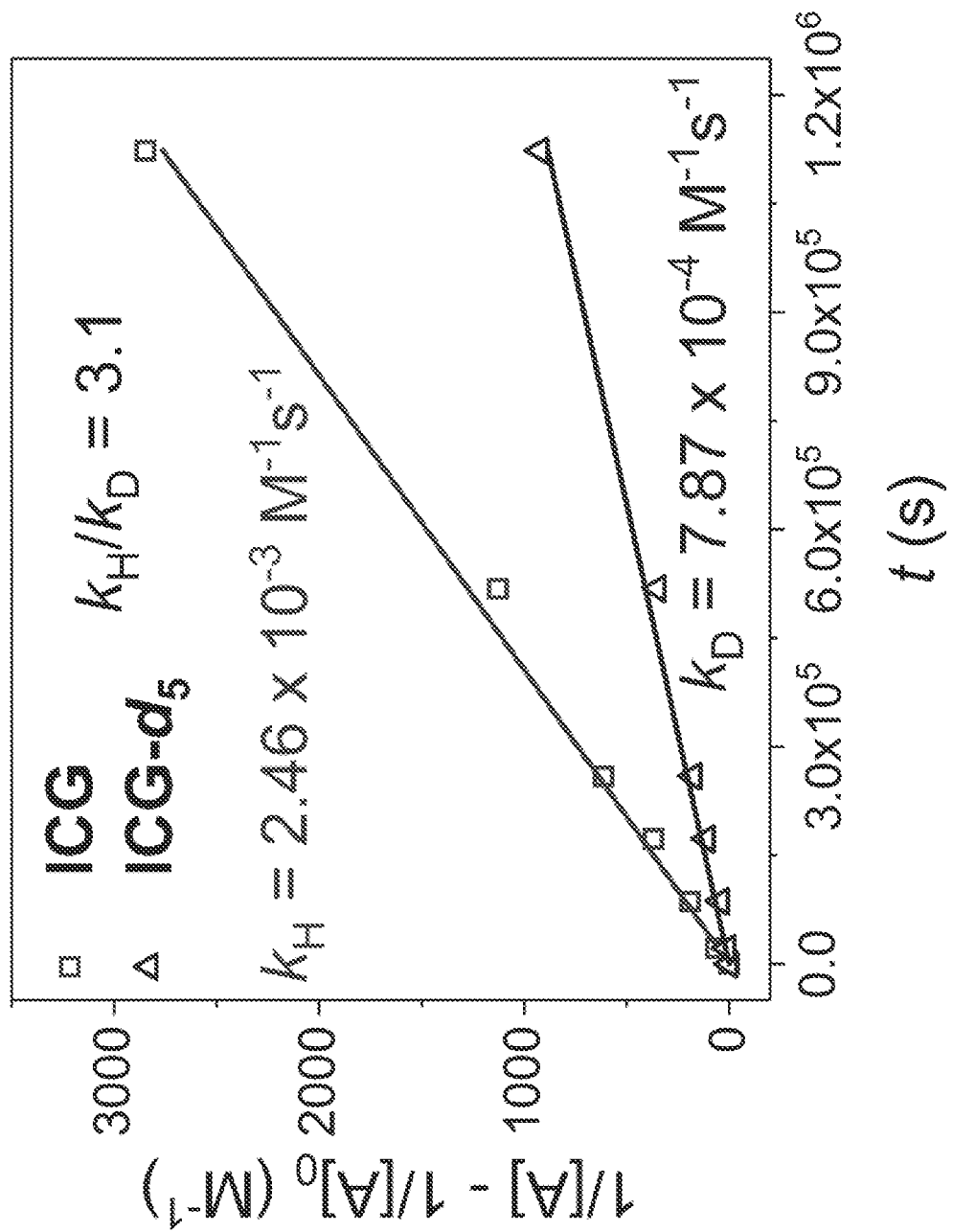
FIG. 21C shows curve fitting of the data to give the ratio of rate constants ($K_H/K_D$) as a deuterium kinetic isotope effect in water (1.0 mM) at room temperature (22° C.)
Figure 21D:
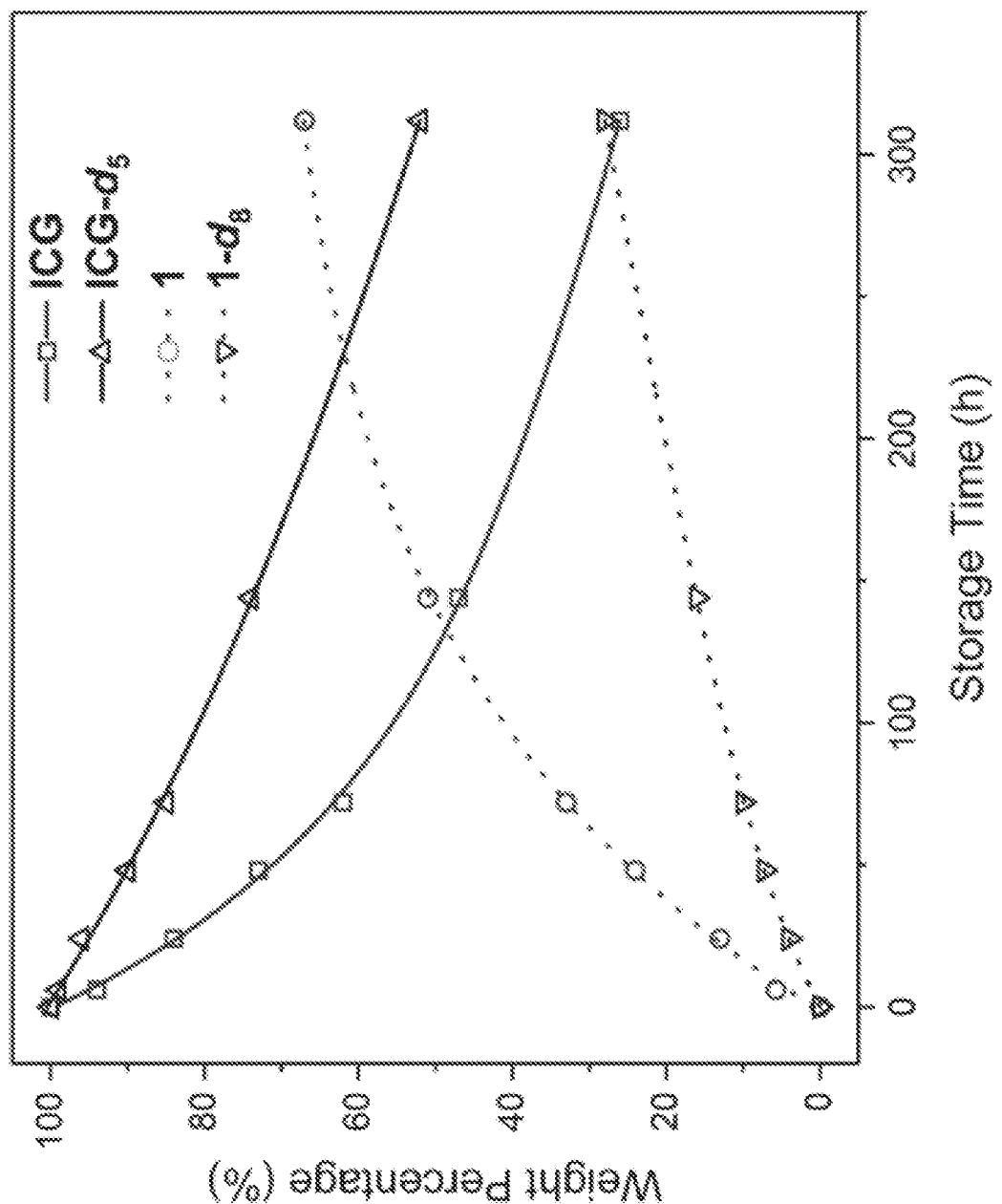
FIG. 21D shows speciation plots of FIG. 21B with expanded time plot.
Figure 22:
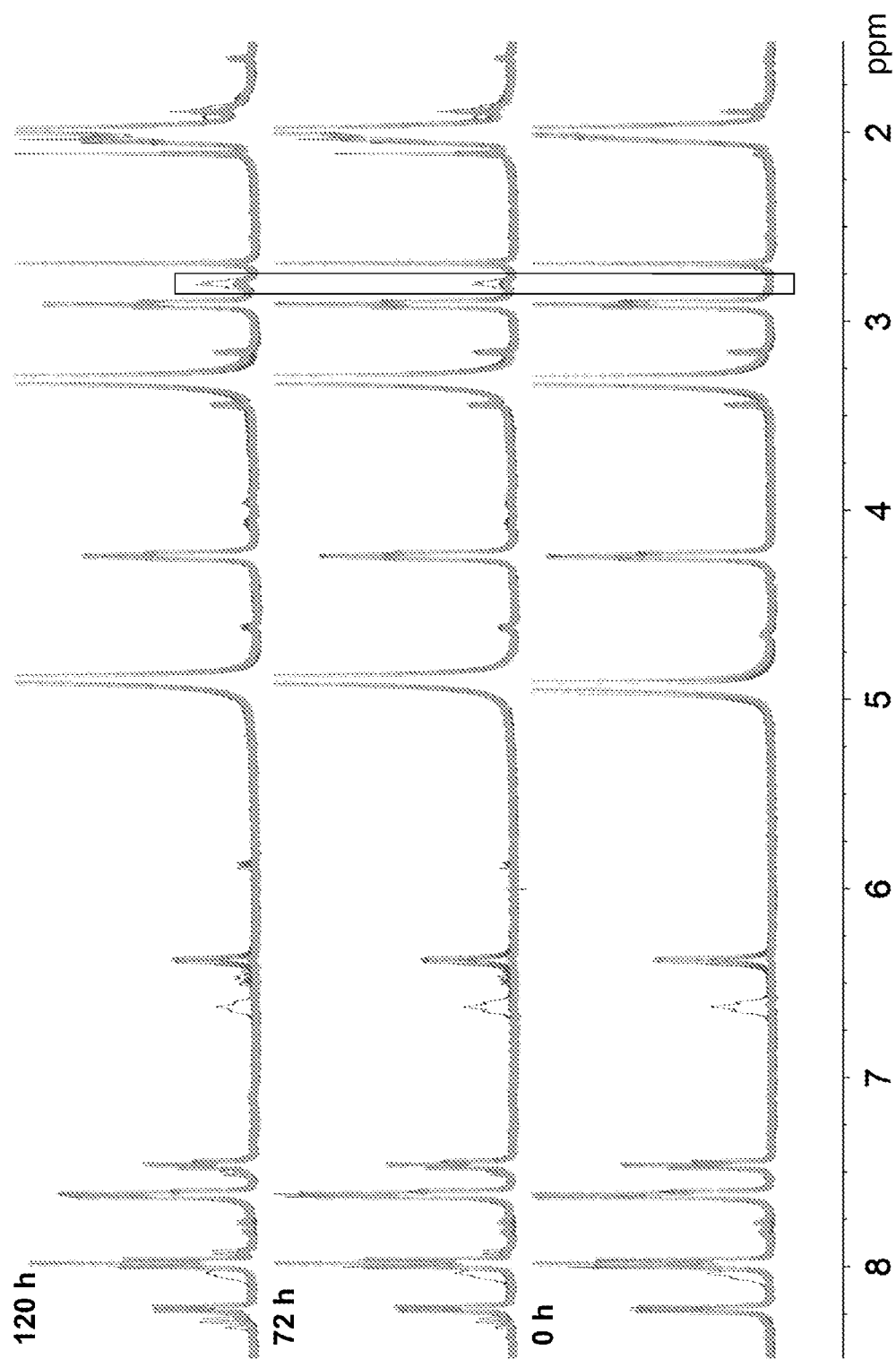
FIG. 22 shows stacked $^1$H NMR spectra (500 MHz, methanol-$d_4$, 25° C.) of aliquots from stock solutions of ICG (line), ICG-$d_5$ (circles) and ICG-$d_7$ (crosses) taken after 0 h, 72 h, and 120 h storage. Separate stock solutions of ICG, ICG-$d_5$ or ICG-$d_7$ (1.0 mM each) were dissolved in water with 1.0 mM MeSO$_3$Na (δ=2.69 ppm, internal standard) to make a 1.0 mM solution. The solutions were stored at room temperature and low photon intensity conditions (only exposed to lab lights during sample preparation and when aliquots were removed from samples). After 72 h and 120 h, 1 mL aliquots were taken from each stock solution and lyophilized. In each case, the solid residue was dissolved in 0.6 mL of methanol-$d_4$ and a $^1$H NMR spectrum was recorded. The weight percentage of each species was calculated by the integration of its —CH$_2$SO$_3^-$ residue (δ=2.91 ppm for ICG, ICG-$d_5$, or ICG-$d_7$, δ=2.80 ppm for oxidative dimer 1, oxidative dimer 1-$d_8$, or oxidative dimer 1-$d_{12}$) and calibrated by the internal standard to give the quantitative data shown in Table 3. The black box at ~2.8 ppm highlights the relative amounts of oxidative dimer 1 (line), oxidative dimer 1-$d_8$ (circles), or oxidative dimer 1-$d_{12}$ (crosses) at each time point.

That is, the dye concentration was low (2 µM), the photon flux was continuous and high (Xenon lamp light source), and the samples were exposed to air. For the high photon intensity studies an intense light source (Xenon lamp) was used to simultaneously illuminate separate solutions of the three dyes (each 2.0 µM in phosphate buffer solution (PBS)), and the changes in near-infrared (NIR) absorption spectra were monitored over time. The curves in FIG. 15 illustrate that all three dye solutions exhibit essentially the same rate of photobleaching. A repeat experiment examined the three dyes in FBS and observed a slower rate of photobleaching (consistent with the known protection of ICG due to non-covalent association with the albumin, globulin, and lipoprotein in FBS) with no difference between the dyes. In other words, the photobleaching experiments indicated no noticeable deuterium kinetic isotope effect, a finding that is consistent with two observations from previous studies: (a) the mechanism for ICG photobleaching under high photon intensity illumination conditions is cycloaddition with photogenerated singlet oxygen and formation of unstable dioxetane intermediates that fragment to produce the carbonyl-containing compounds, and (b) dioxetane fragmentation is known to exhibit a negligible secondary deuterium kinetic isotope effect. The second set of dye stability experiments were designed to mimic the low photon intensity storage conditions experienced by a typical reconstituted dose in water before it is administered in a clinical setting. Thus, stock solutions of the dyes were exposed to the atmosphere and laboratory lights during the initial reconstitution and periodic sampling, but otherwise stored as capped vials in the dark at room temperature. Most literature studies on the stability of aqueous ICG have focused on relatively dilute solutions (<50 µg/mL), and few studies have examined aqueous ICG solutions at the higher concentrations that match a reconstituted clinical dose (e.g., 1.0-2.5 mg/mL). The water solubility of ICG is 1 mg/mL, therefore, to ensure that all experiments tested completely dissolved aqueous solutions a consistent concentration of 1.0 mM (0.775 mg/mL) was employed. The purity and composition of a 1.0 mM stock solution of ICG in water was tracked over time by periodically removing an aliquot and analyzing its chemical composition at a semi-quantitative level by reverse phase thin layer chromatography (TLC), or at a quantitative level using $^1$H NMR spectroscopy. Under typical clinical reconstitution and shelf-storage conditions, the oxidative dimerization of aqueous ICG to produce oxidative dimer 1 (Scheme 1, pathway C) was observed to be the dominant degradation pathway and preparative experiments provided pure samples of oxidative dimers 1, 1-$d_8$, and 1-$d_{12}$. The $^1$H NMR and mass spectra of oxidative dimers 1, 1-$d_8$, and 1-$d_{12}$ were internally consistent (FIG. 2) and matched the literature data. The first indication that a stored 1.0 mM solution of aqueous ICG-$d_5$ was substantially more stable than a homologous solution of ICG was gained by monitoring stock solutions over one week at room temperature using reverse phase TLC (FIG. 18). This finding was confirmed by comparing NMR spectra of aliquots taken periodically from the separate stored stock solutions (FIGS. 19-20). Shown in FIG. 21A are the changes over time for one particularly diagnostic peak corresponding to the —CH$_2$SO$^-$ protons at δ=2.91 ppm for ICG or ICG-$d_5$, and δ=2.80 ppm for oxidative dimer 1 or oxidative dimer 1-$d_8$. Comparison of peak integration values with an internal NMR standard (CH$_3$SO$_3$Na, δ=2.69 ppm) produced kinetic plots (FIG. 21B, with expanded time plot in FIG. 21D) that could be analyzed to provide second order rate constants for the bimolecular dimerization reaction to form oxidative dimer 1 (or 1-$d_8$) (FIG. 21C). The ratio of rate constants (deuterium kinetic isotope effect) shows that the conversion of aqueous ICG-$d_5$ to oxidative dimer 1-$d_8$ is slower than the conversion of ICG to oxidative dimer 1 by a factor of 3.1. A subsequent kinetic study used the same NMR assay to quantify the conversion of ICG-$d_7$ to oxidized dimer 1-$d_{12}$ and found that it matched the conversion rate of ICG-$d_5$ to 1-$d_8$ (FIG. 22 and Table 3).

TABLE 3

Weight percentage of ICG, ICG-d$_5$ and ICG-d$_7$ remaining in aqueous stock solutions (1.0 mM, also containing 1.0 mM MeSO$_3$Na as internal NMR standard) after storage for 72 h and 120 h. Results are the average of three independent experiments and the errors are standard deviations from the mean.

| Storage time (h) | ICG (wt %) | ICG-d$_5$ (wt %) | ICG-d$_7$ (wt %) |
|---|---|---|---|
| 72 | 73.6 ± 1.7 | 86.0 ± 0.8 | 84.7 ± 0.7 |
| 120 | 67.4 ± 1.0 | 80.9 ± 1.2 | 80.7 ± 0.6 |

Figure 24:
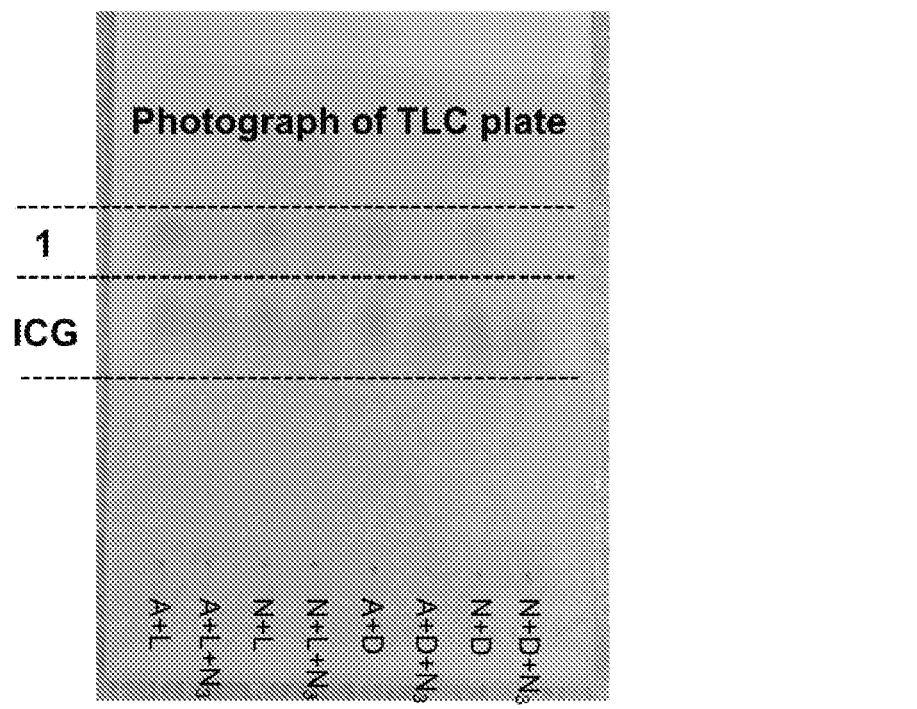
FIG. 24 shows reverse phase TLC (C18 silica, eluent: water/methanol=1/3, v/v) results of 1.0 mM ICG after 30 h storage in water at room temperature under different conditions. A=sample prepared and stored under air atmosphere, N=sample prepared under nitrogen atmosphere but there was no exclusion of air from the aqueous solution; L=sample stored with continual laboratory light exposure, D=sample prepared in the light but stored in the dark; $N_3$=10 equivalents of sodium azide as additive. The weight ratios of ICG to oxidative dimer 1 were calculated by the ratio of the —$CH_2SO_3^-$ peak integration for NMR spectra acquired after the samples were lyophilized and dissolved in methanol-$d_4$. The results show that minimal exposure of 1.0 mM ICG to air and laboratory lights inhibits formation of oxidative dimer 1, and complete inhibition of oxidative dimer 1 is achieved by the presence of azide anion ($N_3^-$) a known quencher of singlet oxygen.
Figure 25:
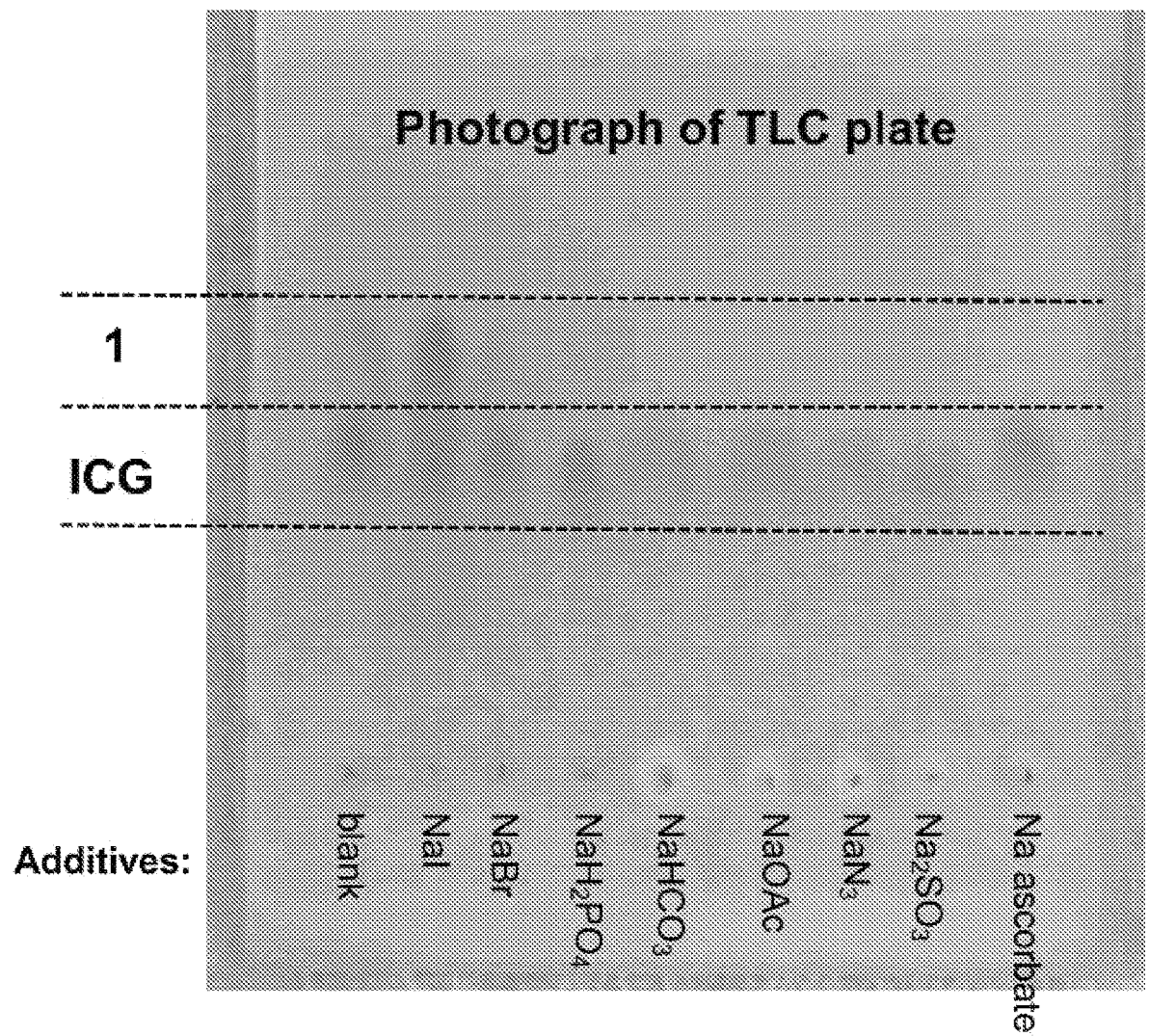
FIG. 25 shows reverse phase TLC (C18 silica, eluent: water/methanol=1:3, v/v) analysis of 1 mM ICG after 24 h storage in water with different additives (NaI, NaBr, $NaH_2PO_4$, $NaHCO_3$, NaOAc, $NaN_3$, $Na_2SO_3$, and Na ascorbate, 10 molar equivalents), at room temperature and low photon intensity light. The dimerization to form oxidative dimer 1 was stopped by base ($NaHCO_3$ and NaOAc), singlet oxygen quencher ($NaN_3$) and reductant ($Na_2SO_3$ and Na ascorbate).

The dimerization reaction to produce 1 was inhibited when air and/or light was excluded from the reaction (FIG. 24). However, slow production of 1 continued after an illuminated sample of ICG was placed in the dark. The dimerization reaction was strongly inhibited by the presence of additives that act as antioxidants, such as azide and ascorbate, but it was promoted by the presence of NaI an additive in some commercial versions of ICG (FIG. 25).

Example 14: Photobleaching Studies i. Photobleaching Study 1a (Low Dye Concentration in Water)

A solution of dye (2 μM) in pH 7.4 PBS buffer or FBS, was placed in a cuvette (1 cm pathlength) that was exposed to air and illuminated at a distance of 5 cm by a 150 W Xenon lamp with a 620 nm long-pass filter. An absorbance spectrum was recorded every 3 min. The normalized maximum absorbance of dye was plotted against time and fitted to a non-linear regression, one-phase exponential decay. Experiments were conducted in triplicate.

ii. Photobleaching Study 1b (Comparison of High and Low Dye Concentration in Water or Ethanol)

Figure 16:
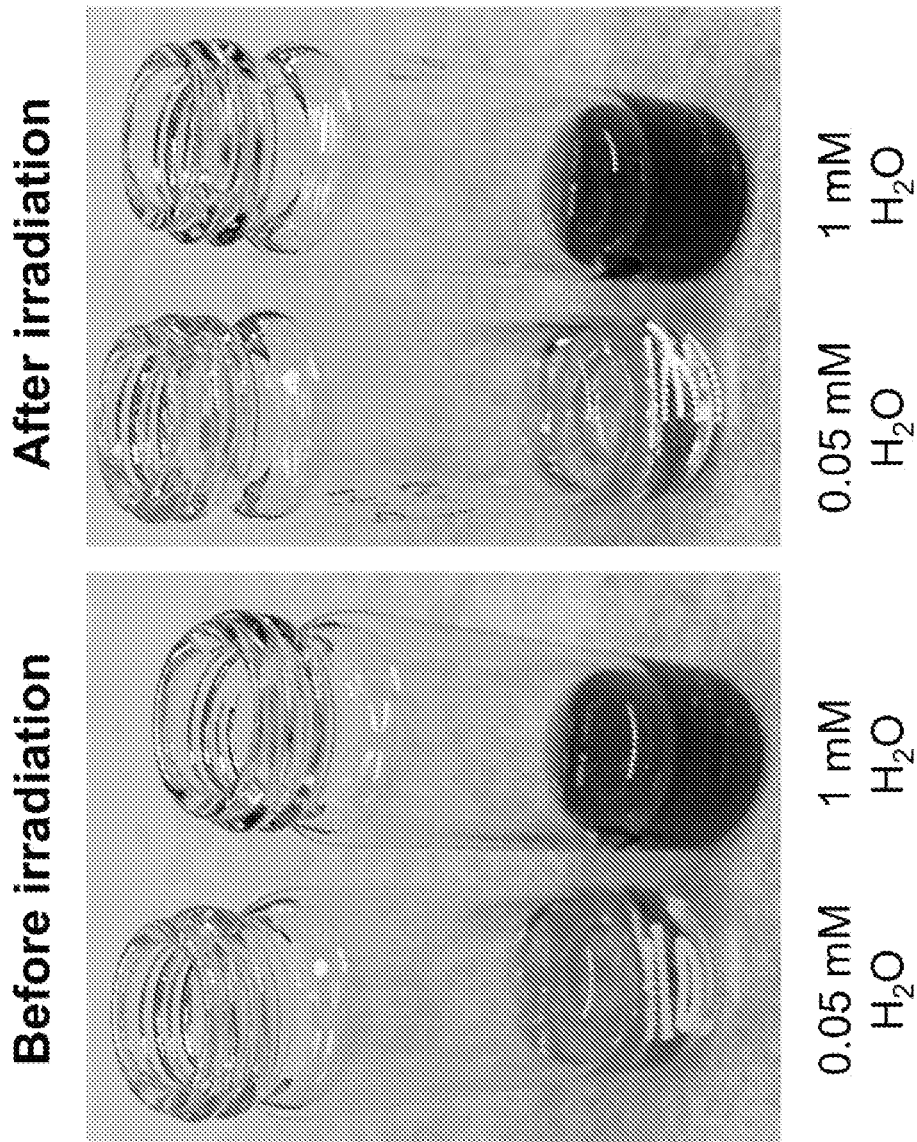
FIG. 16 shows photobleaching study 1b using lamp for high intensity irradiation: (a) photographs of two separate vials containing 0.05 mM (left) or 1.0 mM (right) ICG in water before and after 6 h irradiation; there is much more bleaching of the low concentration solution.
Figure 17:
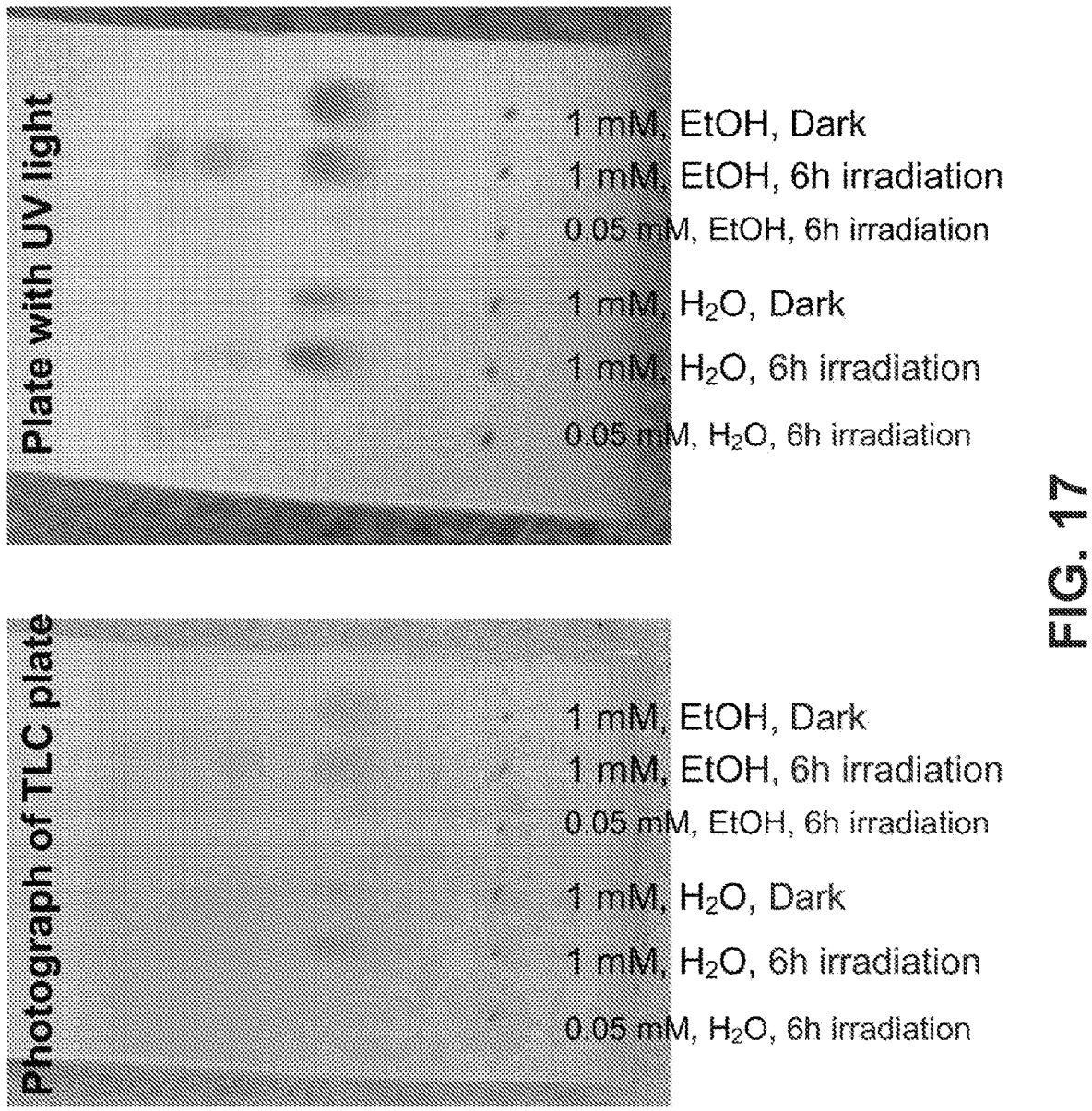
FIG. 17 shows photobleaching study 1b using lamp for high intensity irradiation. Reverse phase thin layer chromatography (TLC) (C18, eluent: water/methanol=1:3, v/v) analysis shows that a 1.0 mM ICG solution in water is more photostable than a 0.05 mM ICG solution in water and more photostable than a 0.05 mM or 1.0 mM ICG solution in ethanol.

1 mL solutions of ICG (1.0 mM or 0.05 mM) in water or ethanol were irradiated continuously with a 150 W Xenon lamp with a 620 nm long-pass filter for 6 h at room temperature and each solution was analyzed by reverse phase TLC (FIGS. 16-17). There appeared to be less photochemical degradation when the concentration of ICG in water or ethanol was increased (FIGS. 16-17, FIG. 26B).

Figure 26A:
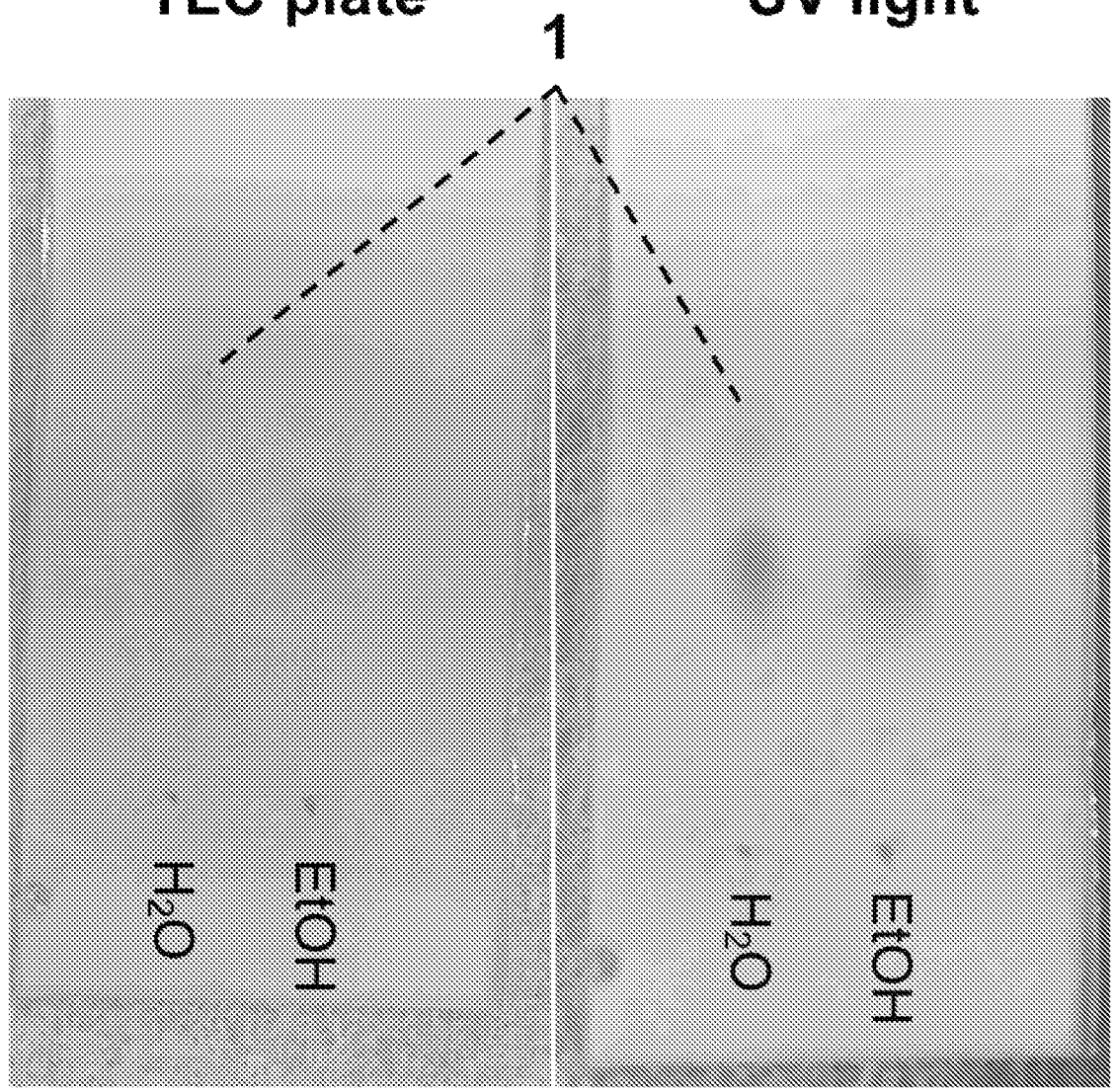
FIG. 26A shows reverse phase TLC (C18 silica, eluent: water/methanol=1:3, v/v) analysis of 1.0 mM ICG after 48 h storage in water or ethanol at room temperature and low photon intensity light (only exposed to lab lights during sample preparation and when aliquots were removed from samples). The results suggest that dimerization of ICG to form 1 is favored in water.
Figure 26B:
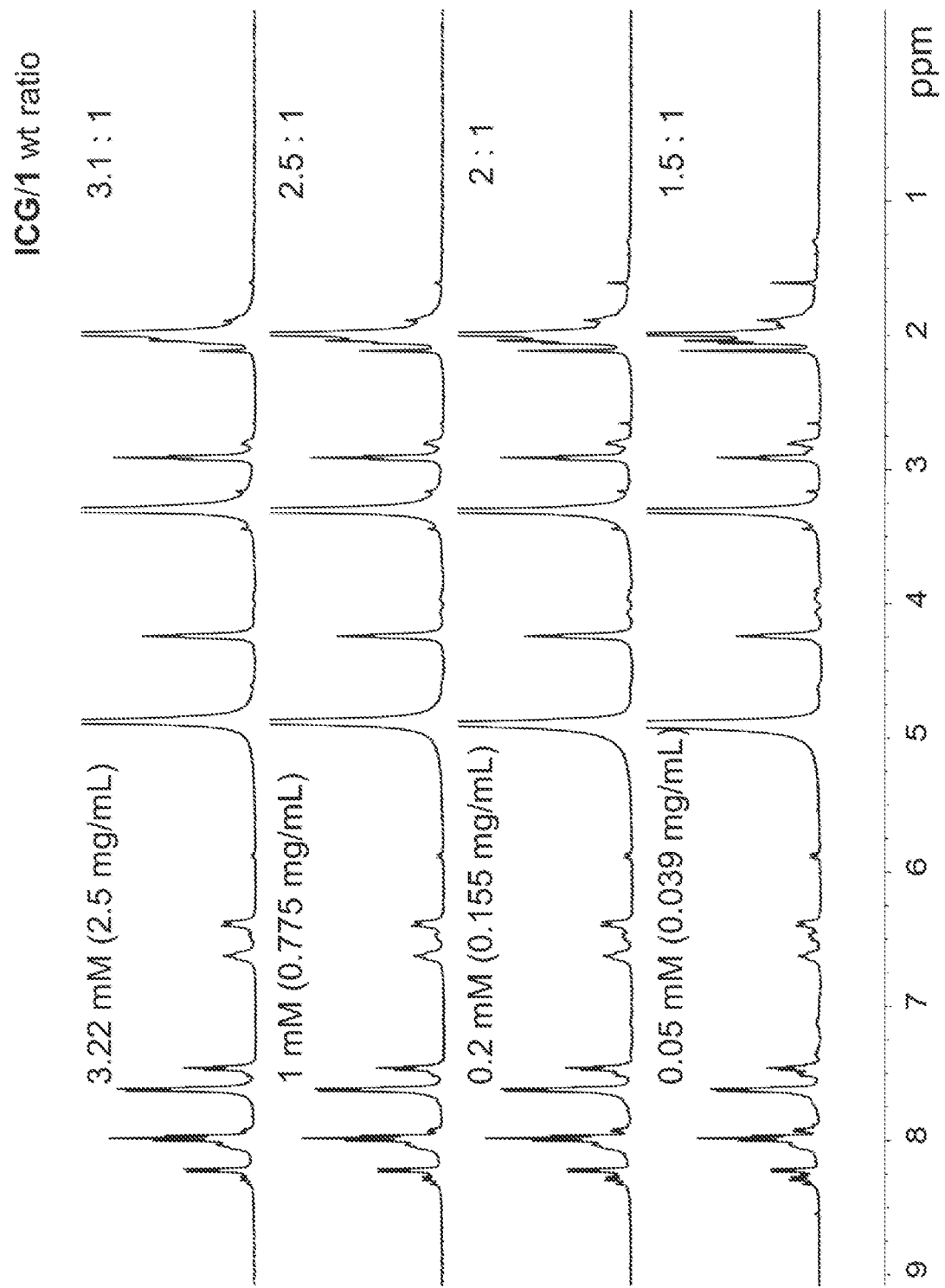
FIG. 26B shows $^1$H NMR spectra (500 MHz, methanol-$d_4$, 25° C.) of aliquots taken from ICG solutions in water (different concentrations) after 72 h storage at room temperature and low photon intensity light. The weight ratios of ICG to oxidative dimer 1 were calculated by the integration ratio of the —$CH_2SO_3^-$ peaks in the NMR spectra acquired after the aliquots were lyophilized and dissolved in methanol-$d_4$. The results suggest that degradation of ICG to form oxidative dimer 1 in water is slower at higher concentrations even though rates for second order reactions depend inversely on concentration.
Figure 27:
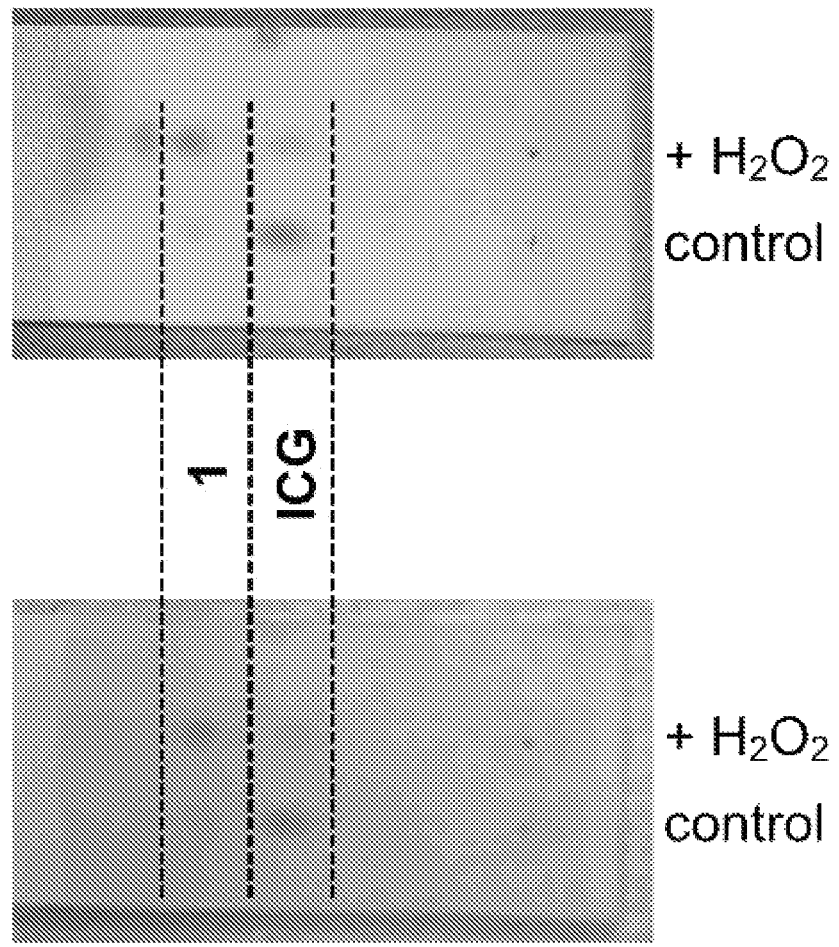
FIG. 27 shows reverse phase TLC (C18 silica, eluent: water/methanol=1:3, v/v) analysis of 1.0 mM ICG after 5 h storage in water with or without $H_2O_2$ (10 molar equivalents) at room temperature and low photon intensity light. The stock solution with added $H_2O_2$ contained a higher amount of oxidative dimer 1.

Under low photon intensity conditions, a stored solution of 1.0 mM ICG in water slowly produced 1 but an analogous solution of ICG in ethanol did not (FIG. 26A). The dimerization reaction to produce 1 under low photon intensity light conditions was enhanced when the aqueous solution of ICG (1.0 mM) included H$_2$O$_2$ (10 mM) (FIG. 27).

The chemical analysis data indicates that the dominant degradation pathway for a stored clinical formulation of aqueous ICG (1.0-2.5 mg/mL) is oxidative dimerization to produce 1. A deuterium kinetic isotope effect of 3.1 with ICG-d$_5$ (or ICG-d$_7$) was observed. Additionally, the high optical density of a clinical formulation produces a strong inner filter effect that inhibits light from contacting the dye molecules in the interior of the aqueous solution. In addition, there is extensive self-association of ICG in water to form face-to-face H-aggregates that favor rapid quenching of dye excited states. These two factors combine to slow photobleaching of a clinical ICG formulation in water (FIGS. 16-17, FIG. 26B).

The oxidative dimer 1 has a similar NIR absorption spectrum as ICG but the fluorescence quantum yield for oxidative dimer 1 is ~100 fold lower than for ICG (Table 1) and as shown in FIGS. 9A-10B, oxidative dimer 1 emits virtually no fluorescence.

TABLE 1

Photophysical properties at room temperature.

| Dye | Solvent | $\lambda^{abs}_{max}$ (nm) | $\lambda^{em}_{max}$ (nm) | ε (M$^{-1}$cm$^{-1}$) | R$^2$ | ΦF (%) | Brightness |
|---|---|---|---|---|---|---|---|
| ICG | DMSO | 795 | 820 | 224,000 | 0.999 | 16.7 ± 0.6 | 37,000 |
| ICG | FBS | 800 | 813 | 197,000 | 0.998 | 9.7 ± 0.4 | 19,000 |
| ICG-d$_5$ | DMSO | 793 | 819 | 253,000 | 0.999 | 19.8 ± 0.5 | 49,000 |
| ICG-d$_5$ | FBS | 796 | 813 | 205,000 | 0.997 | 10.5 ± 0.3 | 21,000 |
| ICG-d$_7$ | DMSO | 794 | 818 | 228,000 | 0.999 | 20.8 ± 0.5 | 48,000 |
| ICG-d$_7$ | FBS | 796 | 812 | 200,000 | 0.999 | 10.3 ± 0.4 | 21,000 |
| 1 | DMSO | 787 | 820 | 327,000 | 0.999 | 0.12 ± 0.06 | 390 |
| 1 | FBS | 796 | 820 | 256,000 | 0.998 | 0.12 ± 0.04 | 310 |

Figure 28A:
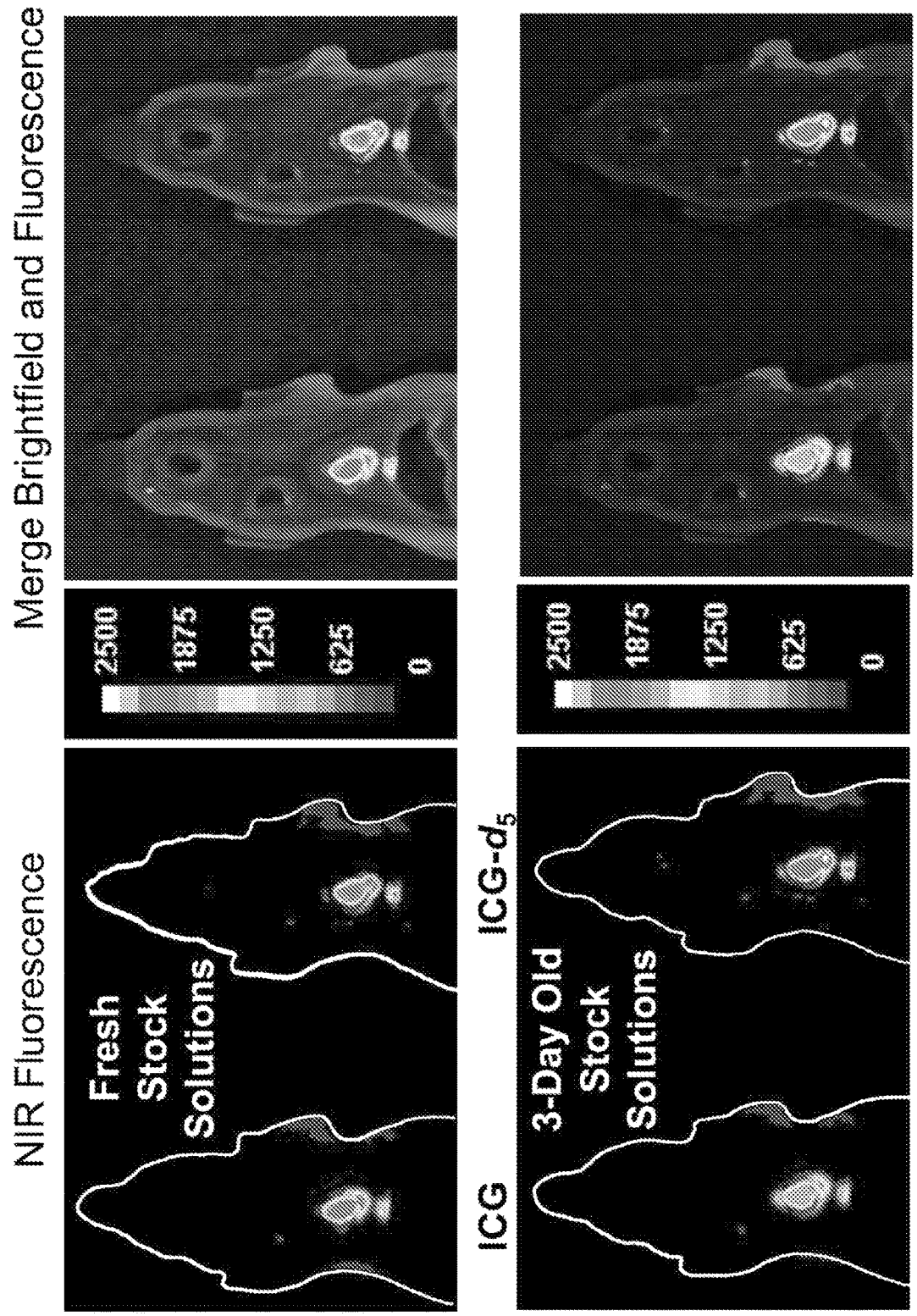
FIG. 28A shows (left) near-infrared (NIR) fluorescence images, and (right) merge of brightfield and NIR fluorescence images, of two mouse phantoms with heart portals containing FBS and an aliquot from a 1.0 mM stock solution of either ICG or ICG-$d_5$ (final dye concentration, 2 µM). The top pair of phantoms contain freshly prepared stock solutions, and the bottom pair of phantoms contain 3-day old stock solutions that had been stored primarily in the dark at room temperature (22° C.). Fluorescence intensity scale in arbitrarily units. Imaging parameters (ex: 745 nm, em: 850 nm, binning: low, exposure time: 3 s, FOV: 20, F-stop: 2, percent power: 50%).
Figures 28B, 28C:
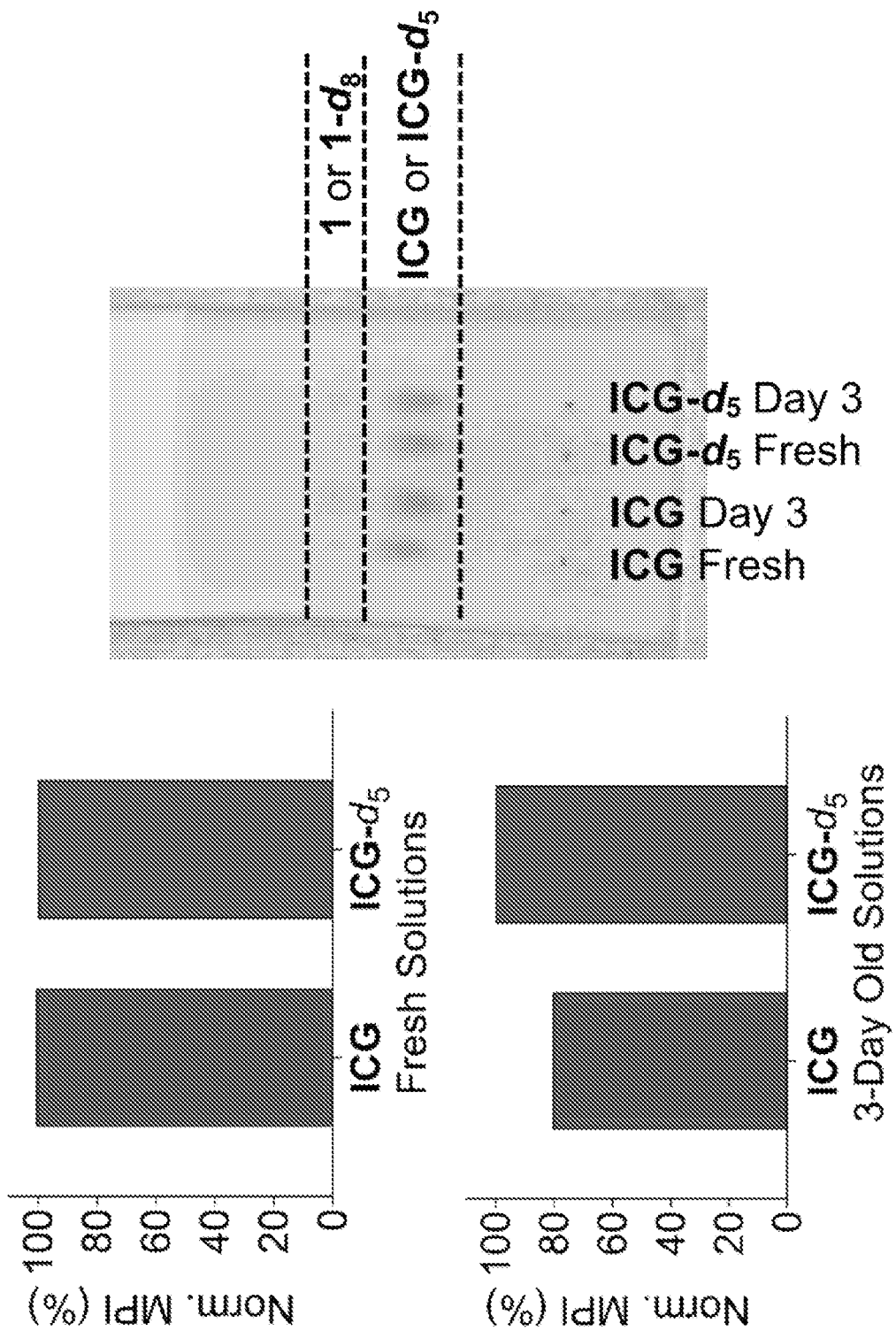
FIG. 28B shows normalized comparison of the mean pixel intensity (MPI) for each pair of fluorescent images, with the heart regions in each image treated as a region of interest and analyzed using ImageJ software.
FIG. 28C shows reverse phase TLC (C18 silica, eluent: water/methanol=1:3, v/v) analysis of 1.0 mM stock solutions. Negligible oxidative dimer is present in the freshly prepared solutions, but the 3-day old solution of ICG shows ~20% conversion to oxidative dimer 1, and the 3-day old solution of ICG-$d_5$ shows ~2% conversion to oxidative dimer 1-$d_8$.
Figure 29:
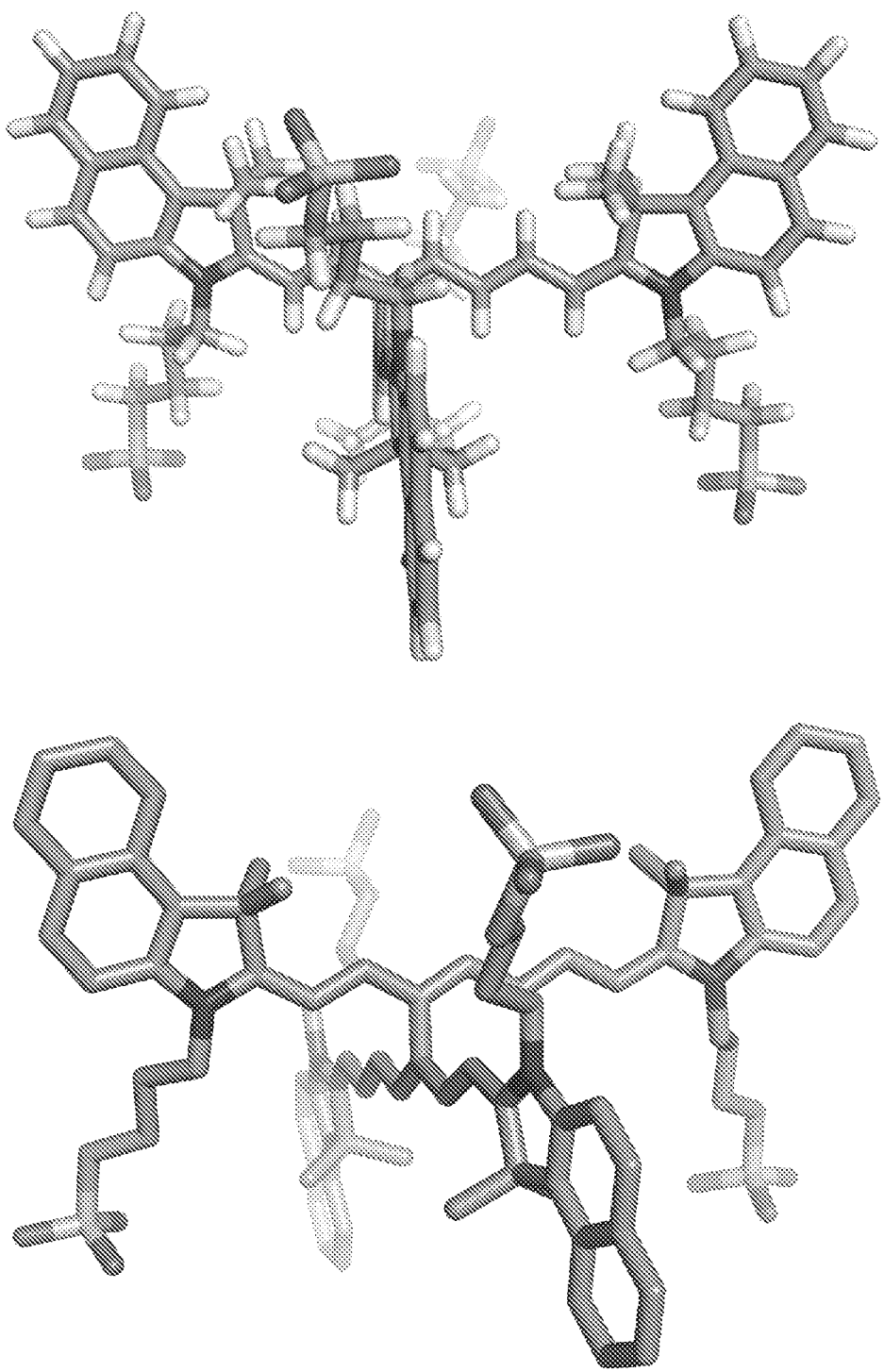
FIG. 29 shows a molecular model of oxidative dimer 1 at the PM7 level performed by the MOPAC program. Two views of the same model with hydrogens in the right view hidden for clarity. C: cyan, H: white, O: red, N: blue, S: yellow.

The relatively low fluorescence quantum yield for oxidative dimer 1 is consistent with that reported for an analogous oxidized dimer of a pentamethine cyanine dye, and an energy minimized molecular model of 1 (FIG. 29) reveals a highly twisted 3-dimensional shape with the two connected heptamethines oriented almost orthogonally. Compared to ICG there is little change in the absorption maxima band indicating very weak coupling of the polymethine transition state dipoles, but there is efficient intramolecular energy transfer and non-radiative decay of the excited state. In terms of fluorescence imaging, oxidative dimer 1 is a near-infrared (NIR) light-absorbing but non-fluorescent product of ICG degradation that builds up during storage of a clinical aqueous formulation and lowers the image brightness produced by the dose. To elucidate the difference in image brightness due to the change in stock solution stability, an NIR fluorescence imaging study was conducted where two mouse phantoms were compared with fillable organs (FIGS. 28A-28C). To mimic a typical ICG in vivo imaging scenario, the heart port of each phantom mouse was filled with FBS and an aliquot from a 1.0 mM stock solution of either ICG or ICG-d$_5$ (final dye concentration was 2 µM). NIR fluorescence images were acquired using a subject imaging station and the mean pixel intensities of the heart regions where determined. When the experiment used fresh stock solutions there was no difference in image intensities for the phantoms containing ICG or ICG-d$_5$, which is consistent with the matching fluorescence brightness observed when the dyes are in serum (Table 1). But when the imaging experiment was repeated using aliquots from stock solutions that had been stored in the dark for 3 days, the image intensity of the heart region containing ICG was 80% of the image intensity of the heart region filled with ICG-d$_5$. TLC analysis of the stock solutions showed that conversion into non-fluorescent 1 was the primary reason for the decreased ICG image intensity (FIGS. 28A-28C). This data indicates that the difference in NIR fluorescent image intensities would be even larger if the aqueous stock solutions were stored for longer periods or if they were exposed to more light during preparation and storage.

Example 15: Bovine Serum Albumin (BSA) Binding Studies

The titration experiments measured quenching of bovine serum albumin (BSA, 1 mL of 2 µM solution in pH 7.4 PBS buffer) tryptophan fluorescence at 37° C. as dye was added incrementally. A fluorescence spectrum (ex: 280 nm, slit width: 2 nm) was acquired after each dye aliquot was added (2 µL of 1 mM dye stock solutions in water). After each aliquot addition, the solution was mixed and allowed to equilibrate at 37° C. for 5 min before spectral acquisition. Association constants were determined by plotting the change in fluorescence intensity at 345 nm verses molar equivalents using 1:1 binding stoichiometry on the BindFit software. Experiments were done in triplicates. Equations for determining association and dissociation constant are shown below:

$$F = \frac{1}{2}k\left\{\left([BSA] + [Dye] + \frac{1}{K_a}\right) - \sqrt{\left([BSA] + [Dye] + \frac{1}{K_a}\right)^2 - 4[BSA][Dye]}\right\}$$

$$K_d = \frac{1}{K_a}$$

where F is the fluorescence intensity of tryptophan after adding certain amount of dye, k is the proportionality constant for BSA tryptophan under the experimental condition, $K_a$ is the association constant, [BSA] (2 µM) and [Dye] are the concentration of BSA and dye in the solution, respectively, $K_d$ is the dissociation constant.

TABLE 2

Dissociation constants ($K_d$) of BSA binding to different dyes in pH 7.4 PBS buffer at 37° C. as determined by fluorescence titration. Errors are ± 15%.

| Dyes | $K_d$ (µM) |
|---|---|
| ICG | 2.9 ± 0.4 |
| ICG-d$_5$ | 2.6 ± 0.4 |
| ICG-d$_7$ | 3.3 ± 0.4 |
| 1 | 34 ± 4 |

A notable pharmaceutical property of ICG is its high affinity for blood proteins which ensures that it does not leave the vasculature of a living subject. The oxidative dimer 1 exhibits a higher retention factor ($R_f$ value) on a reverse phase TLC plate than ICG, thus indicating that oxidative dimer 1 has a more polar molecular structure. The higher polarity of oxidative dimer 1 as compared to ICG is consistent with the molecular model shown in FIG. 29, which illustrates a dispersed projection of the four anionic sulfonate groups. The combination of polyanionic charge and non-planar shape indicated that oxidative dimer 1 would have relatively low affinity for blood proteins, and this low affinity was confirmed by measuring dissociation constants for binding to bovine serum albumin in pH 7.4 PBS buffer at 37° C. (FIGS. 11A-14B). The measured values of $K_d$ for ICG, ICG-d$_5$, ICG-d$_7$ were all within measurement error of 2.9 µM, which is near the literature value of 1.8 µM for ICG (Berezin, M. Y. et al. *Biochemistry*, 2011, 50, 2691-2700). In contrast, the $K_d$ for oxidative dimer 1 was ten-fold higher at 34 µM, indicating that if oxidative dimer 1 was present in the blood at the low micromolar dose concentrations (i.e., concentrations typically employed for clinical imaging), hardly any of oxidative dimer 1 would be associated with high molecular weight albumin protein. Thus, there is high potential for polar oxidative dimer 1 to extravasate from the bloodstream. For example, the structure of oxidative dimer 1 suggests that it might be an inhibitor of the organic anion transporters that mediate renal clearance of many environmental toxins or clinically important drugs. Since ICG is excreted chemically unchanged into the intestines, it is unlikely that ICG-d$_5$ (or ICG-d$_7$) will exhibit a difference in clinical pharmacokinetics or in vivo imaging performance as compared to ICG.

Figure 23A:
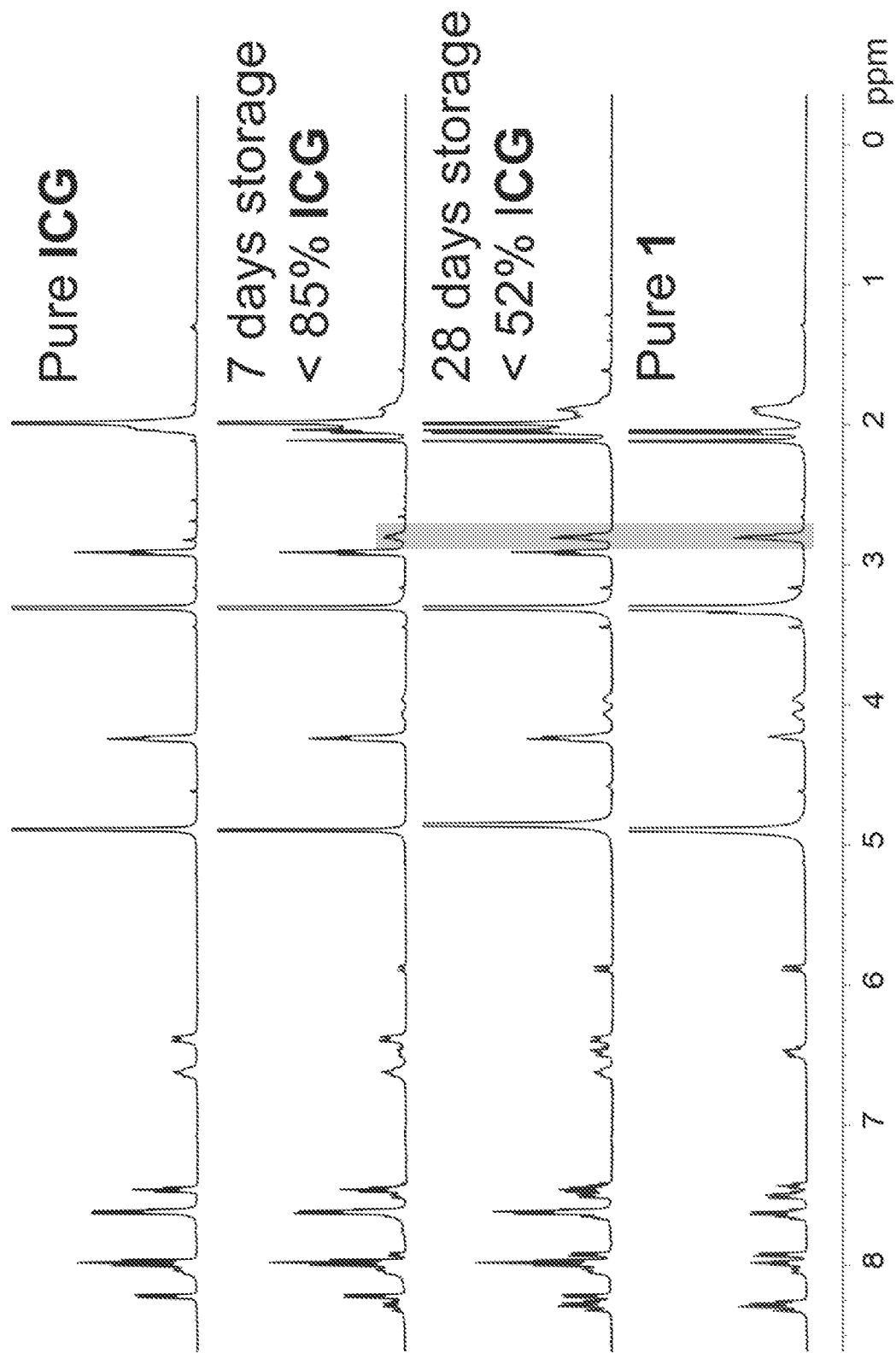
FIG. 23A shows $^1$H NMR spectra (500 MHz, methanol-$d_4$, 25° C.) of aqueous solutions of ICG that were stored at 4° C. in the dark. After 7 days and 28 days (separate samples), 1 mL aliquots were taken from each stock solution, the solutions were lyophilized, the solid residue was dissolved in methanol-$d_4$ and $^1$H NMR spectra were acquired. The weight percentages of ICG were calculated by integration of the —CH$_2$SO$_3^-$ peak (δ=2.91 ppm for ICG, δ=2.80 ppm for oxidative dimer 1). The gray stripe at ~2.8 ppm highlights the relative amounts of oxidative dimer 1 at each time point.
Figure 23B:
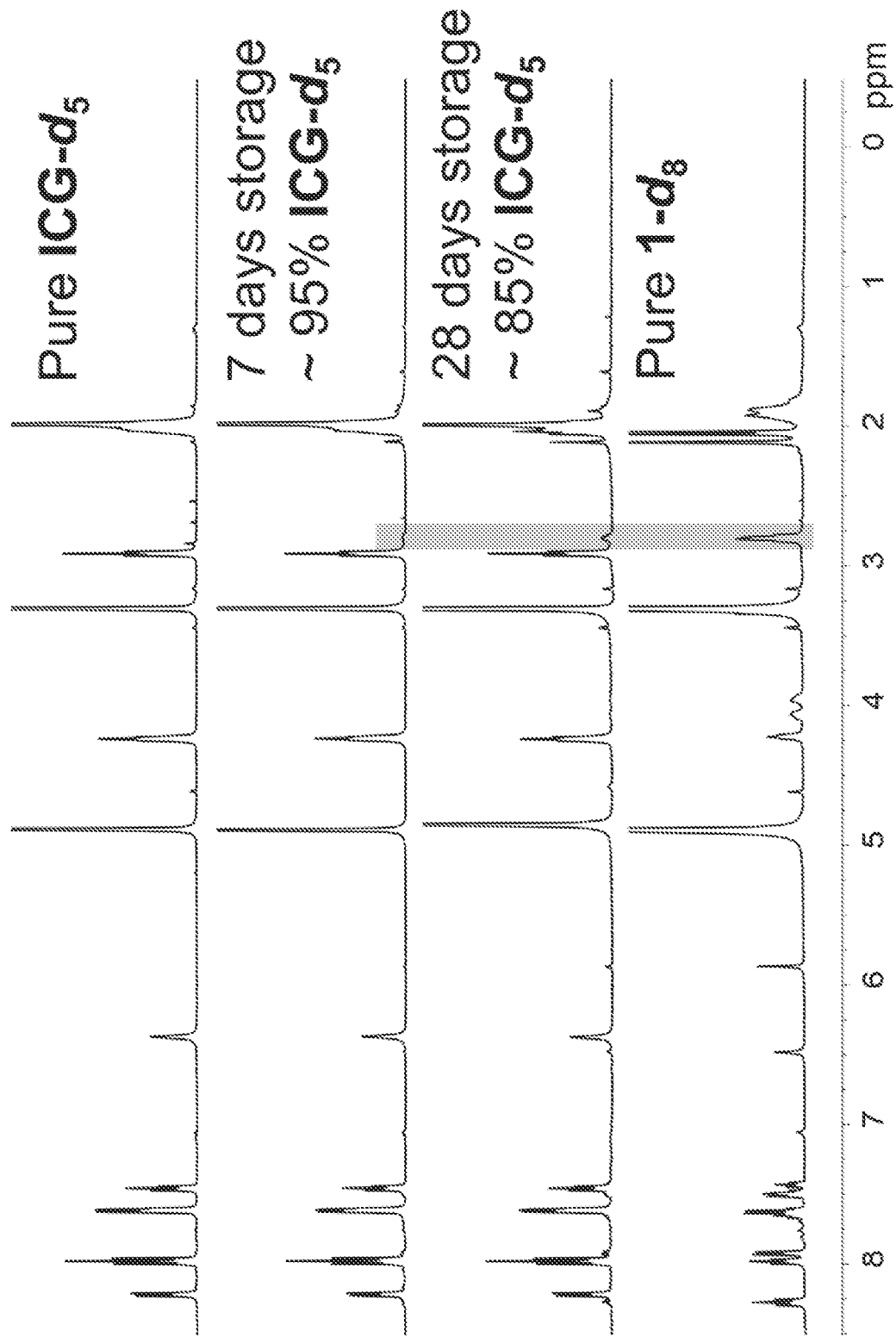
FIG. 23B shows $^1$H NMR spectra (500 MHz, methanol-$d_4$, 25° C.) of aqueous solutions of ICG-$d_5$ that were stored at 4° C. in the dark. After 7 days and 28 days (separate samples), 1 mL aliquots were taken from each stock solution, the solutions were lyophilized, the solid residue dissolved in methanol-$d_4$ and $^1$H NMR spectra were acquired. The weight percentages of ICG-$d_5$ were calculated by integration of the —CH$_2$SO$_3^-$ peak (δ=2.91 ppm for ICG-$d_5$, δ=2.80 ppm for oxidative dimer 1-$d_8$). The gray stripe at ~2.8 ppm highlights the relative amounts of oxidative dimer 1-$d_8$ at each time point. The results indicate that ICG-$d_5$ stock solution has increased stability in a refrigerator.

The shelf-life of an ICG stock solution is extended when stored in the dark at 4° C. in a refrigerator. As shown in FIGS. 23A-23B, the purity of an aqueous solution of ICG (1.0 mM) was 85% and 52% after 7- and 28-days storage, respectively, at 4° C. in the dark, whereas the purity of an analogous stored sample of ICG-d₅ (1.0 mM) was 99% and 85% after 7- and 28-days storage, respectively, at 4° C. in the dark.

The foregoing description of the specific aspects will so fully reveal the general nature of the technology that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the disclosure are set out in the following numbered clauses:

Clause 1. A compound of formula (I), or a pharmaceutically acceptable salt thereof:

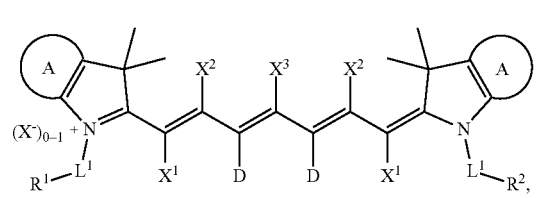

(I)

wherein:

$X^1$, $X^2$, and $X^3$ are each hydrogen;

A is a 6- to 12-membered arene, wherein A is unsubstituted or substituted with 1-5 substituents independently selected from the group consisting of $C_{1-4}$alkyl, —$OC_{1-4}$alkyl, $C_{1-2}$haloalkyl, —$OC_{1-2}$haloalkyl, halogen, —CN, —$NH_2$, —$NH(C_{1-4}$alkyl), —$N(C_{1-4}$alkyl)$_2$, —$YO_n^-$, —$YO_nH$, and —$YO_nM$;

$L^1$ is a bivalent straight or branched $C_{1-25}$ hydrocarbon chain, wherein $L^1$ is unsubstituted or substituted with 1-5 substituents independently selected from the group consisting of halogen, —$OC_{1-4}$alkyl, $C_{1-2}$haloalkyl, —$OC_{1-2}$haloalkyl, —OH, —CN, —$NH_2$, —$NH(C_{1-4}$alkyl), and —$N(C_{1-4}$alkyl)$_2$; wherein optionally one or more methylene units are independently replaced with —$CH_2$=$CH_2$—, —O—, —$CO_2$—, —C(O)—, —S—, —S(O)—, —$SO_2$—, —N(H)—, —$N(C_{1-4}$alkyl)-, —C(O)N(H)—, or —C(O)N($C_{1-4}$alkyl)-; and where 2 methylene groups replaced with —O—, —$CO_2$—, —C(O)—, —S—, —S(O)—, —$SO_2$—, —N(H)—, —$N(C_{1-4}$alkyl)-, —C(O)N(H)—, or —C(O)N($C_{1-4}$alkyl)- are separated by two or more carbon atoms in the alkylene;

$R^1$ and $R^2$ are each independently —$YO_n^-$, —$YO_nM$, —$YO_nH$, or hydrogen;

Y is sulfur or carbon;

n is 2, 3, or 4;

M is an alkali metal cation; and $X^-$ is chloride, bromide, iodide, perchlorate, or hypochlorite; with the proviso that when $R^1$ or $R^2$ is —$YO_n^-$, $X^-$ is absent, and the compound is not

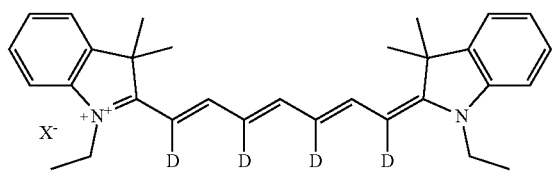

Clause 2. The compound of clause 1, or a pharmaceutically acceptable salt thereof, wherein $R^1$ is —$YO_n^-$.

Clause 3. The compound of clause 1 or 2, or a pharmaceutically acceptable salt thereof, wherein $R^2$ is —$YO_nM$ where M is Na.

Clause 4. The compound of any one of clauses 1-3, or a pharmaceutically acceptable salt thereof, wherein Y is sulfur.

Clause 5. The compound of any one of clauses 1-4, or a pharmaceutically acceptable salt thereof, wherein n is 3.

Clause 6. The compound of any one of clauses 1-5, or a pharmaceutically acceptable salt thereof, wherein the hydrogen at $X^1$, $X^2$, and $X^3$ are each deuterium.

Clause 7. The compound of any one of clauses 1-5, or a pharmaceutically acceptable salt thereof, wherein the hydrogen at $X^1$ and $X^2$ are each deuterium.

Clause 8. The compound of any one of clauses 1-5, or a pharmaceutically acceptable salt thereof, wherein the hydrogen at $X^2$ and $X^3$ are each deuterium.

Clause 9. The compound of any one of clauses 1-5, or a pharmaceutically acceptable salt thereof, wherein the hydrogen at $X^3$ is deuterium.

Clause 10. The compound of any one of clauses 1-5, or a pharmaceutically acceptable salt thereof, wherein the hydrogen at $X^2$ is deuterium.

Clause 11. The compound of any one of clauses 1-5, or a pharmaceutically acceptable salt thereof, wherein the hydrogen at $X^1$ is deuterium.

Clause 12. The compound of any one of clauses 1-11, or a pharmaceutically acceptable salt thereof, wherein the compound is selected from the group consisting of:

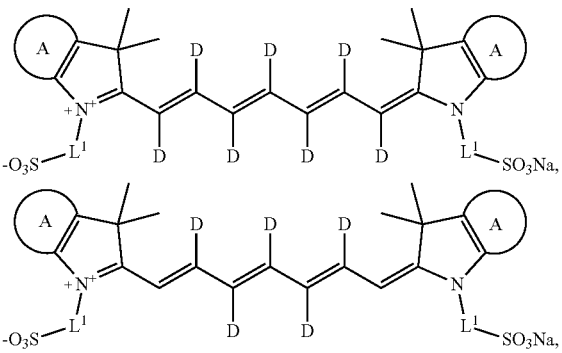

-continued

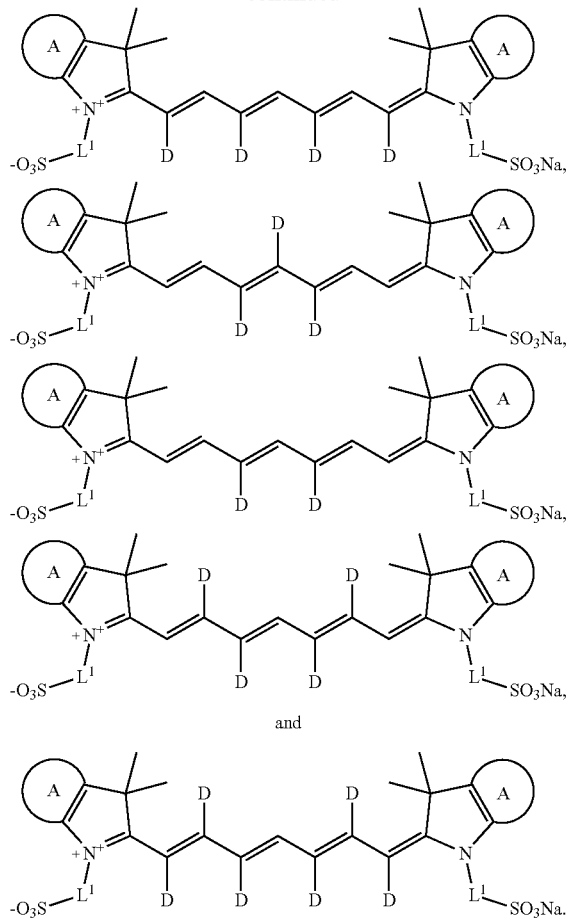

Clause 13. The compound of any one of clauses 1-12, or a pharmaceutically acceptable salt thereof, wherein A is

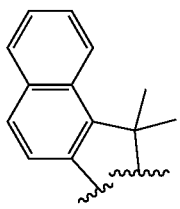

Clause 14. The compound of any one of clauses 1-13, or a pharmaceutically acceptable salt thereof, wherein A is

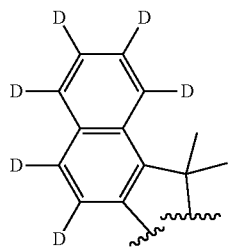

Clause 15. The compound of any one of clauses 1-14, or a pharmaceutically acceptable salt thereof, wherein $L^1$ is a $C_{1-10}$ hydrocarbon chain.

Clause 16. The compound of any one of clauses 1-15, or a pharmaceutically acceptable salt thereof, wherein $L^1$ is

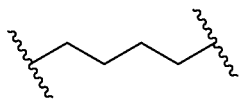

Clause 17. The compound of any one of clauses 1-16, or a pharmaceutically acceptable salt thereof, wherein the compound is a compound of formula (Ia):

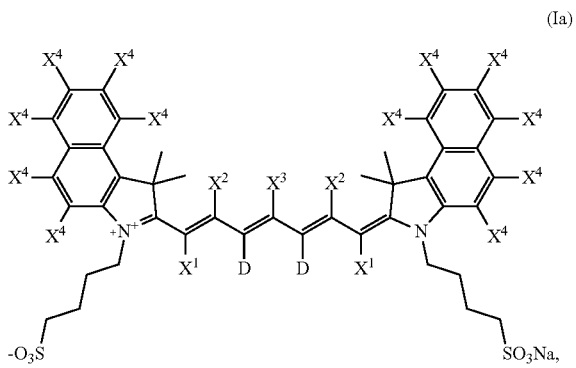

where $X^1$, $X^2$, $X^3$, and $X^4$ are each hydrogen.

Clause 18. The compound of clause 17, or a pharmaceutically acceptable salt thereof, wherein the hydrogen at $X^1$, $X^2$, and $X^3$ are each deuterium.

Clause 19. The compound of clause 17, or a pharmaceutically acceptable salt thereof, wherein the hydrogen at $X^1$ and $X^2$ are each deuterium.

Clause 20. The compound of clause 17, or a pharmaceutically acceptable salt thereof, wherein the hydrogen at $X^2$ and $X^3$ are each deuterium.

Clause 21. The compound of clause 17, or a pharmaceutically acceptable salt thereof, wherein the hydrogen at $X^3$ is deuterium.

Clause 22. The compound of clause 17, or a pharmaceutically acceptable salt thereof, wherein the hydrogen at $X^2$ is deuterium.

Clause 23. The compound of clause 17, or a pharmaceutically acceptable salt thereof, wherein the hydrogen at $X^1$ is deuterium.

Clause 24. The compound of clause 17, or a pharmaceutically acceptable salt thereof, wherein the hydrogen at $X^1$, $X^2$, $X^3$, and $X^4$ are each deuterium.

Clause 25. The compound of any one of clauses 1-24, or a pharmaceutically acceptable salt thereof, wherein the compound is selected from the group consisting of

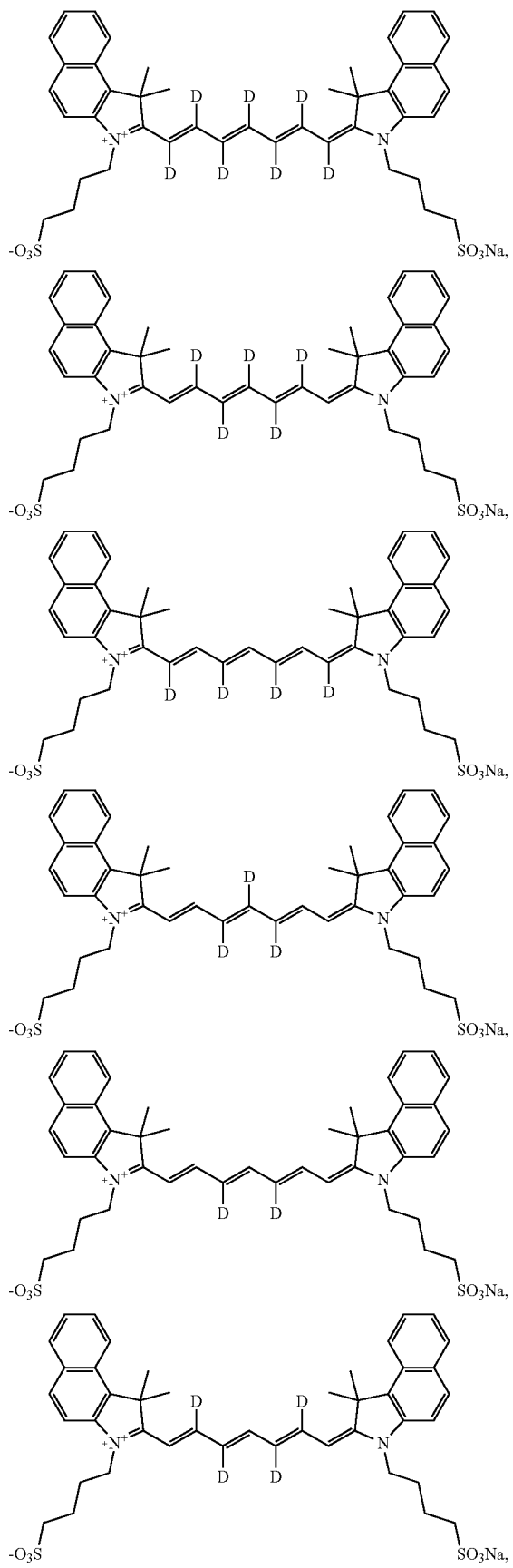

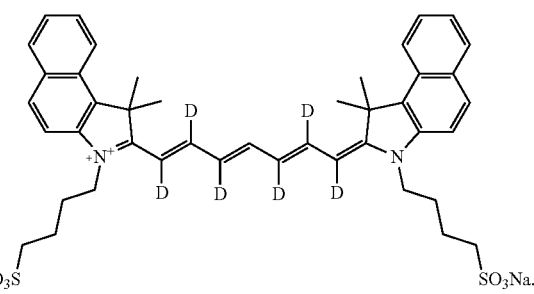

Clauses 26. A compound of any one of clauses 1-25, or a pharmaceutically acceptable salt thereof, wherein that compound has at least 50% deuterium incorporation at each deuterium label.

Clause 27. A compound of any one of clauses 1-26, or a pharmaceutically acceptable salt thereof, wherein that compound has at least 75% deuterium incorporation at each deuterium label.

Clause 28. A compound of any one of clauses 1-27, or a pharmaceutically acceptable salt thereof, wherein that compound has at least 90% deuterium incorporation at each deuterium label.

Clause 29. A compound of any one of clauses 1-28, or a pharmaceutically acceptable salt thereof, wherein that compound has at least 99% deuterium incorporation at each deuterium label.

Clause 30. A compound of any one of clauses 1-29, or a pharmaceutically acceptable salt thereof, wherein that compound has at least 99.5% deuterium incorporation at each deuterium label.

Clause 31. An aqueous formulation, comprising the compound of any one of clauses 1-30, or a pharmaceutically acceptable salt thereof, water, and at least one pharmaceutically acceptable excipient.

Clause 32. The aqueous formulation of clause 31, wherein at least one of the pharmaceutically acceptable excipients is sodium iodide.

Clause 33. The aqueous formulation of clause 31 or 32, wherein at least one of the pharmaceutically acceptable excipients is selected from the group consisting of sodium phosphate, sodium diphosphate, sodium triphosphate, sodium bicarbonate, sodium ascorbate, and combinations thereof.

Clause 34. A method for identifying abnormal tissue in a subject during an operative, radiologic, or endoscopic procedure comprising:
(a) administering to the subject the aqueous formulation of any one of embodiments 31-33;
(b) conducting the procedure while illuminating the area of interest with an illumination source emitting electromagnetic radiation; and
(c) imaging the abnormal tissue with an imaging device.

Clause 35. The method of clause 34, further comprising treating the abnormal tissue using a method selected from the group consisting of external beam radiation, laser therapy, surgical removal, and combinations thereof.

Clause 36. A therapeutic method for killing or ablating cells and tissue within a site of abnormal tissue in a subject comprising:

(a) administering to the subject the formulation of any one of clauses 31-33;
(b) illuminating the area of interest with electromagnetic radiation to cause the compound in the subject to release energy that kills cells or ablates cells and tissue within the site of abnormal tissue.

Clause 37. A method for obtaining an angiographic image of tissue in a subject comprising:
(a) parenterally administering to the subject, the aqueous formulation of any one of clauses 31-33;
(b) applying energy to cause the compound in the subject to fluoresce; and
(c) obtaining an angiographic image of the tissue while the compound fluoresces.

Clause 38. A diagnostic method comprising:
(a) parenterally administering a known amount of the aqueous formulation of any one of clauses 31-33 to a subject;
(b) continuously measuring the concentration of the compound in the subject's bloodstream; and
(c) analyzing the compound concentration data obtained in (b) to determine the change in compound concentration over time.

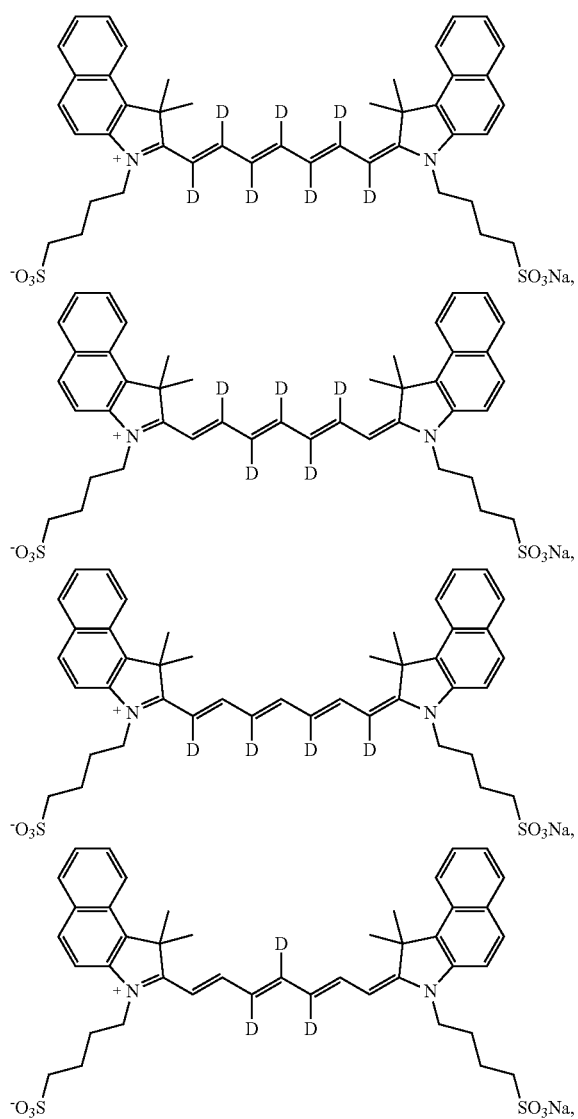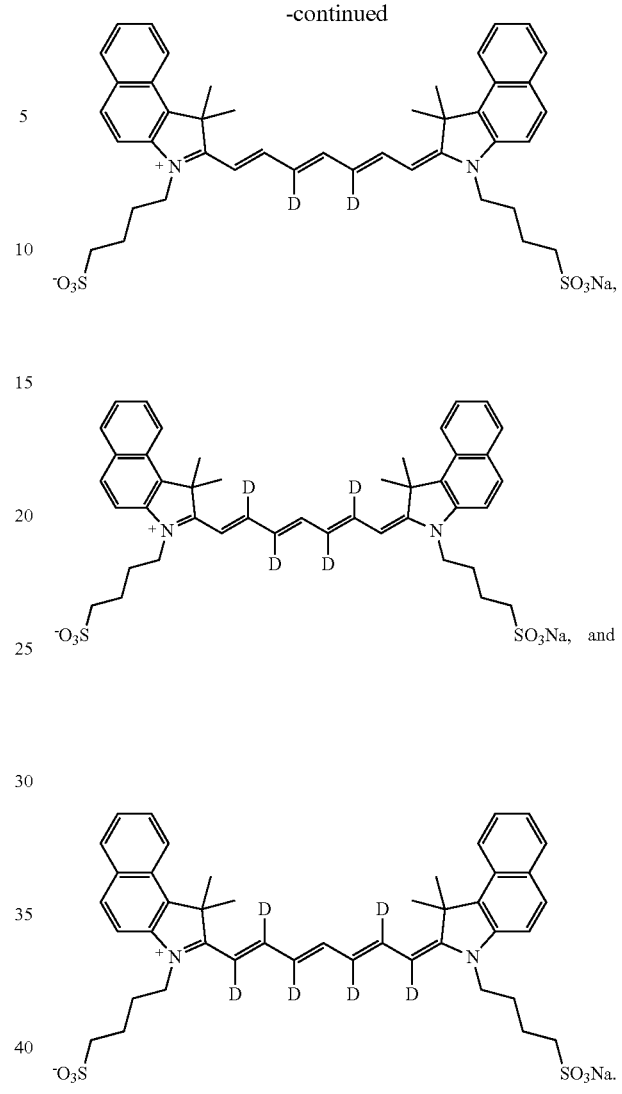

What is claimed:
1. A compound selected from the group consisting of:

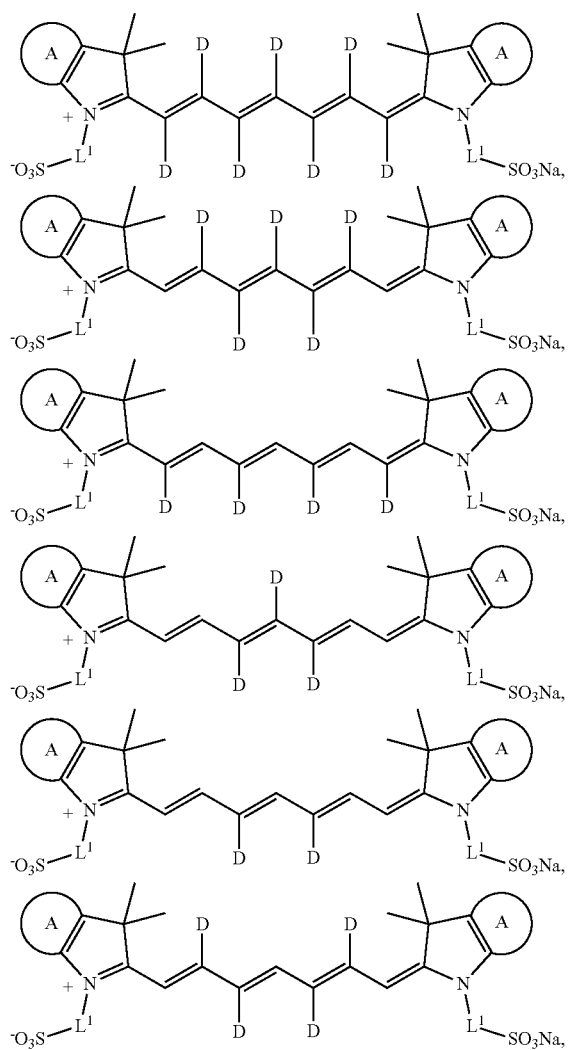

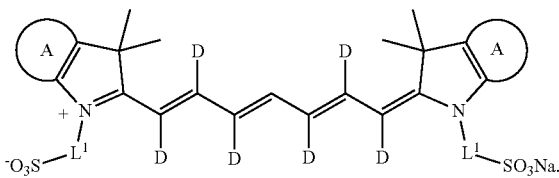

or a pharmaceutically acceptable salt thereof, wherein:
D is deuterium;
A is a 6- to 12-membered arene, wherein A is unsubstituted or substituted with 1-5 substituents independently selected from the group consisting of $C_{1-4}$alkyl, —$OC_{1-4}$alkyl, $C_{1-2}$haloalkyl, —$OC_{1-2}$haloalkyl, halogen, —CN, —$NH_2$, —$NH(C_{1-4}$alkyl), —$N(C_{1-4}$alkyl$)_2$, —$YO_n^-$, —$YO_nH$, and —$YO_nM$;
$L^1$ is a $C_{1-10}$ hydrocarbon chain;
Y is sulfur or carbon;
n is 2, 3, or 4; and M is an alkali metal cation.

2. The compound of claim 1, or a pharmaceutically acceptable salt thereof, wherein Y is sulfur.

3. The compound of claim 1, or a pharmaceutically acceptable salt thereof, wherein n is 3.

4. The compound of claim 1, or a pharmaceutically acceptable salt thereof, wherein A is

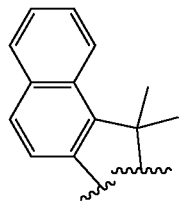

5. The compound of claim 1, or a pharmaceutically acceptable salt thereof, wherein A is

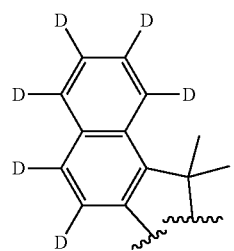

6. The compound of claim 1, or a pharmaceutically acceptable salt thereof, wherein $L^1$ is

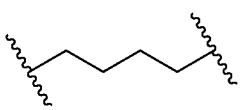

7. The compound of claim 1, or a pharmaceutically acceptable salt thereof, wherein the compound is selected from the group consisting of